(12) United States Patent
Bornhop et al.

(10) Patent No.: US 10,261,013 B2
(45) Date of Patent: Apr. 16, 2019

(54) ROBUST INTERFEROMETER AND METHODS OF USING SAME

(71) Applicant: Vanderbilt University, Nashville, TN (US)

(72) Inventors: Darryl J. Bornhop, Nashville, TN (US); Michael Kammer, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 70 days.

(21) Appl. No.: 15/199,417

(22) Filed: Jun. 30, 2016

(65) Prior Publication Data

US 2016/0327480 A1    Nov. 10, 2016

Related U.S. Application Data

(63) Continuation of application No. PCT/US2016/014439, filed on Jan. 22, 2016.

(60) Provisional application No. 62/107,308, filed on Jan. 23, 2015.

(51) Int. Cl.
*G01N 21/45* (2006.01)
*G01B 9/02* (2006.01)
*G01N 21/75* (2006.01)

(52) U.S. Cl.
CPC ......... *G01N 21/45* (2013.01); *G01B 9/02001* (2013.01); *G01N 21/75* (2013.01); *G01N 2021/458* (2013.01); *G01N 2201/06113* (2013.01)

(58) Field of Classification Search
CPC ...................... G01N 21/45; G01N 2021/7779
See application file for complete search history.

(56) References Cited

U.S. PATENT DOCUMENTS

| | | | |
|---|---|---|---|
| 3,567,113 | A | 3/1971 | Stansell et al. |
| 3,687,808 | A | 8/1972 | Merigan, Jr. |
| 4,093,759 | A | 6/1978 | Otsuki et al. |
| 4,265,554 | A | 5/1981 | Clancy et al. |
| 4,268,554 | A | 5/1981 | Gras |
| 4,443,106 | A | 4/1984 | Yasuda et al. |
| 4,469,863 | A | 9/1984 | Ts'o et al. |

(Continued)

FOREIGN PATENT DOCUMENTS

| | | |
|---|---|---|
| CA | 2584824 | 10/2005 |
| CA | 2584824 A1 | 5/2006 |

(Continued)

OTHER PUBLICATIONS

U.S. Appl. No. 60/620,661, filed Oct. 22, 2004, Bornhop (Vanderbilt University).

(Continued)

*Primary Examiner* — Paul S Hyun
(74) *Attorney, Agent, or Firm* — Ballard Spahr LLP

(57) ABSTRACT

Provided are improved optical detection systems and methods for using same, which systems and methods comprise single channel interferometric detection systems and methods for determining a characteristic property of samples. Such interferometric detection systems and methods employ a light beam that impinges two or more discrete zones along a channel, thereby avoiding variations that can result in increases in detection limits and/or measurement errors.

20 Claims, 34 Drawing Sheets

(56) References Cited

U.S. PATENT DOCUMENTS

| | | |
|---|---|---|
| 4,476,301 A | 10/1984 | Imbach et al. |
| 4,587,044 A | 5/1986 | Miller et al. |
| 4,605,735 A | 8/1986 | Miyoshi et al. |
| 4,660,974 A | 4/1987 | Machler et al. |
| 4,667,025 A | 5/1987 | Miyoshi et al. |
| 4,683,195 A | 7/1987 | Mullis et al. |
| 4,683,202 A | 7/1987 | Mullis |
| 4,699,951 A | 10/1987 | Allenson et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,895,431 A | 1/1990 | Tsujiuchi et al. |
| 4,904,582 A | 2/1990 | Tullis |
| 4,908,112 A | 3/1990 | Pace |
| 4,948,882 A | 8/1990 | Ruth |
| 4,950,074 A | 8/1990 | Fabricius et al. |
| 4,958,013 A | 9/1990 | Letsinger |
| 4,976,154 A | 12/1990 | Schneider et al. |
| 4,981,957 A | 1/1991 | Lebleu et al. |
| 4,990,925 A | 2/1991 | Edelsohn et al. |
| 5,023,243 A | 6/1991 | Tullis |
| 5,034,506 A | 7/1991 | Summerton et al. |
| 5,073,024 A | 12/1991 | Valette et al. |
| 5,082,830 A | 1/1992 | Brakel et al. |
| 5,108,179 A | 4/1992 | Myers |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,120,131 A | 6/1992 | Lukosz |
| 5,125,740 A | 6/1992 | Sato et al. |
| 5,130,302 A | 7/1992 | Spielvogel et al. |
| 5,134,066 A | 7/1992 | Rogers et al. |
| 5,138,045 A | 8/1992 | Cook et al. |
| 5,165,005 A | 11/1992 | Klainer et al. |
| 5,166,315 A | 11/1992 | Summerton et al. |
| 5,173,747 A | 12/1992 | Boiarski et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,215,883 A | 6/1993 | Chu |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,268,305 A | 12/1993 | Ribi et al. |
| 5,272,250 A | 12/1993 | Spielvogel et al. |
| 5,273,633 A | 12/1993 | Wang |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,304,487 A | 4/1994 | Wilding et al. |
| 5,305,071 A | 4/1994 | Wyatt |
| 5,309,330 A | 5/1994 | Pillers et al. |
| 5,317,098 A | 5/1994 | Shizuya et al. |
| 5,319,080 A | 6/1994 | Leumann |
| 5,321,131 A | 6/1994 | Agrawal et al. |
| 5,325,170 A | 6/1994 | Bornhop |
| 5,350,697 A | 9/1994 | Swope et al. |
| 5,351,678 A | 10/1994 | Clayton et al. |
| 5,359,044 A | 10/1994 | Cook et al. |
| 5,367,066 A | 11/1994 | Urdea et al. |
| 5,371,241 A | 12/1994 | Brush |
| 5,377,008 A | 12/1994 | Ridgway et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,426,505 A | 6/1995 | Geiser et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,456,245 A | 10/1995 | Bornhop et al. |
| 5,456,885 A | 10/1995 | Coleman et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,479,257 A | 12/1995 | Hashimoto |
| 5,484,908 A | 1/1996 | Froehler et al. |
| 5,485,277 A | 1/1996 | Foster |
| 5,485,312 A | 1/1996 | Homer et al. |
| 5,486,603 A | 1/1996 | Buhr |
| 5,489,677 A | 2/1996 | Sanghvi et al. |
| 5,502,177 A | 3/1996 | Matteucci et al. |
| 5,502,561 A | 3/1996 | Hutchins et al. |
| 5,510,475 A | 4/1996 | Agrawal et al. |
| 5,512,439 A | 4/1996 | Homes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,852 A | 9/1996 | Nakamura et al. |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,578,832 A | 11/1996 | Trulson et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,593,839 A | 1/1997 | Hubbell et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,695 A | 2/1997 | Pease et al. |
| 5,599,923 A | 2/1997 | Sessler et al. |
| 5,599,928 A | 2/1997 | Hemmi et al. |
| 5,602,240 A | 2/1997 | De Mesmaeker et al. |

(56) References Cited

U.S. PATENT DOCUMENTS

| | | |
|---|---|---|
| 5,608,046 A | 3/1997 | Cook et al. |
| 5,610,289 A | 3/1997 | Cook et al. |
| 5,610,300 A | 3/1997 | Altmann et al. |
| 5,613,013 A | 3/1997 | Schuette |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,631,734 A | 5/1997 | Stern et al. |
| 5,633,312 A | 5/1997 | Kabeta et al. |
| 5,633,360 A | 5/1997 | Bischofberger et al. |
| 5,633,708 A | 5/1997 | Svendsen |
| 5,636,017 A | 6/1997 | Bruno et al. |
| 5,639,873 A | 6/1997 | Barascut et al. |
| 5,646,265 A | 7/1997 | McGee |
| 5,658,873 A | 8/1997 | Bertsch-Frank et al. |
| 5,659,318 A | 8/1997 | Madsen et al. |
| 5,663,312 A | 9/1997 | Chaturvedula |
| 5,663,790 A | 9/1997 | Ekstrom et al. |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,694,210 A | 12/1997 | Newell et al. |
| 5,698,518 A | 12/1997 | Carson et al. |
| 5,700,920 A | 12/1997 | Altmann et al. |
| 5,712,321 A | 1/1998 | Cantor et al. |
| 5,714,331 A | 2/1998 | Buchardt et al. |
| 5,719,262 A | 2/1998 | Buchardt et al. |
| 5,740,291 A | 4/1998 | De Lasa et al. |
| 5,770,029 A | 6/1998 | Nelson et al. |
| 5,781,304 A | 7/1998 | Kotidis et al. |
| 5,804,453 A | 9/1998 | Chen |
| 5,815,258 A | 9/1998 | Nakanishi |
| 5,817,462 A | 10/1998 | Garini et al. |
| 5,824,204 A | 10/1998 | Jerman |
| 5,841,914 A | 11/1998 | Shieh et al. |
| 5,846,708 A | 12/1998 | Hollis et al. |
| 5,852,495 A | 12/1998 | Parce |
| 5,867,266 A | 2/1999 | Craighead |
| 5,915,034 A | 6/1999 | Nakajima et al. |
| 5,922,594 A | 7/1999 | Lofås |
| 5,928,627 A | 7/1999 | Kiefer et al. |
| 5,932,474 A | 8/1999 | Tsien et al. |
| 5,953,439 A | 9/1999 | Ishihara et al. |
| 5,976,336 A | 11/1999 | Dubrow et al. |
| 5,995,645 A | 11/1999 | Soenksen et al. |
| 6,008,378 A | 12/1999 | Tsien et al. |
| 6,054,271 A | 4/2000 | Tsien et al. |
| 6,108,458 A | 8/2000 | Hart |
| 6,123,798 A | 9/2000 | Gandhi et al. |
| 6,130,439 A | 10/2000 | Le Menn |
| 6,167,910 B1 | 1/2001 | Chow |
| 6,198,532 B1 | 3/2001 | Cabib et al. |
| 6,251,343 B1 | 6/2001 | Dubrow et al. |
| 6,321,791 B1 | 11/2001 | Chow |
| 6,322,683 B1 | 11/2001 | Wolk et al. |
| 6,381,025 B1 | 4/2002 | Bornhop et al. |
| 6,381,925 B2 | 5/2002 | Rejcek et al. |
| 6,451,569 B1 | 9/2002 | Tsien et al. |
| 6,480,282 B1 | 11/2002 | Chinowsky et al. |
| 6,493,090 B1 | 12/2002 | Lading et al. |
| 6,529,279 B2 | 3/2003 | de Groot et al. |
| 6,532,061 B2 | 3/2003 | Ortyn et al. |
| 6,533,914 B1 | 3/2003 | Liu |
| 6,559,947 B1 | 5/2003 | Turner |
| 6,576,430 B1 | 6/2003 | Hsieh et al. |
| 6,660,517 B1 | 12/2003 | Wilding et al. |
| 6,741,361 B2 | 5/2004 | Marron |
| 6,744,950 B2 | 6/2004 | Aleksoff |
| 6,760,103 B2 | 7/2004 | Shakespeare et al. |
| 6,798,509 B2 | 9/2004 | Sonehara et al. |
| 6,809,828 B2 | 10/2004 | Bornhop et al. |
| 6,962,690 B2 | 11/2005 | Kiefer et al. |
| 6,980,299 B1 | 12/2005 | de Boer |
| 7,011,948 B2 | 3/2006 | Chapman et al. |
| 7,045,171 B2 | 5/2006 | Bookbinder et al. |
| 7,130,060 B2 | 10/2006 | Bornhop et al. |
| 7,172,897 B2 | 2/2007 | Blackburn et al. |
| 7,173,986 B2 | 2/2007 | Wu |
| 7,202,076 B2 | 4/2007 | Cunningham et al. |
| 7,300,803 B2 | 11/2007 | Lin et al. |
| 7,835,013 B2 | 11/2010 | Jones et al. |
| 8,120,777 B2 | 2/2012 | Weinberger et al. |
| 8,134,707 B2 | 3/2012 | Bornhop et al. |
| 8,445,217 B2 | 5/2013 | Bornhop |
| 8,450,118 B2 | 5/2013 | Weinberger et al. |
| 8,673,827 B1 | 3/2014 | Hermes |
| 9,273,949 B2 | 3/2016 | Bornhop et al. |
| 9,562,853 B2 | 2/2017 | Bornhop et al. |
| 9,638,632 B2 | 5/2017 | Bornhop |
| 2001/0045358 A1 | 11/2001 | Kopf-Sill et al. |
| 2001/0050821 A1 | 12/2001 | Bickleder et al. |
| 2002/0002353 A1 | 1/2002 | Michal et al. |
| 2002/0022603 A1 | 2/2002 | Lichtenberger |
| 2002/0034580 A1 | 3/2002 | Yang et al. |
| 2002/0057432 A1 | 5/2002 | Ortyn et al. |
| 2002/0094528 A1 | 7/2002 | Salafsky |
| 2002/0128234 A1 | 9/2002 | Hubbell et al. |
| 2002/0135772 A1 | 9/2002 | Bornhop et al. |
| 2003/0020915 A1 | 1/2003 | Schueller et al. |
| 2003/0082516 A1 | 5/2003 | Straus |
| 2003/0087099 A1 | 5/2003 | Merrill et al. |
| 2003/0099598 A1 | 5/2003 | Kiefer et al. |
| 2003/0129579 A1 | 7/2003 | Bornhop et al. |
| 2003/0148922 A1 | 8/2003 | Knapp et al. |
| 2004/0058058 A1 | 3/2004 | Shchegolikhin et al. |
| 2004/0110276 A1 | 6/2004 | Amontov et al. |
| 2004/0115721 A1 | 6/2004 | Mao et al. |
| 2004/0218184 A1 | 11/2004 | Jorgenson et al. |
| 2004/0241765 A1 | 12/2004 | Zweig |
| 2005/0004348 A1 | 1/2005 | Miyamoto et al. |
| 2005/0014179 A1 | 1/2005 | Karlsson et al. |
| 2005/0019956 A1 | 1/2005 | Martin et al. |
| 2005/0083505 A1 | 4/2005 | Augustyn et al. |
| 2005/0106570 A1 | 5/2005 | Kataoka et al. |
| 2005/0175273 A1 | 8/2005 | Iida et al. |
| 2005/0190372 A1 | 9/2005 | Dogariu |
| 2005/0227374 A1 | 10/2005 | Cunningham |
| 2005/0244863 A1 | 11/2005 | Mir |
| 2005/0264819 A1 | 12/2005 | Arnz et al. |
| 2006/0012777 A1 | 1/2006 | Talbot et al. |
| 2006/0012800 A1 | 1/2006 | Bornhop et al. |
| 2006/0039004 A1 | 2/2006 | de Boer et al. |
| 2006/0147379 A1 | 7/2006 | Bornhop et al. |
| 2006/0183700 A1 | 8/2006 | Vater et al. |
| 2006/0256343 A1 | 11/2006 | Choma et al. |
| 2006/0263777 A1 | 11/2006 | Tong |
| 2006/0268260 A1 | 11/2006 | Liu et al. |
| 2006/0275179 A1 | 12/2006 | Viovy et al. |
| 2006/0275825 A1 | 12/2006 | Baird et al. |
| 2007/0012777 A1 | 1/2007 | Tsikos et al. |
| 2007/0030841 A1 | 2/2007 | Lee et al. |
| 2007/0048747 A1 | 3/2007 | Leslie et al. |
| 2007/0054339 A1 | 3/2007 | Lin et al. |
| 2007/0146888 A1 | 6/2007 | Schmidt et al. |
| 2007/0195321 A1 | 8/2007 | Soussaline et al. |
| 2008/0160187 A1 | 7/2008 | Murata et al. |
| 2008/0182239 A1 | 7/2008 | Mullinax et al. |
| 2008/0186488 A1 | 8/2008 | Kiesel et al. |
| 2008/0194723 A1 | 8/2008 | Hwang et al. |
| 2008/0248502 A1 | 10/2008 | Yamaguchi et al. |
| 2008/0259313 A1 | 10/2008 | Berndt |
| 2009/0009759 A1 | 1/2009 | Backman et al. |
| 2009/0103091 A1 | 4/2009 | Jones et al. |
| 2009/0135421 A1 | 5/2009 | Oldham et al. |
| 2009/0155832 A1 | 6/2009 | Lo et al. |
| 2009/0185190 A1 | 7/2009 | Weinberger et al. |
| 2009/0325199 A1 | 12/2009 | Geddes |
| 2010/0099203 A1 | 4/2010 | Chang et al. |
| 2010/0184056 A1 | 7/2010 | Weinberger et al. |
| 2010/0188665 A1 | 7/2010 | Dotson et al. |

(56) References Cited

U.S. PATENT DOCUMENTS

| | | |
|---|---|---|
| 2010/0191482 A1 | 7/2010 | Hasson et al. |
| 2011/0109907 A1 | 5/2011 | Meyers et al. |
| 2011/0155927 A1 | 6/2011 | Mitchell et al. |
| 2011/0157692 A1 | 6/2011 | Lin et al. |
| 2012/0015376 A1 | 1/2012 | Bornhop |
| 2012/0019834 A1* | 1/2012 | Bornhop ............... G01N 21/45 356/517 |
| 2012/0199742 A1 | 8/2012 | Wagner et al. |
| 2013/0021608 A1 | 1/2013 | Bornhop et al. |
| 2013/0040306 A1 | 2/2013 | Bornhop et al. |
| 2013/0224886 A1 | 8/2013 | Iwasaki et al. |
| 2013/0280715 A1 | 10/2013 | Bornhop et al. |
| 2013/0301055 A1 | 11/2013 | Bornhop et al. |
| 2013/0309661 A1 | 11/2013 | Bornhop |
| 2016/0000239 A1 | 1/2016 | Denby et al. |

FOREIGN PATENT DOCUMENTS

| | | |
|---|---|---|
| CH | 00959154.6 | 8/2000 |
| DE | 00959154.6 | 8/2000 |
| DK | 00959154.6 | 8/2000 |
| EP | 0721016 A2 | 7/1996 |
| EP | 0728520 A1 | 8/1996 |
| EP | 0785280 A2 | 7/1997 |
| EP | 0799797 A1 | 10/1997 |
| EP | 00959154.6 | 8/2000 |
| EP | 1210581 A1 | 6/2002 |
| EP | 05821243.2 | 10/2005 |
| EP | 1746385 A1 | 1/2007 |
| EP | 1805498 A2 | 7/2007 |
| EP | 08755681.7 | 5/2008 |
| EP | 10729387.0 | 1/2010 |
| EP | 2160590 A1 | 3/2010 |
| EP | 2386060 A2 | 11/2011 |
| EP | 16740808 | 1/2016 |
| FR | 2766922 A1 | 2/1999 |
| FR | 00959154.6 | 8/2000 |
| GB | 00959154.6 | 8/2000 |
| IL | 253607 | 7/2017 |
| JP | 2017-538694 | 7/2017 |
| NL | 00959154.6 | 8/2000 |
| SE | 00959154.6 | 8/2000 |
| WO | WO-90/05317 A1 | 5/1990 |
| WO | WO-95/22058 A1 | 8/1995 |
| WO | WO-95/25116 A1 | 9/1995 |
| WO | WO-97/02357 A1 | 1/1997 |
| WO | WO-97/27317 | 7/1997 |
| WO | WO-97/29212 A1 | 8/1997 |
| WO | PCT/US2000/020783 | 8/2000 |
| WO | WO-2001/014858 A1 | 3/2001 |
| WO | WO-2002/059579 A1 | 8/2002 |
| WO | WO-2004/023115 A1 | 3/2004 |
| WO | PCT/US2005/38168 | 10/2005 |
| WO | WO-2006/047408 A2 | 5/2006 |
| WO | WO-2007/002178 A2 | 1/2007 |
| WO | PCT/US2008/063679 | 5/2008 |
| WO | PCT/US2008/077145 | 9/2008 |
| WO | WO-2008/144496 A1 | 11/2008 |
| WO | WO-2009/039466 A1 | 3/2009 |
| WO | PCT/US2010/000047 | 1/2010 |
| WO | WO-2010/080710 A2 | 7/2010 |
| WO | WO-2010/129494 A2 | 11/2010 |
| WO | PCT/US2011/039982 | 6/2011 |
| WO | PCT/US2011/056171 | 10/2011 |
| WO | WO-2011/156713 A1 | 12/2011 |
| WO | WO-2012/051429 A1 | 4/2012 |
| WO | PCT/US2016/014439 | 1/2016 |
| WO | PCT/US2017/015296 | 1/2017 |
| WO | WO-2017/132483 | 8/2017 |

OTHER PUBLICATIONS

U.S. Appl. No. 11/666,046, filed Oct. 24, 2005 U.S. Pat. No. 8,134,707, Mar. 13, 2012, Bornhop (Vanderbilt University).
U.S. Appl. No. 13/401,303, filed Feb. 21, 2012, Bornhop (Vanderbilty University).
U.S. Appl. No. 60/938,887, filed May 18, 2007, Bornhop (Vanderbilty University).
U.S. Appl. No. 60/991,599, filed Nov. 30, 2007, Bornhop (Vanderbilt University).
U.S. Appl. No. 12/122,175, filed May 16, 2008 U.S. Pat. No. 7,835,013, Nov. 16, 2010, Bornhop (Vanderbilt University).
U.S. Appl. No. 60/973,829, filed Sep. 20, 2007, Bornhop (Vanderbilt University).
U.S. Appl. No. 12/674,610, filed Sep. 20, 2008 U.S. Pat. No. 8,445,217, May 21, 2013, Bornhop (Vanderbilt University).
U.S. Appl. No. 13/857,953, filed Apr. 5, 2013, Bornhop (Vanderbilt University).
U.S. Appl. No. 61/012,752, filed Dec. 10, 2007, Bornhop (Vanderbilt University).
U.S. Appl. No. 61/106,552, filed Oct. 17, 2008, Bornhop (Vanderbilt University).
U.S. Appl. No. 61/144,054, filed Jan. 12, 2009, Bornhop (Vanderbilt University).
PCT/US2010/000047, Jan. 8, 2010, Bornhop (Vanderbilt University).
U.S. Appl. No. 12/331,354, filed Dec. 9, 2008 U.S. Pat. No. 8,120,777, Feb. 21, 2012, Bornhop (Vanderbilt University).
U.S. Appl. No. 12/655,899, filed Nov. 29, 2010, Bornhop (Vanderbilt University).
U.S. Appl. No. 09/519,860, filed Mar. 6, 2000 U.S. Pat. No. 6,381,025, Apr. 30, 2002, Bornhop (Vanderbilt University).
U.S. Appl. No. 10/053,877, filed Jan. 24, 2002 U.S. Pat. No. 6,809,828, Oct. 26, 2004, Bornhop (Vanderbilt University).
U.S. Appl. No. 61/354,045, filed Jun. 11, 2010, Bornhop (Vanderbilt University).
U.S. Appl. No. 13/157,803, filed Jun. 10, 2011 U.S. Pat. No. 9,638,632, May 2, 2017, Bornhop (Vanderbilt University).
U.S. Appl. No. 61/392,890, filed Oct. 13, 2010, Bornhop (Vanderbilt University).
U.S. Appl. No. 13/879,523, filed Oct. 13, 2011, Bornhop (Vanderbilt University).
U.S. Appl. No. 61/445,352, filed Feb. 22, 2011, Bornhop (Vanderbilt University).
U.S. Appl. No. 13/402,104, filed Feb. 22, 2012 U.S. Pat. No. 9,562,853, Feb. 7, 2017, Bornhop (Vanderbilt University).
U.S. Appl. No. 61/447,802, filed Mar. 1, 2011, Bornhop (Vanderbilt University).
U.S. Appl. No. 13/409,557, filed Mar. 1, 2012, Bornhop (Vanderbilt University).
U.S. Appl. No. 61/645,660, filed May 11, 2012, Bornhop (Vanderbilt University).
U.S. Appl. No. 13/892,642, filed May 13, 2013 U.S. Pat. No. 9,273,949, Mar. 1, 2016, Bornhop (Vanderbilt University).
U.S. Appl. No. 62/107,308, filed Jan. 23, 2015, Bornhop (Vanderbilt University).
U.S. Appl. No. 62/288,926, filed Jan. 29, 2016, Bornhop (Vanderbilt University).
Ababou et al., (2007) Survey of the year 2005: literature on applications of isothermal titration calorimetry. J. Mol. Recognit.
Abato P, "An enzymatic method for determining enantiomeric excess," *Journal of the American Chemical Society*, 123: 9206-9207 (2001).
Abbas AK, et al., Cellular and Molecular Immunology (Saunders, Philadelphia, ed. Fifth, 2003).
Adams et al. (2013) The effect of hybridization-induced secondary structure alterations on RNA detection using backscattering.
Adanyi, et al., "Development of immunosensor based on OWLS technique for determining Aflatoxin B1 and Ochratoxin A," Biosens Bioe/ectron 22:797-802 (2007).
Ahlert J, et al., "The calicheamicin gene cluster and its iterative type I enediyne PKS," *Science*, 297: 1173-1176 (2002).
Alunni S, et al., "Mechanisms of inhibition of phenylalanine ammonialyase by phenol inhibitors and phenol/glycine synergistic inhibitors," *Archives of Biochemistry and Biophysics*, 412: 170-175 (2003).

(56) References Cited

OTHER PUBLICATIONS

Amendment after Notice of Allowance (Rule 312) dated Jan. 3, 2017 by the U.S. Patent and Trademark Office for U.S. Appl. No. 13/157,803, filed Jun. 10, 2011 and granted as U.S. Pat. No. 9,638,632 on May 2, 2017 (Inventor—Darryl J. Bornhop et al.) (3 pages).
Amendment after Notice of Allowance filed on Feb. 19, 2004 for U.S. Appl. No. 10/053,877, filed Jan. 24, 2002 (Applicant—Vanderbilt University // Inventors—Bornhop et al.) (8 pages).
Anderson Jr, et al., "Fabrication of topologically complex three-dimensional microfluidic systems in PDMS by rapid prototyping," *Analytical Chemistry*, 72: 3158-3164 (2000).
Andersson, et at., "TV sherography: quantitative measurement of shear-magnitude fields by use of digital speckle photography," *Applied Optics*, 39: 2565 (2000).
Anonymous (1996-1997) CRC Handbook of Chemistry and Physics (Chemical Rubber Publishing Company, Boca Raton) 77th Ed.).
Anonymous (2001) The human genome. Unsung heroes. Science 291(5507): 1207.
Anuta, "Digital Registration of Multispectral Video Imagery," Society of Photooptical Instrumentation Engineers Journal, vol. 7:168 (1969).
Applicant Initiated Interview Summary (PTOL-413) dated Dec. 2, 2013 for U.S. Appl. No. 13/157,803, filed Jun. 10, 2011 (Applicant—Vanderbilt University // Inventors—Bornhop et al.) (3 pages).
Applicant Initiated interview Summary (PTOL-413) dated Jul. 23, 2012 for U.S. Appl. No. 12/655,899, filed Jan. 8, 2010 (Applicant—Vanderbilt University // Inventors—Weinberger et al.) (3 pages).
Applicant Initiated Interview Summary (PTOL-413) dated Sep. 22, 2011 for U.S. Appl. No. 12/331,354, filed Dec. 9, 2008(Applicant—Vanderbilt University // Inventors—Bornhop et al.) (3 pages).
Arnold F, et al., "Directed Enzyme Evolution," *Meth Mol Biol*. 230 (2003).
Arnold FH, "Design by directed evolution," Accounts of Chemical Research, 31: 125-131 (1998).
Bachmann BO, et al., "Kinetic mechanism of the β-lactam synthetase of Streptomyces clavuligerus," *Biochemistry*, 39: 11187-11193 (2000).
Bachmann O, et al., "β-Lcatam synthetase: A new biosynthetic enzyme," *Proc. Nat. Acad. Sci. USA*. 1998; 95: 9082-6.
Baksh MM, et al., "Label-free quantification of membrane-ligand interactions using backscattering interferometry," *Nature Biotechnology*, 29: 357-360 (2011).
Baldino F, et al., "High-resolution in situ hybridization histochemistry," *Methods Enzymol*, 168: 761-777 (1989).
Betzig et al., (1993) Single Molecules Observed by near Field Scanning Optical Microscopy. Science 262(5138):1422-1425.
Bobbitt DR, et al., "Direct and Indirect Polarimetry for Detection in Micro bore Liquid Chromatography," Analytical Chemistry, 56: 1577-1581 (1984).
Boger, D.L. et al., Discovery of a Potent, Selective, and Efficacious Class of Reversible a-Ketoheterocycle Inhibitors of Fatty Acid Amide Hydrolase Effective as Analgesics. J Med Chem. 2005; 48(6):1849-56.
Bohren CF, et al., "Absoption and Scattering of Light by Small Particles," New York: Wiley (1983).
Borman S, "Combinatorial chemistry," Chemical & Engineering News, 80: 43 (2002).
Bornhop D.J. et al (2016) Elucidation of the signal origin for label-free, free-solution interactions, PNAS 113(34): E4931-E4932.
Swinney, K., et al., "Detection in Capillary Electrophoresis: A Review," *Electrophoresis*, 21: 1239-1250 (2000).
Bornhop DJ, et al., "Polarimetry in capillary dimensions," *Analytical Chemistry*, 68: 1677-1684 (1996).
Bornhop et al., Free-Solution, Label-Free Molecular Interactions Studief by Back-Scattering Interferometry. Science. 2007; 317(5845):1732-6.
Bornhop, "Microvolume index of refraction determinations by interferometric backscatter," Applied Optics, val. 34:3234-3239 (1995).

Bornhop, et al., "Free-Solution, Label-Free Molecular Interactions Studied by Back-Scattering Interferometry," Science, 317(5485):1732-6 (2007).
Bouchara, "Efficient algorithm for computation of the second-order moment of subpixel-edge position," Applied Optics, vol. 43:4550 (2004).
Bowen et al. (2003) "Gas phase detection of trinitrotoluene utilizing a solid-phase antibody immobilized on a gold film by means of surface plasmon resonance spectroscopy" Appl. Spectrosc. 57(8): 906-914.
Bracey, M.H. et al., Structural Adaptations in a Membrane Enzyme Thar Terminates Endocannabinoid Signaling. Science. 2002; 298(5599):1793-6.
Brawer, et al., "Screening for prostatic carcinoma with prostate specific antigen," J. Ural., 147:841-845 (1992).
Bray P, et al., "Human cDNA clones for four species of G Alpha s signal transduction protein," *Proc Natl Sci USA*, 83: 8893-8897 (1986).
Brenan, et al., "High throughput, nanoliter quantitative PCR," Drug Discovery Today: Tech, 2:247-253 (2005).
Brockhaus et al., "Thermadynamic studies on the interaction of antibodies with β-amyloid peptide," J Phys Chem B, 111:1238-1243 (2007).
Brockman et al., "A Multistep Chemical Modification Procedure to Create DNA Arrays on Gold Surfaces for the Study of Protein—DNA Interactions with Surface Plasmon Resonance Imaging," *J Am Chem Soc*, vol. 121 issue 35:8044-8051 (1999).
Burggraf N, et al., "Holographic Refractive Index Detector for Application in Microchip-based Separation Systems," *Analyst*, 123: 1443-1447 (1998).
Burke et al., "Stopped-flow enzyme assays on a chip using A microfabricated mixer," Anal Chem, 75(8):1786-1791 (2003).
Buynak JD, et al., "7-alkylidenecephalosporin esters as inhibitors of human leukocyte elastase," *J. Med. Chem.*, 40: 3423-3433 (1997).
Buynak JD, et al., "Synthesis and Mechanistic Evaluation of 7-Vinylidenecephem Sulfones as P-Lactamase Inhibitors," *J. Am. Chem. Soc.*, 116: 10955-10965 (1994).
Buynak JD, et al., "The Synthesis and β-Lactamase Inhibitory Activity of 6-(Carboxymethylene) Penicillins and 7-(Carboxymethylene) Cephalosporins," *Bioorg. Med. Chem. Lett.*, 5: 1513-1518 (1995).
Campitelli et al., "Shear horizontal surface acoustic wave based immunosensing system," *Int Conf on Solid State Sensors and Actuators*, Jun. 16-19, 1:187-190 (1997).
Cecchi, A. et al., Carbonic Anhydrase Inhibitors: Inhibition of the Human Isozymes I, II, VA, and IX with a Library of Substituted Difluoromethanesulfonamides. Bioorg med Chem Lett. 2005; 15(23):5192-6.
Choquette et al., "Wavenumber Standards for Near-infrared Spectrometry," Handbook of Vibrational Spectroscopy, John M. Chalmers and Peter R. Griffiths (Editors), 2002, p. 1-7.
Cohen N, et al., "In vitro enzyme evolution: the screening challenge of isolating the one in a million," *Trends in Biotechnology*, 19: 507-510.
Collignon et al., "Automated multimodality image registration based on information theory", Information Processing in Medical Imaging (Y. Bizais, C. Barillot and R. Di Paola, eds.), Kluwer Academic Publishers, Dordrecht, pp. 263-274, (1995).
Cravatt, B.F. et al., Chemical Characterization of a Family of Brain Lipids That Induce Sleep. Science. 1995; 268(5216):1506-9.
Crooke ST, et al., "Pharmacokinetic properties of several novel oligonucleotide analogs in mice," *J Pharmacol Exp Ther*, 277: 923-937 (1996).
Day, Y.S.N. et al., Direct Comparison of Binding Equilibrium, Thermodynamic, and Rate Constants Determined by Surface- and Solution-Based Biophysical Methods. Protein Sci. 2002; 11(5):1017-25.
DeGrandpre, "Measurement of seawater pCO2 using a renewable-reagent fiber optic sensor with colorimetric detection," *Anal. Chem.*, 65: 331-337 (1993).
Dendane et al., "Surface patterning of (bio)molecules onto the inner wall of fused-silica capillary tubes," *Lab Chip*, 8: 2161 (2008).

(56) References Cited

OTHER PUBLICATIONS

Deng Y, et al., "On-column Refractive-index detection Based on Retroreflected Beam Interference for Capillary Electrophoresis," *Applied Optics*, 37(6): 998-1005 (1998).
Devane, W.A. et al., Isolation and Structure of a Brain Constituent That Binds to the Cannabinoid Receptor. Science. 1992; 258(5090):1946-9.
Dickinson et al. (1996) A chemical-detecting system based on a crossreactive optical sensor array. Nature 382(6593):697-700.
Dissertation Defense Retrieved from http://calendar.vanderbilt.edu/calendar/2009/11/30/amanda-kathryn-kussrow-dissertation-defense. 95024 on Dec. 22, 2013 p. 1.
Ditchburn RW, "Light," Third Ed. Ed. New York: Academic Press (1976).
Dotson SS, et al., "Development of the Ultra Small Volume Polarimeter," Manuscript, Vanderbilt University, 1-11.
Duffy DC, et al., "Rapid Prototyping of Microfluidic Systems in Poly(dimethylsiloxane)," *Analytical Chemistry*, 70: 4974-4984 (1998).
Election and Preliminary Amendment filed Dec. 19, 2011 for U.S. Appl. No. 12/655,899, filed Jan. 8, 2010 (Applicant—Vanderbilt University // Inventors—Weinberger et al.) (5 pages).
Election Under Restriction Requirement filed Feb. 18, 2012 for U.S. Appl. No. 12/674,610, filed Oct. 4, 2011 (Applicant—Vanderbilt University // Inventors—Bornhop et al.) (10 pages).
Examiner-Initiated Interview Summary dated Nov. 3, 2011 for U.S. Appl. No. 11/666,046, filed Jul. 24, 2009 (Applicant—Vanderbilt University // Inventors—Bornhop et al.) (1 page).
Extended European Search Report dated Jun. 1, 2012 for European Pat. App.No. 05821243.2 filed Oct. 24, 2005 (Applicant—Vanderbilt University // Inventors—Bornhop et al.) (3 pages).
Extended European Search Report dated Oct. 19, 2012 for European Pat. App. No. 08755681.7 filed May 16, 2008 (Applicant—Vanderbilt Univeristy // Inventors—Jones et al.) (9 pages).
Fan, et al., "Electrochemical interrogation of conformational changes as a reagentless method for the sequence-specific detection of DNA" Proc Natl Acad Sci U S A, 100(16): 9134-9137 (2003).
Fasman et al. (1970) Conformational Changes Associated with F-1 HistoneDeoxyribonucleic Acid Complexes—Circular Dichroism Studies. Biochemistry 9(14):2814-2822.
Final Rejection dated Aug. 21, 2012 for U.S. Appl. No. 12/655,899, filed Jan. 8, 2010 (Applicant Vanderbilt University // Inventors—Weinberger et al.) (18 pages).
Final Rejection dated Aug. 22, 2013 for U.S. Appl. No. 13/157,803, filed Jun. 10, 2011 (Applicant—Vanderbilt University // Inventors—Bornhop et al.) (17 pages).
Final Rejection was dated Feb. 4, 2015 by the U.S. Patent and Trademark Office for U.S. Appl. No. 13/402,104, filed Feb. 22, 2012 and granted as U.S. Pat. No. 9,562,853 on Feb. 7, 2017 (Inventor—Darryl J. Bornhop et al.) (14 pages).
Final Rejection was dated Jun. 15, 2016 by the U.S. Patent and Trademark Office for U.S. Appl. No. 13/157,803, filed Jun. 10, 2011 and published as US 2012-0019834 A1 on Jan. 26, 2012 (Inventor—Darryl J. Bornhop; Applicant—Vanderbilt University) (19 Pages).
Final Rejection was dated Jun. 23, 2016 by the U.S. Patent and Trademark Office for U.S. Appl. No. 13/402,104, filed Feb. 22, 2012 and published as US-2013-0021608-A1 on Jan. 24, 2013 (Inventor—Darryl J. Bornhop; Applicant—Vanderbilt University) (11 pages).
Finn MG, "Emerging methods for the rapid determination of enantiomeric excess," *Chirality*, 14: 534-540 (2002).
Fintschenko Y, et al., "Silicon Microtechnology and Microstructures in Separation Science," *Journal of Chromatography A*, 819: 3-12 (1998).
Fixman, M. (1962) Radius of Gyration of Polymer Chains. II. Segment Density and Excluded Volume Effects. The Journal of Chemical Physics 36(12):3123-3129.
Fox SJ, et al., "Assay Innovations Vital to Improving HTS," *Drug Discovery and Development*, 40-43 (2000).
Fredrickson, C.K. and Fan, Z.H., Macro-to-Micro Interfaces for Microfluidic Devices. Lab Chip. 2004; 4(6):526-33.

Fricke-Begemann et al., "Speckle interferometry: three-dimensional deformation field measurement with a single interferogram," Applied Optics, vol. 40:5011 (2001).
Froestl, W. et al., Phosphinic Acid Analogs of GABA. 1. New Potent and Selective GABAB Agonists. J Med Chem. 1995; 38(17):3297-312.
Garfunkle, J. et al., Optimization of the Central Heterocycle of a-Ketoheterocycle Inhibitors of Fatty Acid Amide Hydrolase. J Med Chem. 2008; 51(15):4392-403.
Gavutis, et al., "Lateral ligand-receptor interaction on membranes probed by simultaneous fluorescence-interference detection," *Biophysics Journal*, 88(6): 4289-4302 (2005).
Gharagheizi et al. (2014) Group Contribution Model for the Prediction of Refractive Indices of Organic Compounds. J Chem Eng Data 59(6): 1930-1943.
Gibbs PR, et al., "Imaging polarimetry for high throughput chiral screening," *Biotechnology Progress*, 19: 1329-1334 (2003).
Gloge A, et al., "The behavior of substrate analogues and secondary deuterium isotope effects in the phenylalanine ammonia-lyase reaction," *Archives of Biochemistry and Biophysics*, 359: 1-7 (1998).
Golge A, et al., "Phenylalanine ammonia-lyase: The use of its broad substrate specificity for mechanistic investigations and biocatalysis—Synthesis of Larylalanines," *Chemistry—a European Journal*, 6: 3386-3390 (2000).
Grant CHE 0848788 awarded by the National Science Foundation.
Grant No. F49620-01-1-0429.
Grant No. R01 EB003537-01A2 awarded by National Institutes of Health.
Greisen, et al., "PCR primers and probes for the 16S rRNA gene of most species of pathogenic bacteria, including bacteria found in cerebrospinal fluid," J Clin Microbiol, 32:335-351 (1994).
Grosberg and Khokhlov (1994) Statistical Physics of Macromolecules American Institute of Physics, New York.
Grosse A, et al., "Deep wet etching of fused silica glass for hollow capillary optical leaky waveguides in microfluidic devices," *Journal of Micromechanics and Microengineering*, 11: 257-262 (2001).
Guizar-Sicairos et al., "Efficient subpixel image registration algorithms," Optics Letters, vol. 33:156-158 (2008).
Guo JH, et al., "Measurement of enantiomeric excess by kinetic resolution and mass spectrometry," *Angewandte Chemie-International Edition*, 38: 1755-1758 (1999).
Harrison DJ, et al., "Capillary Electrophoresis and Sample Injection Systems Integrated on a Planar Glass Chip," *Analytical Chemistry*, 64: 1926-1932 (1992).
Harteveld et al., "Detection of Staphylococcal Enterotoxin B employing a piezoelectric crystal immunosensor," *Biosens Bioelectron* 12(7):661-667 (1997).
Hecht E, "Optics," New York: Addison-Wesley Longman (1998).
Heideman et al. (1993) Performance of a highly sensitive optical wave-guide Mach-Zehnder interferometer immunosensor, Sensors and Actuators B-Chemical 10(3): 209-217.
Heideman, et al., "Remote opto-chemical sensing with extreme sensitivity: design, fabrication and performance of a pigtailed integrated optical phase-modulated Mach-Zehnder interferometer system," *Sensors and Actuators*, B 61: 100-127 (1999).
Heikkinen H, et al., "Interpretation of interference signals in label free integrated interferometric biosensors," *Proceedings of the SPIE*, 6094: 60940P-1 (2006).
Hell SW & Wichmann J (1994) Breaking the diffraction resolution limit by stimulated emission: stimulated-emission-depletion fluorescence microscopy. Opt Lett 19(11):780-782).
Hodgins DS, "Yeast Phenylalanine Ammonia-Lyase—Purification, Properties, and Identification of Catalytically Essential Dehydroalanine," Journal of Biological Chemistry, 246: 2977 (1971).
Hofstetter O, et al., "Antibodies as chiral selectors for the determination of enantioenrichment," *Enantiomer*, 6: 153-158 (2001).
Horton et al., "Interference patterns of a plane-polarized wave from a hollow glass fiber," *J Opt Soc Am*, 63:1204-1210 (1973).
Hu et al. (2004) The mode of action of centrin—Binding of Ca2+ and a peptide fragment of Kar1p to the C-terminal domain. J Biol Chem 279(49):50895-50903.
Hubbard et al., "Calmodulin binding by calcineurin," *J Biol Chem* 262(31):15062-15070 (1987).

(56) References Cited

OTHER PUBLICATIONS

Hudlicky TM, et al., "Microbial Oxidation of Aromatics in Enantiocontrolled Synthesis .1. Expedient and General AsymmetricSynthesis of Inositols and Carbohydrates via an Unusual Oxidation of a Polarized Diene with Potassium Permanganate," *J. Chem. Soc. Perkin Trans.*, 1: 1553-1567.

Huntley, "Speckle photography fringe analysis: assessment of current algorithms," Applied Optics, vol. 28:4316 (1989).

International Preliminary Examination Report dated Nov. 28, 2001 for PCT/US2000/020783 filed Aug. 17, 2000 and published as WO 2001/014858 on Mar. 1, 2001 (Applicant—Texas Tech University Health Sciences Center // Inventors—Bornhop et al.) (5 pages).

International Preliminary Report on Patentability dated Mar. 24, 2010 for PCT/US2008/077145 filed Sep. 20, 2008 and published as WO 2009/039466 on Mar. 26, 2009 (Applicant—Vanderbilt University // Inventors—Bornhop et al.) (9 pages).

International Preliminary Report on Patentability dated Apr. 16, 2013 for PCT/US2011/056171 filed Oct. 13, 2011 and published as WO 2012/051429 on Apr. 19, 2012 (Applicants—Vanderbilt University // Inventors—Bornhop et al.) (7 pages).

International Preliminary Report on Patentability dated Jul. 12, 2011 for PCT/US2010/000047 filed Jan. 8, 2010 and published as WO 2010/080710 on Jul. 15, 2010 (Applicants—Molecular Sensing, Inc. et al. // Inventors—Weinberger et al.) (5 pages).

International Preliminary Report on Patentability dated Nov. 24, 2009 for US/PCT/2008/063879 filed May 16, 2008 and published as WO 2008/144496 on Nov. 27, 2008 (Applicant—Vanderbilt University // Inventors—Jones et al.) (10 pages).

International Preliminary Report on Patentability dated Dec. 14, 2012 for PCT/US2011/039982 filed Jun. 10, 2011 and published as WO 2011/156713 on Dec. 15, 2011 (Applicants—Vanderbilt University // Inventors—Bornhop et al.) (5 pages).

International Preliminary Report on Patentability dated Apr. 24, 2007 for PCT/US2005/38168 filed Oct. 24, 2005 and published as WO 2006/047408 on May 4, 2006 (Applicants—Vanderbilt University // Inventors—Bornhop et al.) (6 pages).

International Preliminary Report on Patentability dated Jul. 25, 2017 by the International Searching Authority for Patent Application No. PCT/US2016/014439, which was filed on Jan. 22, 2016 and published as WO 2016/118812 on Jul. 28, 2016 (Inventor—Bornhop et al.; Applicant—Vanderbilt University) (8 pages).

International Search Report and Written Opinion dated Mar. 8, 2012 for PCT/US2011/056171 filed Oct. 13, 2011 and published as WO 2012/051429 on Apr. 19, 2012 (Applicants—Vanderbilt University // Inventors—Bornhop et al.) (8 pages).

International Search Report and Written Opinion dated Aug. 19, 2008 for US/PCT/2008/063879 filed May 16, 2008 and published as WO 2008/144496 on Nov. 27, 2008 (Applicant—Vanderbilt University // Inventors—Jones et al.) (11 pages).

International Search Report and Written Opinion dated Sep. 30, 2010 for PCT/US2010/000047 filed Jan. 8, 2010 and published as WO 2010/080710 on Jul. 15, 2010 (Applicants—Molecular Sensing, Inc. et al. // Inventors—Weinberger et al.) (7 pages).

International Search Report and Written Opinion dated Oct. 5, 2011 for PCT/US2011/039982 filed Jun. 10, 2011 and published as WO 2011/156713 on Dec. 15, 2011 (Applicants—Vanderbilt University // Inventors—Bornhop et al.) (6 pages).

International Search Report and Written Opinion dated Dec. 8, 2008 for PCT/US2008/077145 filed Sep. 20, 2008 and published as WO 2009/039466 on Mar. 26, 2009 (Applicant—Vanderbilt University // Inventors—Bornhop et al.) (9 pages).

International Search Report and Written Opinion dated Apr. 26, 2006 for PCT/US2005/038168 filed Oct. 24, 2005 and published as WO 2006/047408 on May 4, 2006 (Applicants—Vanderbilt University // Inventors—Bornhop et al.) (7 pages).

International Search Report and Written Opinion dated Mar. 24, 2016 by the International Searching Authority for Patent Application No. PCT/US2016/014439, which was filed on Jan. 22, 2016 and published as WO 2016/118812 on Jul. 28, 2016 (Inventor—Bornhop et al.; Applicant—Vanderbilt University) (9 pages).

International Search Report and Written Opinion were dated May 25, 2017 by the International Searching Authority for International Application No. PCT/US2017/015296, which was filed on Jan. 27, 2017 (Applicant—Vanderbilt University) (10 pages).

Issue Notification dated Feb. 1, 2012 for U.S. Appl. No. 12/331,354, filed Dec. 9, 2008 (Applicant—Vanderbilt University // Inventors—Bornhop et al.) (1 page).

Issue Notification dated Feb. 22, 2012 for U.S. Appl. No. 11/666,046, filed Jul. 24, 2009 (Applicant—Vanderbilt University // Inventors—Bornhop et al.) (1 page).

Issue Notification dated Apr. 5, 2013 for U.S. Appl. No. 12/674,610, filed Oct. 4, 2011 (Applicant—Vanderbilt University // Inventors—Bornhop et al.) (1 page).

Issue Notification dated Oct. 27, 2010 for U.S. Appl. No. 12/122,175, filed May 16, 2008 (Applicant—Vanderbilt University // Inventors—Jones et al.) (1 page).

Issue Notification was dated Jan. 18, 2017 by the U.S. Patent and Trademark Office for U.S. Appl. No. 13/402,104, filed Feb. 22, 2012 and granted as U.S. Pat. No. 9,562,853 on Feb. 7, 2017 (Inventor—Darryl J. Bornhop et al.) (1 page).

Issue Notification was dated Feb. 10, 2016 by the U.S. Patent and Trademark Office for U.S. Appl. No. 13/892,642, filed May 13, 2013 and granted as U.S. Pat. No. 9,273,949 on Mar. 1, 2016 (Inventor—Darryl J. Bornhop et al.) (1 page).

Issue Notification was dated Apr. 12, 2017 by the U.S. Patent and Trademark Office for U.S. Appl. No. 13/157,803, filed Jun. 10, 2011 and granted as U.S. Pat. No. 9,638,632 on May 2, 2017 (Inventor—Darryl J. Bornhop et al.) (1 page).

Ivanov et al. (1974) The B to A transition of DNA in solution. J Mol Biol87(4):817-833.

Jacobson SC, et al., "Fused Quartz Substrates for Microchip Electrophoresis," *Analytical Chemistry*, 67: 2059-2063 (1995).

Jacobson SC, et al., "Microfluidic devices for electrokinetically driven parallel and serial mixing," *Analytical Chemistry*, 71: 4455-4459 (1999).

Jass, J. et al., From Liposomes to Supported, Planar Bilayer Structures on Hydrophilic and Hidrophobic Surfaces: an Atomic Force Microscopy Study. Biophys J. 2000; 79(6):3153-63.

Jepsen et al. (2015) Evaluation of back scatter interferometry, a method for detecting protein binding in solution. Analyst 140(3):895-901.

Jepsen S.T. (2016) Back Scatter Interferometric Sensor for Label-Free Medical Diagnostic Assays, Aalborg University (1-120 pages).

Jepsen S.T. et al, (2015) Evaluation of back scatter interferometry, a method for detecting protein binding in solution, Analyst, 140(3):895-901.

Jorgensen T.M. et al (2015) Back scattering interferometry revisited—A theoretical and experimental investigation, Sensors and Actuators B 220 : 1328-1337.

Jung LS, et al., (1998) Quantitative Interpretation of the Response of Surface Plasmon Resonance Sensors to Adsorbed Films. Langmuir 14(19):5636-5648).

Kabanov AV, et al., "A new class of antivirals: antisense oligonucleotides combined with a hydrophobic substituent effectively inhibit influenza virus reproduction and synthesis of virus-specific proteins in MDCK cells," *FEBS Letters*, 259(2): 327-330 (1990).

Kalghatgi KK, et al., "Microbial L-phenylalanine ammonia-lyase. Purification, subunit structure and kinetic properties of the enzyme from Rhizoctonia sol ani," *Biochemical Journal*, 149: 65-75 (1975).

Kalinina, et al., "Nanoliter scale PCR with TaqMan detection," *Nucleic Acid Research*, 25(10):1999-2004 (1997).

Kaltashov et al. (2012) Advances and challenges in analytical characterization of biotechnology products: Mass spectrometry-based approaches to study properties and behavior of protein therapeutics. Biotechnol Adv 30(1):210-222.

Katritzky et al. (1998) Correlation and prediction of the refractive indices of polymers by QSPR. J Chem Inf Comp Sci 38(6): 1171-1176.

Kaupmann, K. et al., Expression Cloning of GABAB Receptors Uncovers Similarity to Metabotropic Gultamate Receptors. Nature. 1997; 386(6622):239-46.

Keen et al., "Rapid detection of single base mismatches as heteroduplexes on Hydrolilnk gels," Trends Genet., 7:5 (1991).

(56) References Cited

OTHER PUBLICATIONS

Kenmore CK, et al., "Refractive-index Detection by interferometric Backscatter in Packed-capillary High-performance Liquid Chromatography," *Journal of Chromatography A*, 762: 219-225 (1997).

Kerker M, et al., "Scattering of Electomagnetic Waves from Concentric Infinite Cylinders, "Journal of the Optical Society of Americai,51: 506-508 (1961).

Buynak, J.D., et al., "Synthesis and Biological-Activity of 7-Alkylidenecephems," *J. Med. Chem.*, 38: 1022-1034 (1995).

Klee et al., "Purification of cyclic 3',5'-nucleotide phosphodiesterase inhibitory protein by affinity chromatography on activator protein couples to sepharose," Biochem 17:120-126 (1978).

Koradi et al. (1996) MOLMOL: A program for display and analysis of macromolecular structures. J Mol Graphics 14(1 ):51-55.

Korbel GA, et al., "Reaction microarrays: A method for rapidly determining the enantiomeric excess of thousands of samples," *Journal of the American Chemical Society*, 123: 361-362.

Krummel, M.F. and Davis, M.M., Dynamics of the Immunological Synapse: Finding, Establishing and Solidifying a Connection. Curr Opin Immunol. 2002; 14(1):66-74.

Kuhlmann J, "Drug Research: From the Idea to the Product," *International Journal of Clinical Pharmacology and Therapeutics*, 541-552 (1997).

Kunkel TA, et al., "Rapid and efficient site-specific mutagenesis without phenotypic selection," *Methods Enzymol*, 154: 367-382 (1987).

Kussrow A, et al., "Measurement of Mono- and Polyvalent Carbohydrate-Lectin Binding by Back-Scattering Interferometry," Anal. Chem., 81: 4889-4897 (2009).

Kussrow et al. (2009) Measurement of Monovalent and Polyvalent Carbohydrate-Lectin Binding by Back-Scattering Interferometry. Anal Chem 81(12):4889-4897.

Kussrow et al. (2012) Interferometric Methods for Label-Free Molecular Interaction Studies. Anal Chem 84(2):779-792.

Kussrow, "Interogation of Biomolecular Interactions Utilizing Backscattering Interferometry," Dissertation, Vanderbilt University (2009), pp. i-xii and 1-115 (127 pages total), retrieved from http://etd.library.vanderbilt.edu/available/etd-12042009-092927 on Apr. 29, 2013.

Kussrow, A. et al, Measurement of Mono- and Polyvalent Carbohydrate-Lectin Binding by Back-Scattering Interferometry. Anal Chem. 2009; 81(12):4889-97.

Kussrow, A. et al., Universal Sensing by Transduction of Antibody Binding with Backscattering Interferometry. Chembiochem. 2011; 12(3):367-70.

Kypr et al. (2009) Circular dichroism and conformational polymorphism of DNA Nucleic Acids Res 37( 6): 1713-1725.

Lan et al., "Non-mechanical sub-pixel image shifter for acquiring super-resolution digital images," Optics Express, vol. 17:22992-23002 (2009).

Langone, "Protein A of *Staphylococcus aureus* and related immunoglobulin receptors produced by streptococci and pneumonococci," *Adv Immunol*, 32:157-252 (1982).

Latham et al., "Photobiotin surface chemistry improves label-free interferometric sensing of biochemical interactions," *Angew Chem Int Ed*, 45:955-958 (2006).

Leslie and Lilley (1985) Aqueous solutions containing amino acids and peptides. Part 20. Volumetric behavior of some terminally substituted amino acids and peptides at 298.15 K. Biopolymers 24(4):695-710.

Letsinger, et al., "Cholesteryl-conjugated oligonucleotides: Synthesis, properties, and activity as inhibitors of replication of human immunodeficiency virus in cell culture," Proc. Natl. Acad. Sci. USA, 86: 6553-6556 (1989).

Levene et al. (2003) Zero-mode waveguides for single-molecule analysis at high concentrations. Science 299(5607):682-686).

Liang, Y. (2006) Applications of isothermal titration calorimetry in protein folding and molecular recognition. J Iran Chem Soc 3(3):209-219.

Liedberg et al. (1995) Biosensing with Surface-Plasmon Resonance—How It All Started. Biosens Bioelectron 10(8):R1-R9.

Liu SR, et al., "Optimization of high-speed DNA sequencing on microfabricated capillary electrophoresis channels," Analytical Chemistry, 71: 566-573 (1999).

Lodish et al. (1990) Molecular Cell Biology (Scientific American Books, New York).

Malacara D, et al., "Interferogram Analysis for Optical Testing," New York: Marcel Dekker, Inc (1998).

Manoharan M, et al., "Chemical modifications to improve uptake, and bioavailability of antisense oligonucleotides," *Ann. NY Acad. Sci.*, 660: 306-309 (1992).

Manoharan M, et al., "Cholic acid-oligonucleotide conjugates for antisense applications," *Biorg. Med. Chem. Lett.*, 4: 1053-1060 (1994).

Manoharan M, et al., "Introduction of a Lipophilic Thioether Tether in the Minor Groove of Nucleic Acids for Antisense Applications," *Bioorg. Med. Chem. Lett.*, 3: 2765-2770 (1993).

Manoharan M, et al., "Lipidic nucleic acids," *Tetrahedron Lett.*, 36: 3651-3654 (1995).

Manoharan M, et al., "Oligonucleotide conjugates: alteration of the pharmacokinetic properties of antisense agents," *Nucleosides & Nucleotides*, 14: 969-973 (1995).

Manz A, et al., "Micromachining of Monocrystalline Silicon and Glass for Chemical-Analysis Systems—a Look into Next Century Technology or Just a Fashionable Craze," Trac-Trends in Analytical Chemistry, 10: 144-149 (1991).

Manz A, et al., "Miniaturized Total Chemical-Analysis Systems—a Novel Concept for Chemical Sensing," *Sensors and Actuators B—Chemical*, 1: 244-248 (1990).

Marcuse et al., "Light scattering from optical fibers with arbitrary refractive-index distributions," J Opt Soc Am, 65:367-375 (1975).

Marketwired, "Molecular Sensing, Inc. and VIB Enter Agreement in Alzheimer's Disease Research." Internet Publication http://www.marketwired.com/press-release/molecular-sensing-inc-and-vib-enter-agreement-in-alzheimers-disease-research-1231768.htm (2009).

Markov D, et al., "A Fourier Analysis Approach for Capillary Polarimetry," *Electrophoresis*, 23(5): 809-812 (2002).

Markov D, et al., "Breaking the 10-7 Barrier for RI Measurements in Nanoliter Volumes," *Analytical Chemistry*, 74: 5438-5441 (2002).

Markov D, et al., "Nanoliter-scale Non-invasive Flow-Rate Quantification using Micro-Interferometric Backscatter and Phase Detection," *Fresenius' Journal of Analytical Chemistry*, 371: 234-237 (2001).

Markov DA, et al., "Non-Invasive Fluid Flow Measurements in Microfluidic Channels with Backscatter Interferometry," Submitted to Electrophoresis 2004.

Markov et al., "Label-Free Molecular Interaction Determinations with Nanoscale Interferometry," J Am Chem Soc 126:16659-16664 (2004).

Marsh and Teichmann (2011) Relative Solvent Accessible Surface Area Predicts Protein Conformational Changes upon Binding. Structure 19(6):859-867.

Martynova L, et al., "Fabrication of plastic micro fluid channels by imprinting methods," *Analytical Chemistry*, 69: 4782-4789 (1997).

Mathworks, "Registering an Image Using Normalized Cross-Correlation," http://www.mathworks.com/products/demos/image/cross-correlation/imreg.html, last accessed May 15, 2014.

May O, et al., "Inverting enantioselectivity by directed evolution of hydantoinase for improved production ofL-methionine," Nature Biotechnology, 18: 317-320 (2000).

Maystre F, et al., "Enhanced Polarimetric Detection in Hplc Using a Refractive-Index Equalizer," *Analytical Chemistry*, 66: 2882-2887 (1994).

Miller MT, et al., "Structure of β-lactam synthetase reveals how to synthesize antibiotics instead of asparagine," *Nature Struct. Biol.*, 8: 684-689 (2001).

Miller MT, et al., "The catalytic cycle of β-lactam synthetase observed by x-ray crystallographic snapshots," *Proc. Nat. Acad. Sci. USA*, 99: 14752-14757 (2002).

Minor, L.K., Label-Free Cell-Based Functional Assays. Comb Chem High Throughput Screen. 2008; 11(7):573-80.

Miroshnikova et al., "Percussion hole drilling of metals with a fourth-harmonic Nd:YAG laser studied by defocused laser speckle correlation," Applied Optics, vol. 44:3403 (2005).

(56) References Cited

OTHER PUBLICATIONS

Mishra RK, et al., "Improved leishmanicidal effect of phosphorotioate antisense oligonucleotides by LDL-mediated delivery," *Biochim Biophys Acta*, 1264: 229-327 (1995).
Molphy et al., "Surface Modification of Kaolin. 1. Covalent Attachement of Polyethylene Glycol using a Urethane Linker," *Polymer International*, 34: 425-431 (1994).
Montigiani et al., "Alanine substitutions on calmodulin-binding peptides result in unexpected affinity enhancement," *J Mol Biol* 258:6-13 (1996).
Morcos, E.F. et al., Free-Solution Interaction Assay of Carbonic Anhydrase to Its Inhibitors Using Back-Scattering Interferometry. Electrophoresis. 2010; 31(22):3691-5.
Moreira et al. (2005) Effects of fluorescent dyes, quenchers, and dangling ends on DNA duplex stability. Biochem Bioph Res Co 327(2):473-484.
Morrison, et al., "Nanoliter high throughput quantitative PCR," Nucleic Acid Res, 34(18):e123 (2004).
Neifeld, "Information, resolution, and space-bandwidth product," Optics Letters, vol. 23:1477-1479 (1998).
Nielson PE, et al., "Sequence-selective recognition of DNA by strand displacement with a thymine-substituted polyamide," *Science*, 254: 1497-1500 (1991).
Non Final Rejection was dated Mar. 2, 2015 by the U.S. Patent and Trademark Office for U.S. Appl. No. 13/892,642, filed May 13, 2013 and granted as U.S. Pat. No. 9,273,949 on Mar. 1, 2016 (Inventor—Darryl J. Bornhop et al.) (12 pages).
Non Final Rejection was dated Jul. 3, 2017 by the USPTO for U.S. Appl. No. 13/879,523, filed Jun. 28, 2013 and published as US 2013-0280715 A1 on Oct. 24, 2013 (Inventor—Darryl J. Bornhop)(13 pages).
Non Final Rejection was dated Aug. 21, 2015 by the U.S. Patent and Trademark Office for U.S. Appl. No. 13/402,104, filed Feb. 22, 2012 and granted as U.S. Pat. No. 9,562,853 on Feb. 7, 2017 (Inventor—Darryl J. Bornhop et al.) (11 pages).
Non-Final Rejection dated Jan. 2, 2014 for U.S. Appl. No. 13/409,557, filed Mar. 1, 2012 (Applicant—Vanderbilt University // Inventors—Bornhop et al.) (35 pages).
Non-Final Rejection dated Feb. 21, 2012 for U.S. Appl. No. 12/655,899, filed Jan. 8, 2010 (Applicant—Vanderbilt University // Inventors—Weinberger et al.) (20 pages).
Non-Final Rejection dated Mar. 19, 2013 for U.S. Appl. No. 13/157,803, filed Jun. 10, 2011 (Applicant—Vanderbilt University // Inventors—Bornhop et al.) (16 pages).
Non-Final Rejection dated May 6, 2013 for U.S. Appl. No. 13/409,557 filed Mar. 1, 2012 (Applicant—Vanderbilt University // Inventors—Bornhop et al.) (19 pages).
Non-Final Rejection dated May 13, 2014 for U.S. Appl. No. 13/402,104, filed Feb. 22, 2012 (Applicant—Vanderbilt University // Inventors—Bornhop et al.) (11 pages).
Non-Final Rejection dated Jun. 7, 2012 for U.S. Appl. No. 12/674,610, filed Oct. 4, 2011 (Applicant—Vanderbilt University // Inventors—Bornhop et al.) (21 pages).
Non-Final Rejection dated Jul. 23, 2014 for U.S. Appl. No. 13/157,803, filed Jun. 10, 2011 (Applicant—Vanderbilt University // Inventors—Bornhop et al.) (17 pages).
Non-Final Rejection dated Oct. 2, 2012 for U.S. Appl. No. 13/157,803, filed Jun. 10, 2011 (Applicant—Vanderbilt University // Inventors—Bornhop et al.) (17 pages).
Non-Final Rejection dated Nov. 23, 2015 for U.S. Appl. No. 13/157,803, filed Jun. 10, 2011 (Applicant—Vanderbilt University II Inventors—Bornhop et al.) (18 pages).
Non-Final Rejection dated Mar. 24, 2011 for U.S. Appl. No. 12/331,354, filed Dec. 28, 2008 (Applicant—Vanderbilt University // Inventors—Bornhop et al.) (15 pages).
Non-Final Rejection dated Apr. 28, 2010 for U.S. Appl. No. 12/122,175, filed May 16, 2008 (Applicant—Vanderbilt University // Inventors—Jones et al.) (18 pages).
Non-Final Rejection dated Jun. 29, 2010 for U.S. Appl. No. 12/122,175, filed May 16, 2008 (Applicant—Vanderbilt University // Inventors—Jones et al.) (18 pages).
Non-Final Rejection dated Jul. 8, 2003 for U.S. Appl. No. 10/053,877, filed Jan. 24, 2002 (Applicant—Vanderbilt University // Inventors—Bornhop et al.) (6 pages).
Notice of Allowance dated Mar. 20, 2013 for U.S. Appl. No. 12/674,610, filed Oct. 4, 2011 (Applicant—Vanderbilt University // Inventors—Bornhop et al.) (10 pages).
Notice of Allowance dated Jul. 22, 2010 for U.S. Appl. No. 12/122,175, filed May 16, 2008 (Applicant—Vanderbilt University // Inventors—Jones et al.) (7 pages).
Notice of Allowance dated Sep. 10, 2010 for U.S Appl. No. 12/122,175, filed May 16, 2008 (Applicant—Vanderbilt University // Inventors—Jones et al.) (4 pages).
Notice of Allowance dated Oct. 11, 2011 for U.S. Appl. No. 12/331,354, filed Dec. 9, 2008 (Applicant—Vanderbilt University // Inventors—Bornhop et al.) (7 pages).
Notice of Allowance dated Nov. 3, 2011 for U.S. Appl. No. 11/666,046, filed Jul. 24, 2009 (Applicant—Vanderbilt University // Inventors—Bornhop et al.) (8 pages).
Notice of Allowance dated May 28, 2004 for U.S. Appl. No. 10/053,877, filed Jan. 24, 2002 (Applicant—Vanderbilt University // Inventors—Bornhop et al.) (7 pages).
Notice of Allowance dated Nov. 20, 2003 for U.S. Appl. No. 10/053,877, filed Jan. 24, 2002 (Applicant—Vanderbilt University // Inventors—Bornhop et al.) (7 pages).
Notice of Allowance was dated Oct. 11, 2016 by the U.S. Patent and Trademark Office for U.S. Appl. No. 13/402,104, filed Feb. 22, 2012 and granted as U.S. Pat. No. 9,562,853 on Feb. 7, 2017 (Inventor—Darryl J. Bornhop et al.) (9 pages).
Notice of Allowance was dated Oct. 30, 2015 by the U.S. Patent and Trademark Office for U.S. Appl. No. 13/892,642, filed May 13, 2013 and granted as U.S. Pat. No. 9,273,949 on Mar. 1, 2016 (Inventor—Darryl J. Bornhop et al.) (8 pages).
Notice of Allowance was dated Oct. 31, 2016 by the U.S. Patent and Trademark Office for U.S. Appl. No. 13/157,803, filed Jun. 10, 2011 and granted as U.S. Pat. No. 9,638,632 on May 2, 2017 (Inventor—Darryl J. Bornhop et al.) (12 pages).
Oberhauser B, et al, "Effective incorporation of 2'-O-methyl-obligoribonucleotides into liposomes and enhanced cell association through modification with thiocholesterol," *Nucleic Acids Research*, 20(3): 533-538 (1992).
Olmsted et al. (2014) Toward Rapid, High-Sensitivity, Volume-Constrained Biomarker Quantification and Validation using.
Olmsted, I.R. et al., Comparison of Free-solution and Surface-Immobilized Molecular Interactions Using a Single Platform, Back-Scattering Interferometry. Anal Chem. 2012; 84(24):10817-22.
Orita et al., "Rapid and sensitive detection of point mutations and DNA polymorphisms using the polymerase chain reaction," Genomics, 5:874-879 (1989).
Overington, J.P. et al., How Many Drug Targets Are There? Nat Rev Drug Discov. 2006; 5(12):993-6.
Papalia, G.A. et al., Comparative Anaylsis of 10 Small Molecules Binding to Carbonic Anhydrase II by Different Investigators Using Biacore Technology. Anal Biochem. 2006; 359(1):94-105.
PDR-Chiral, Development of a New Laser Based Polarimetric Detector and Its Application to High-performance Liquid Chromatography, *HPLC* (1998).
Persson et al., "Lipid-Based Passivation in Nanofluidics," *Nano Letters*, 12: 2260-2265 (2012).
Pesciotta et al. (2011) Back-Scattering Interferometry: A Versatile Platform for the Study of Free-Solution versus Surface-Immobilized Hybridization. Chemistry—an Asian Journal 6(1 ): 70-73.
Pettersen et al. (2004) UCSF chimera—A visualization system for exploratory research and analysis. J Comput Chem 25(13): 1605-1612).
Pin, J.P. et al., Activation Mechanism of the Heterodimeric GABAB Receptor. Biochem Pharmacol. 2005; 68(8):1565-72.
Pitter et al., "Focus errors and their correction in microscopic deformation analysis using correlation," Optics Express, vol. 10:1361-1367 (2002).

(56) References Cited

OTHER PUBLICATIONS

Porat B, "A Course in Digital Signal Processing," New York: Wiley and Sons (1997).
Preliminary Amendment filed Apr. 15, 2013 for U.S. Appl. No. 13/879,523, filed Jun. 28, 2013 (Applicant—Vanderbilt University // Inventors—Bornhop et al.) (7 pages).
Preliminary Amendment filed Jun. 5, 2009 for U.S. Appl. No. 12/331,354, filed Dec. 9, 2008 (Applicant—Vanderbilt University // Inventors—Bornhop et al.) (4 pages).
Preliminary Amendment filed Jul. 12, 2010 for U.S. Appl. No. 12/655,899, filed Jan. 8, 2010 (Applicant—Vanderbilt University // Inventors—Weinberger et al.) (2 pages).
Preliminary Amendment filed Oct. 4, 2011 for U.S. Appl. No. 12/674,610, filed Oct. 4, 2011 (Applicant—Vanderbilt University // Inventors—Bornhop et al.) (9 pages).
Project et al. (2006) A molecular dynamics study of the effect of Ca2+ removal on calmodulin structure. Biophys J 90(11): 3842-3850.
Qian et al. (1997) Characterization of antigen-antibody complexes by size-exclusion chromatography coupled with low-angle light-scattering photometry and viscometry. J Chromatogr A 787(1-2): 101-109.
Quake SR, et al., "From micro- to nanofabrication with soft materials," *Science*, 290: 1536-1540 (2000).
Read, et al., "Aseptic meningitis and encephalitis: the role of PCR in the diagnostic laboratory," Clin Microbiol, 35:691-696 (1997).
Reem et al, "Induction and upregulation by interleukin 2 of high-affinity interleukin 2 receptors on thymocytes and T cells," Proc Natl Acad Sci USA, 82:8663-8666 (1985).
Reetz MT, "Combinatorial and evolution-based methods in the creation of enantioselective catalysts," *Angewandte Chemie—International Edition*, 40: 284-310 (2001).
Reetz MT, "New methods for the high-throughput screening of enantioselective catalysts and biocatalysts," *Angewandte Chemie—International Edition*, 41: 1335-1338 (2002).
Response to Office Action filed Feb. 4, 2013 for U.S. Appl. No. 13/157,803, filed Jun. 10, 2011 (Applicant—Vanderbilt University // Inventors—Bornhop et al.) (10 pages).
Request for Continued Examination filed on Jan. 22, 2014 for U.S. Appl. No. 13/157,803, filed Jun. 10, 2011 (Applicant—Vanderbilt University // Inventors—Bornhop et al.) (15 pages).
Requirement for Restriction/Election dated Oct. 18, 2011 for U.S. Appl. No. 12/655,899, filed Jan. 8, 2010 (Applicant—Vanderbilt University // Inventors—Weinberger et al.) (10 pages).
Requirement for Restriction/Election dated Dec. 19, 2011 for U.S. Appl. No. 12/674,610, filed Oct. 4, 2011 (Applicant—Vanderbilt University // Inventors—Bornhop et al.) (12 pages).
Requirement for Restriction/Election dated Dec. 28, 2010 for U.S. Appl. No. 12/331,354, filed Dec. 9, 2008 (Applicant—Vanderbilt University // Inventors—Bornhop et al.) (12 pages).
Resetar S, et al., "Anticipating Technological Change: Combinatorial Chemistry and the Environment," *EPA* (2001).
Response to Final Office action filed Jan. 22, 2014 for U.S. Appl. No. 13/157,803, filed Jun. 10, 2011 (Applicant—Vanderbilt University // Inventors—Bornhop et al.) (12 pages).
Response to Final Office action filed Oct. 23, 2014 for U.S. Appl. No. 13/157,803, filed Jun. 10, 2011 (Applicant—Vanderbilt University // Inventors—Bornhop et al.) (12 pages).
Response to Final Rejection was dated Oct. 21, 2016 to the U.S. Patent and Trademark Office for U.S. Appl. No. 13/157,803, filed Jun. 10, 2011 and granted as U.S. Pat. No. 9,638,632 on May 2, 2017 (Inventor—Darryl J. Bornhop et al.) (13 pages).
Response to Non Final Rejection was dated Feb. 22, 2016 to the U.S. Patent and Trademark Office for U.S. Appl. No. 13/402,104, filed Feb. 22, 2012 and granted as U.S. Pat. No. 9,562,853 on Feb. 7, 2017 (Inventor—Darryl J. Bornhop et al.) (9 pages).
Response to Non Final Rejection was dated Jul. 2, 2015 by the U.S. Patent and Trademark Office for U.S. Appl. No. 13/892,642, filed May 13, 2013 and granted as U.S. Pat. No. 9,273,949 on Mar. 1, 2016 (Inventor—Darryl J. Bornhop et al.) (11 pages).

Response to Non-Final Office Action filed Oct. 7, 2013 for U.S. Appl. No. 13/409,557, filed Mar. 1, 2012 (Applicant—Vanderbilt University // Inventors—Bornhop et al.) (9 pages).
Response to Non-Final Office Action filed Nov. 13, 2014 for U.S. Appl. No. 13/402,104, filed Feb. 22, 2012 (Applicant—Vanderbilt University // Inventors—Bornhop et al.) (14 pages).
Response to Non-Final Rejection filed Oct. 1, 2003 for U.S. Appl. No. 10/053,877, filed Jan. 24, 2002 (Applicant—Vanderbilt University // Inventors—Bornhop et al.) (2 pages).
Response to Non-Final Rejection dated Jul. 23, 2012 for U.S. Appl. No. 12/655,899, filed Jan. 8, 2010 (Applicant—Vanderbilt University // Inventors—Weinberger et al.) (11 pages).
Response to Office Action filed Jun. 29, 2010 for U.S. Appl. No. 12/122,175, filed May 16, 2008 (Applicant—Vanderbilt University // Inventors—Jones et al.) (17 pages).
Response to Office Action filed Jul. 19, 2013 for U.S. Appl. No. 13/157,803, filed Jun. 10, 2011 (Applicant—Vanderbilt University // Inventors—Bornhop et al.) (11 pages).
Response to Office Action filed Sep. 21, 2011 for U.S. Appl. No. 12/331,354, filed Dec. 9, 2008 (Applicant—Vanderbilt University // Inventors—Bornhop et al.) (14 pages).
Response to Office Action filed Dec. 7, 2012 for U.S. Appl. No. 12/674,610, filed Oct. 4, 2011 (Applicant—Vanderbilt University // Inventors—Bornhop et al.) (13 pages).
Response to Restriction Requirement filed Jan. 20, 2011 for U.S. Appl. No. 12/331,354, filed Dec. 9, 2008 (Applicant—Vanderbilt University // Inventors—Bornhop et al.) (9 pages).
Response to Restriction Requirement filed Mar. 7, 2013 for U.S. Appl. No. 13/409,557, filed Mar. 1, 2012 (Applicant —Vanderbilt University // Inventors—Bornhop et al.) (2 pages).
Restriction Requirement dated Jan. 7, 2013 for U.S. Appl. No. 13/409,557, filed Mar. 1, 2012 (Applicant—Vanderbilt University // Inventors—Bornhop et al.) (6 pages).
Rich et al., "High-resolution and high-throughput protocols for measuring drug/human serum albumin interactions using BIACORE," *Anal Biochem* 296:197-207 (2001).
Romero, F.A. et al., Potent and Selective a-Ketoheterocycle-Based Inhibitors of the Anandamide and Oleamide Catabolizing Enzyme, Fatty Acid Amide Hydrolase. J Med Chem. 2007; 50(5):1058-68.
Rother D, et al., "An active site homology model of phenylalanine ammonia-lyase from Petroselinum crispum," European Journal of; Biochemistry, 269: 3065-3075 (2002).
Rouhi Am, "Chiral chemistry," *Chemical & Engineering News*, 82: 47 (2004).
Rouhi Am, "Taking a measure of chiral riches—Researchers respond to high demand for ways to measure enantioenrichment quickly," *Chemical & Engineering News*, 80: 51 (2002).
Rouhi Am, Rouhi Am, "Chiral roundup—As pharmaceutical companies face bleak prospects, their suppliers diligently tend the fertile fields of chiral chemistry in varied ways," *Chemical & Engineering News*, 80: 43 (2002).
Rudolph Research Analytical, "Polarimetry," webpage retried from www.rudolphresearch.com/polarimetry.htm, (last accessed Aug. 3, 2009).
Rychlik W, et al., "New algorithm for determining primer efficiency in PCR and sequencing," J. NIH Res., 6: 78 (1994).
Saetear et al. (2015) Quantification of Plasmodium-host protein interactions on intact, unmodified erythrocytes by back- scattering interferometry. Malaria Journal, 14:88.
Saha et al., "Comparative study of IgG binding to proteins G and A: Nonequilibrium kinetic and binding constant determination with the acoustic waveguide device," Anal Chem, 75:835-842 (2003).
Saison-Behmoaras T, et al., "Short modified antisense oligonucleotides directed against ha-ras point mutations induce selective cleavage of the messenger RNA and inhibit T24 cell proliferation," *EMGO J.*, 10: 1111-1118 (1991).
Schipper EF, et al., "The Waveguide Mach-Zender Interferometer as Atrazine Sensor," *Analytical Chemistry*, 70: 1192-1197 (1998).
Schonfeld DL, et al., "Polarimetric assay for the medium-throuput determination of alpha-amino acid racemase activity," *Analytical Chemistry*, 76: 1184-1188 (2004).
Schuster B, et al., "The Mechanism of Action of Phenylalanine Ammonia-Lyase—the Role of Prosthetic Dehydroalanine," *Pro-*

(56) References Cited

OTHER PUBLICATIONS ceedings of the National Academy of Sciences of the United States of America, 92: 8433-8437 (1995).
Shea RG, et al., "Synthesis, hybridization properties and antiviral activity of lipid-oligodeoxynucleotide conjugates," Nucl. Acids Res., 8: 3777-3783 (1990).
Sidick et al., "Adaptive cross-correlation algorithm for extended scene Shack-Hartmann wavefront sensing," Optics Letters, vol. 33:213-215 (2008).
Sjodahl et al., "Electronic speckle photography: analysis of an algorithm giving the displacement with subpixel accuracy," Applied Optics, vol. 32:2278-2284 (1993).
Sjodahl et al., "Measurement of shape by using projected random patterns and temporal digital speckle photography," Applied Optics, vol. 38:1990-1997 (1999).
Sjodahl, "Accuracy in electronic speckle photography," Applied Optics, vol. 36:2875-2885 (1997).
Sjodahl, "Electronic speckle photography: increased accuracy by nonintegral pixel shifting," Applied Optics, vol. 33:6667-6673 (1994).
Skoog et al. (2014) Fundamentals of Analytical Chemistry (Brooks/Cole, Belmont, CA) 9th Ed.
Sorensen HS, "Self Calibrating Interferometric Sensor," PhD thesis Riso-PhD-19(EN), Riso National Laboratory, Denmark, Jan. 2006, pp. 1-145.
Sorensen HS, et al., "Absolute refractive index determination by microinterferometric backscatter detection," Analytical Chemistry, 75: 1946-1953 (2003).
Sorenson HS, et al., "Highly sensitive biosensing based on interference from light scattering in capillary tubes," Applied Physics Letters, 89(15) (2006).
Soumet, et al., "Identification by a multiplex PCR-based assay of Salmonella typhimurium and Salmonella enteritidis strains from environmental swabs of poultry houses ," Lett Appl Microbiol, 29(1) 1-6 (1999).
Speaker, et al., "Characterization of a calmodulin-binding protein that is deficient in trifluoperazine-resistant variants of the macrophage-like cell line J774," Proc Natl Acad Sci USA, 80:329-333 (1983).
StClaire JC, "Heat Index Flow Monitoring in Capillaries with Interferometric Backscatter Detection," Analytical Chemistry, 72(19): 4726-4730 (2000).
Stenberg et al. (1991) Quantitative-Determination of Surface Concentration of Protein with Surface-Plasmon Resonance Using Radiolabeled Proteins. Journal of Colloid and Interface Science 143(2):513-526.
STN Entry retrieved from STN Oct. 10, 2013 p. 1.
Stone H.A., et al., Microfluidics Toward a Lab-on-a-Chip, Annu. Rev. Fluid Mech. (2004) 36:381-411.
Stone, H.A. et al., Engineering Flows in Small Devices: Microfluidics Toward a Lab-on-a-Chip. Annu Rev Fluid Mech. 2004; 36:381-411.
Sulmann et al. (2014) Conformational Changes in Calcium-Sensor Proteins under Molecular Crowding Conditions. Chemistry 20 (22):6756-6762.
Sun et al. (1980) The Coil-Globule Transition—Radius of Gyration of Polystyrene in Cyclohexane. The Journal of Chemical Physics 73, 5971 73(12):5971-5975.
Supplementary European Search Report dated Feb. 10, 2006 for European Pat. App. No. 00959154.6 filed Aug. 17, 2000 (Applicant—Texas Tech Univeristy Health Sciences Center // Inventors—Bornhop et al.) (4 pages).
Supplementary International Search Report dated Oct. 5, 2012 for US/PCT/2008/063879 filed May 16, 2008 and published as WO 2008/144496 on Nov. 27, 2008 (Applicant—Vanderbilt University // Inventors—Jones et al.) (8 pages).
Supplementary International Search Report dated May 16, 2012 for PCT/US2005/38168 filed Oct. 24, 2005 and published as WO 2006/047408 on May 4, 2006 (Applicants—Vanderbilt University // Inventors—Bornhop et al.) (6 pages).

Suzuki, et al., "Planar lipid bilayer reconstitution with a microfluidic system," Lab Chip, 4: 502-505 (2004).
Svanbro et al., "Complex amplitude correlation for compensation of large in-plane motion in digital speckle pattern interferometry," Applied Optics, vol. 45:8641-8647 (2006).
Sviarchuk FP, et al., "Inhibition of HIV proliferation in MT-4 cells by antisense oligonucleotide conjugated to lipophilic groups," Biochimi, 75(1-2): 49-54 (1993).
Swinney K, et al., "A chip-scale universal detector for electrophoresis based on backscattering interferometry," Analyst, 125: 1713-1717 (2000).
Swinney K, et al., "Capillary-Scale Polarimetry for Flowing Streams," Analyst, 126: 673-675 (2001).
Swinney K, et al., "Chip-Scale Universal Detection Based on Backscatter Interferometry," Analytical Chemistry, 72: 2690-2695 (2000).
Swinney K, et al., "D-beta-Hydroxybutrate Reaction Kinetics Studied in Nanoliter Volumes using a Capillary Polarimeter," Applied Spectroscopy, 54: 1458-1469 (2000).
Swinney K, et al., "Ion Analysis Using Capillary Electrophoresis with Refractive Index Detection," Microchemical Journal, 62: 154-163 (1999).
Swinney K, et al., "Laser-Based Capillary Polarimetry," J. Capillary Electrophoresis and Microchip Technology, 6: 93-96 (1999).
Swinney K, et al., "Micro-interferometric backscatter detection using a diode laser," Analytica Chimica Acta, 400: 265-280 (1999).
Swinney K, et al., "Miniaturization—Quantification and evaluation of Joule heating in on-chip capillary electrophoresis," Electrophoresis, 23:8 (2002).
Swinney K, et al., "Nanoliter Volume Polarimetry," Applied Spectroscopy, 56(1): 134-138 (2002).
Swinney K, et al., "Non-Invasive Picoliter Volume Thermometry Based on Backscatter Interferometry," Electrohporesis, 22: 2032-2036 (2001).
Swinney K, et al., "Quantification and Evaluation of Joule Heating in On-Chip CE," Electrophoresis, 23(4): 621-625 (2002).
Swinney K, et al., "Ultrasmall volume refractive index detection using microinterferometry," Review of Scientific Instruments, 71: 2684-2692 (2000).
Swinney K, et al., "Universal Detection in Capillary Electrophoresis by Micro-Interferometric Backscatter," Analyst, 124: 221-226 (1999).
Swinney K, et al., "Universal Detection for Capillary Electrophoresis-Using Micro-Interferometric Backscatter Detection," J. MicroColumn Separation, 11: 596-604 (1999).
Swinney, et la., "A Review of CE Detection Methodologies," CRC Critical Reviews in Analytical Chemistry, 30(1): 1-30.
Synnergren et al. "Optical in-plane strain field sensor," Applied Optics, vol. 41:1323-1329 (2002).
Synnergren et al., "Application of digital speckle photography to flash x-ray studies of internal deformation fields in impact experiments," Applied Optics, vol. 36:4030-4036 (1999).
Synnergren et al., "Digital speckle photography: visualization of mesoflow through clustered fiber networks," Applied Optics, vol. 41:1368-1373 (2002).
Takushima et al., "Optical reflectometry based on correlation detection and its application to the in-service monitoring of WDM passive optical network," Optics Express, vol. 15:5318-5326 (2007).
Tan AM, et al., "Rapid fabrication of microfluidic devices in poly(dimethylsiloxane) by photocopying," Lab on a Chip, 1: 7-9 (2001).
Tarigan H, et al., "Capillary-Scale Refractive Index Detection by Interferometric Backscatter," Analytical Chemistry, 68: 1762-1770 (1996).
Theze, et al., "Interleukin 2 and its receptors: recent advances and new immunological functions," Immunology Today 17:481-486 (1996).
Tsukamoto M, et al., "Recent advances in the measurement of enantiomeric excesses," Advanced Synthesis & Catalysis, 344: 453-463.
Tumolo et al. (2004) Determination of the refractive index increment (dn/dc) of molecule and macromolecule solutions by surface plasmon resonance. Anal Biochem 333(2):273-279.

(56) References Cited

OTHER PUBLICATIONS

Tzeng and Kalodimos (2011) Protein dynamics and allostery: an NMR view. Curr Opin Struc Struc Biol 21(1):62-67.
Török, "Calmodulin conformational changes in the activation of protein kinases," *Biochem Soc Trans* 30:55-61 (2002).
Urwyler, S. et al., Positive Allosteric Modulation of Native and Recombinant β-Amniobutyric AcidB receptors by 2,6-Di-tert-butyl-4-(3-hydroxy-2,2-dimethyl-propyl)-pheol (CGP7930) and Its Aldehyde Analog CGP13501. Mol Pharmacol. 2001; 60(5):963-71.
van Delden RA, et al., "Color indicators of molecular chirality based on doped liquid crystals," Angewandte Chemie—International Edition, 40: 3198 (2001).
Vandonselaar et al. (1994) Trifluoperazine-induced conformational change in Ca(2+)-calmodulin. Nat Struct Biol. 1(11):795-801.
Varma (2016) Article does not explain the origin of free-solution protein interaction signals, PNAS 113(34):E4930.
Velazquez-Campoy and Freire (2006) Isothermal titration calorimetry to determine association constants for high-affinity ligands. Nat Protoc 1(1): 186-191.
Veldhuis GJ, et al., "Highly-sensitive Passive Integrated Optical Spiral-Shaped Waveguide Refractometer," *Applied Physics Letters*, 71(20): 2895-2897 (1997).
Viola et al., "Alignment by maximization of mutual information", International Conference on Computer Vision (E. Grimson, S. Shafer, A. Blake and K. Sugihara, eds.), IEEE Computer Society Press, Los Alamitos, CA, pp. 16-23, 1995.
Vogelstein, et al., "Digital PCR," *Proc Natl Acad Sci USA*, 96(16):9236-9241 (1999).
Volanthen M, et al., "Multiplexed optical fibre strain sensing using cross-correlation of subcarrier interferometric spectra," *Electronics Letters*, IEE Stevenage, GB, 32(3): 243-244 (1996).
Wang and Bornhop (2005) Dual-capillary backscatter interferometry for high-sensitivity nanoliter-volume refractive index detection with density gradient compensation. Anal Chem 77(24):7872-7877.
Wang et al., "Pseudophase information from the complex analytic signal of speckle fields and its applications. Part I: Microdisplacement observation based on phase-only correlation in the signal domain," Applied Optics, vol. 44:4909-4915 (2005).
Wang et al.,"Optical vortex metrology for nanometric speckle displacement measurement," Optics Express, vol. 14:120-127 (2006).
Wang Z, et al., "Attomole Sensitivity for Proteins and Polypeptides with On-chip CE and Universal Detection by Interferometric Backscatter, " *Electrophoresis*, 24(5): 865-873 (2003).
Wang, et al., "High-speed digital-image correlation method," Optics Letters, vol. 34:1955-1957 (2009).
Watkins, "Scattering from side-illuminated clad glass fibers for determination of fiber parameters," *J Opt Soc Am*, 64:767-772 (1974).
Wetmur JG, et al., "DNA Probes: Applications of the Principles of Nucleic Acid Hybridization," *Crit. Rev. Biochem. Mol. Biol.*, 26: 227-259 (1991).
Whitesides et al., "Soft lithography in biology and biochemistry," *Annu Rev Biomed Eng*, 3:335-373(2001).
Wienken et al. (2010) Protein-binding assays in biological liquids using microscale thermophoresis. Nat Commun. 1:100.
Wu ZY, et al., "Polymer microchips bonded by O-2-plasma activation," *Electrophoresis*, 23: 782-790 (2002).
Yamaguchi, "Fringe formation in speckle photography," J. Opt. Soc. Am. A, vol. 1:81-86 (1984).
Yanik, et al., "Development of a New Laser Based Polarimetric Detector and Its Application to High-performance Liquid Chromatography," PDR-Chiral, 1998.
Yeung, et al., "Electrochemistry-Based Real-Time PCR on a Microchip," *Anal Chem*, 80:363-368 (2008).
Ymeti, et al., "Realization of a multichannel integrated young interferometer chemical sensor," *Applied Optics*, 42: 5649-5660.
Young, et al., "Novel Recombinant—Antigen Enzyme Immunoassay for Serological Diagnosis of Syphilis," J Clin Microbio, 36(4):913-917 (1998).
Yu et al., "Energy landscape of aptamer/protein complexes studies by single-molecule force spectroscopy," *Chem Asian J*, 2:284-289 (2007).
Yu et al., "Interaction of an artificial antimicrobial peptide with lipid membranes," *Biochemica et Biophysica Acta*, 1788: 333-344 (2009).
Yu, J., et al., Energy Landscape of aptamer/ protein complexes studied by single molecule force spectroscopy. Chem Asian J (2007); 2:284-9.
Zandonella C, "Cell nanotechnology: The tiny toolkit," *Nature*, 423: 10-12 (2003).
Zazopoulos E, et al., "A genomics-guided approach for discovering and expressing cryptic metabolic pathways," *Nature Biotech.*, 21: 187-190 (2003).
Zhang et al. (2014) Microscale thermophoresis for the assessment of nuclear protein-binding affinities. Methods Mol Biol. 1094:269-76.
Zhang et al., "Proteins and cells on PEG immovilized silicon surfaces," *Biomaterials*, 19: 953-960.
Zhao et al. (2011) on the Distribution of Protein Refractive Index Increments. Biophysical Journal 100(9):2309-2317.
Zhihong et al., "A new sandwich-type assay of estrogen using piezoelectric biosensor immobilized with estrogen response element," Anal Commun, 36:281-283 (1999).
Zhou J, et al., "Spectroscopic studies of substrate interactions with clavaminate synthase 2, a multifunctional a-KG-dependent non-heme iron enzyme: Correlation with mechanisms and reactivities," *J. Am. Chem. Soc.*, 123: 7388-7398(2001).
Zhou JM, et al., "Spectroscopic studies of substrates and cosubstrate binding to the a-ketoglutarate-dependent non-heme iron enzyme clavaminate synthase 2: correlation to reactivities and mechanisms," *Journal of Inorganic Biochemistry*, 74: 350-350 (1999).
Zhou JM, et al., "Substrate binding to the α-keoglutarate-dependent non-heme iron enzyme clavaminate synthase 2: Coupling mechanism of oxidative decarboxylation and hydroxylation," J. Am. Chem. Soc., 120: 13539-13540 (1998).
Supplementary European Search Report dated Nov. 21, 2018 by the European Patent Office for Patent Application No. 1674080.7, which was filed on Jan. 22, 2016 and published as EP 3247988 dated Nov. 29, 2017 (Inventor—Bornhop et al.; Applicant—Vanderbilt University) (10 pages).

\* cited by examiner

*SCSR with no temperature control

PBS Buffer

PBS Buffer with 1% DMSO

ROBUST INTERFEROMETER AND METHODS OF USING SAME

CROSS-REFERENCE TO RELATED APPLICATIONS

This application is a Continuation of International Application No. PCT/US16/14439 filed on Jan. 22, 2016, which claims the benefit of U.S. Provisional Application No. 62/107,308, filed on Jan. 23, 2015, both of which applications are incorporated herein fully by reference in its entirety.

STATEMENT REGARDING FEDERALLY SPONSORED RESEARCH

This invention was made with government support under Grant no. 5R42GM090456-03 awarded by the National Institutes of Health (NIH), under Grant no. CHE 0848788 awarded by the National Science Foundation (NSF). The U.S. government has certain rights in the invention.

BACKGROUND

Back-scattering interferometry ("BSI") takes advantage of the multitude of light/sample interactions occurring every time a measurement is made. Described in U.S. Pat. No. 5,325,170 (Bornhop et al., Jun. 28, 1994), BSI is therefore one of the most sensitive analytical techniques and can be performed with extremely low sample concentrations and/or sample volumes. The last decade has seen a tremendous amount of growth in BSI technology. For example, U.S. Pat. No. 7,130,060 (Bornhop et al., Oct. 31, 2005) describes a method for determining absolute refractive index (RI) using BSI in which light is directed at a capillary tube and refractive index is determined as a function of the angle at which there is a marked change in intensity. Bornhop et al. (*Science* (2007) 317: 1732) describes a free-solution, label-free molecular interactions investigated by BSI. U.S. patent publication 2009-0185190 (Weinberger et al., Jul. 23, 2009) describes an interferometer for detecting analyte in a microfluidic chip. The device maintains a stable temperature at the chip with variation of no more than 0.005° C. and/or no more than 0.020° C. in the medium through which the optical train travels from a source of coherent light to the chip when ambient temperature changes up to 5 degrees centigrade over five minutes. The device comprises thermally isolated compartments that hinder heat transfer from one part of the instrument to another and temperature regulators that regulate temperature of the chip and the optical train compartment as a function of temperatures at the chip, in the compartment, and ambient.

Despite these advances, BSI measurements continue to suffer from several disadvantages—mainly related to eliminating sources of noise that would be irrelevant in less sensitive techniques. Recently developed methods utilizing refractive indices can require either the use of sequential measurements or the use of separate control measurements, such as in an adjacent capillary. The accuracy of such sequential or separate measurements can be less than ideal due to, for example, temperature changes that exist between measurements or between the optical properties of adjacent capillaries.

Accordingly, there is a need in the art for methods, systems, and apparatuses that can provide multiple refractive index related measurements simultaneously or substantially simultaneously without complications from, for example, thermal or pressure variations between sample and reference environments.

SUMMARY

As embodied and broadly described herein, the invention, in one aspect, relates to an interferometric detection system comprising a light beam that impinges two or more discrete zones along a channel. While traditional interferometric detection systems can utilize two channels positioned close to each other, variations, such as in temperature, between the two channels can result in increases in detection limits and/or measurement errors.

Disclosed are methods for determining a characteristic property of a sample comprising the steps of: (a) providing a sample positioned inside a channel formed in a substrate, wherein the channel has a longitudinal direction and a transverse direction; (b) interrogating the sample with a light beam, wherein the light beam is elongated in the longitudinal direction of the channel, such that the light beam is incident on at least a portion of the channel greater than 4 mm in length along the longitudinal direction; and (c) generating scattered light through reflective and refractive interaction of the light beam with a substrate/channel interface and the sample, the scattered light comprising interference fringe patterns elongated in at least one direction, wherein the interference fringe patterns shift in response to changes in the refractive index of the sample.

Also disclosed are interferometric detection systems comprising: (a) a channel formed in a substrate, wherein the channel has a longitudinal direction and a transverse direction, and wherein the channel is configured for reception of a liquid sample; (b) a light source for generating a light beam, wherein the light beam is elongated in the longitudinal direction of the channel, and wherein the light source is positioned to direct the light beam onto the substrate such that the light beam is incident on at least a portion of the channel greater than 4 mm in length, such that, during operation, scattered light is generated through reflective and refractive interaction of the light beam with a substrate/channel interface and the sample, the scattered light comprising interference fringe patterns elongated in at least one direction, wherein the interference fringe patterns shift in response to changes in the refractive index of the sample; and (c) a photodetector for simultaneously receiving the scattered light and generating a plurality of intensity signals.

Also disclosed are methods of improving precision when determining a characteristic property of a sample, the method comprising the step of: (a) introducing a sample into an inlet of a channel formed in a substrate; and (b) closing the inlet with a closure element, thereby reducing evaporation of liquid positioned within the channel and/or inlet.

Also disclosed are microfluidic devices comprising: (a) a substrate having a channel formed therein, wherein the channel has at least one inlet; (b) a closure element adapted to close (i.e., minimize exposed surface area of the sample by, e.g., sealing) the inlet, thereby reducing evaporation of liquid positioned within the channel and/or inlet.

Also disclosed are methods for determining a characteristic property of a sample comprising the steps of: (a) providing a channel formed in a substrate, wherein the channel has a longitudinal direction and a transverse direction, and wherein the channel is configured for reception of two or more liquid samples by having at least two inlets positioned at opposing locations (e.g., opposing ends) of the channel, and at least one outlet positioned at a point between the at least two inlets, thereby defining a right side of the channel and a left side of the channel; (b) introducing a first sample into the left side of the channel; (c) introducing a second sample into the right side of the channel; (d) simultaneously interrogating the samples with a light beam, wherein the light beam is elongated in the longitudinal direction of the channel, such that the light beam is incident on at least a portion of the left side of the channel and the right side of the channel; and (e) generating scattered light through reflective and refractive interaction of the light beam with a substrate/channel interface and the samples, the scattered light comprising interference fringe patterns elongated in at least one direction, wherein the interference fringe patterns shift in response to changes in the refractive index of the sample.

Also disclosed are interferometric detection systems comprising: (a) a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) a light source for generating a light beam, wherein the light beam is elongated in the longitudinal direction of the channel, and wherein the light source is positioned to direct the light beam onto the substrate such that the light beam is simultaneously incident on at least a portion of the right side of the channel and at least a portion of the left side of the channel, such that, during operation, scattered light is generated through reflective and refractive interaction of the light beam with a substrate/channel interface and the two or more samples, the scattered light comprising interference fringe patterns elongated in at least one direction, wherein the interference fringe patterns shift in response to changes in the refractive index of the two or more samples; and (c) a photodetector for simultaneously receiving the scattered light and generating a plurality of intensity signals.

Also disclosed are methods for determining a characteristic property of a sample comprising the steps of: (a) providing a sample positioned inside a channel formed in a substrate, wherein the channel has a longitudinal direction and a transverse direction; (b) interrogating the sample with a light beam, wherein the light beam is elongated in the longitudinal direction of the channel, wherein the photodetector is positioned less than 40 cm from the channel during interrogation; and (c) generating scattered light through reflective and refractive interaction of the light beam with a substrate/channel interface and the sample, the scattered light comprising interference fringe patterns elongated in at least one direction, wherein the interference fringe patterns shift in response to changes in the refractive index of the sample.

Also disclosed are interferometric detection systems comprising: (a) a channel formed in a substrate, wherein the channel has a longitudinal direction and a transverse direction, and wherein the channel is configured for reception of a liquid sample; (b) a light source for generating a light beam, wherein the light beam is elongated in the longitudinal direction of the channel, and wherein the light source is positioned to direct the light beam onto the substrate such that the light beam is incident on at least a portion of the channel greater, such that, during operation, scattered light is generated through reflective and refractive interaction of the light beam with a substrate/channel interface and the sample, the scattered light comprising interference fringe patterns elongated in at least one direction, wherein the interference fringe patterns shift in response to changes in the refractive index of the sample; and (c) a photodetector for simultaneously receiving the scattered light and generating a plurality of intensity signals, wherein the photodetector is positioned less than 40 cm from the channel during operation.

Also disclosed are methods for determining a characteristic property of a sample comprising the steps of: (a) providing a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) introducing a first sample into the left side of the channel and then closing the inlet of the left side of the channel with a first closure element, thereby reducing evaporation of the first sample; (c) introducing a second sample into the right side of the channel and then closing the inlet of the right side of the channel with a second closure element, thereby reducing evaporation of the second sample; (d) simultaneously interrogating the samples with a light beam, wherein the light beam is elongated in the longitudinal direction of the channel, such that the light beam is incident on greater than 4 mm of length of the channel in the longitudinal direction and simultaneously incident on at least a portion of the left side of the channel and at least a portion of the right side of the channel, wherein the photodetector is positioned less than 40 cm from the channel during interrogation; and (e) generating scattered light through reflective and refractive interaction of the light beam with a substrate/channel interface and the samples, the scattered light comprising interference fringe patterns elongated in at least one direction, wherein the interference fringe patterns shift in response to changes in the refractive index of the sample.

Also disclosed are interferometric detection systems comprising: (a) a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) a light source for generating a light beam, wherein the light beam is elongated in the longitudinal direction of the channel, and wherein the light source is positioned to direct the light beam onto the substrate such that the light beam is incident on at least a portion of the channel greater than 4 mm in length along the longitudinal direction and is simultaneously incident on at least a portion of the right side of the channel and at least a portion of the left side of the channel, such that, during operation, scattered light is generated through reflective and refractive interaction of the light beam with a substrate/channel interface and the two or more samples, the scattered light comprising interference fringe patterns elongated in at least one direction, wherein the interference fringe patterns shift in response to changes in the refractive index of the two or more samples; (c) a closure element adapted to close the inlet, thereby reducing evaporation of liquid positioned within the channel and/or inlet; and (d) a photodetector for simultaneously receiving the scattered light and generating a plurality of intensity signals, wherein the photodetector is positioned less than 40 cm from the channel during operation.

It will be apparent to those skilled in the art that various devices may be used to carry out the systems, methods, apparatuses, or computer program products of the present invention, including cell phones, personal digital assistants, wireless communication devices, personal computers, or dedicated hardware devices designed specifically to carry out aspects of the present invention. While aspects of the present invention may be described and claimed in a particular statutory class, such as the system statutory class, this is for convenience only and one of skill in the art will understand that each aspect of the present invention can be described and claimed in any statutory class, including systems, apparatuses, methods, and computer program products.

Unless otherwise expressly stated, it is in no way intended that any method or aspect set forth herein be construed as requiring that its steps be performed in a specific order. Accordingly, where a method, system, or computer program product claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Referring to FIG. 17A, data pertaining to a ConA-mannose binding assay performed in PBS buffer is shown. Referring to FIG. 17B, data pertaining to an AFP-anti-AFP binding assay performed in 98% human urine is shown.

FIG. 26A and FIG. 26B show fringes averaged over 40 pixels and over 400 pixels, respectively. FIG. 26C and FIG. 26D show FFT of fringes averaged over 40 pixels and over 400 pixels, respectively.

Figure 1:
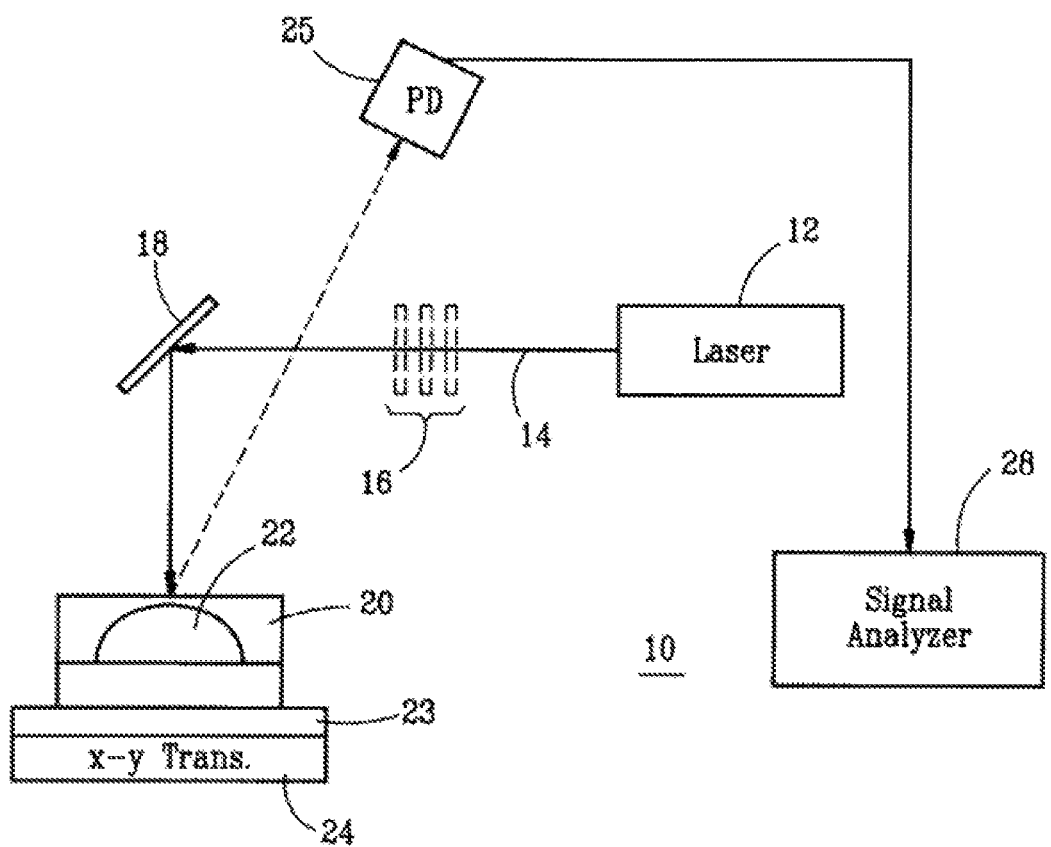
FIG. 1 shows a schematic block diagram of a conventional backscattering interferometric (BSI) system.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

A. Definitions

As used in the specification and the appended claims, the singular forms "a," "an" and "the" include plural referents unless the context clearly dictates otherwise. Thus, for example, reference to "a substrate," "a polymer," or "a sample" includes mixtures of two or more such substrates, polymers, or samples, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where the event or circumstance occurs and instances where it does not.

As used herein, the term "polymer" refers to a relatively high molecular weight organic compound, natural or synthetic (e.g., polyethylene, rubber, cellulose), whose structure can be represented by a repeated small unit, the monomer (e.g., ethane, isoprene, β-glucose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "bioassay" refers to a procedure for determining the concentration, purity, and/or biological activity of a substance.

As used herein, the term "chemical event" refers to a change in a physical or chemical property of an analyte in a sample that can be detected by the disclosed systems and methods.

For example, a change in refractive index (RI), solute concentration and/or temperature can be a chemical event. As a further example, a biochemical binding or association (e.g., DNA hybridization) between two chemical or biological species can be a chemical event. As a further example, a disassociation of a complex or molecule can also be detected as an RI change. As a further example, a change in temperature, concentration, and association/dissociation can be observed as a function of time. As a further example, bioassays can be performed and can be used to observe a chemical event.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Single Channel Sample Reference Interferometric Systems

In one aspect, the invention relates to an interferometric detection system comprising: (a) a channel formed in a substrate, wherein the channel has a longitudinal direction and a transverse direction, and wherein the channel is configured for reception of a liquid sample; (b) a light source for generating a light beam, wherein the light beam is elongated in the longitudinal direction of the channel, and wherein the light source is positioned to direct the light beam onto the substrate such that the light beam is incident on at least a portion of the channel greater than 4 mm in length, such that, during operation, scattered light is generated through reflective and refractive interaction of the light beam with a substrate/channel interface and the sample, the scattered light comprising interference fringe patterns elongated in at least one direction, wherein the interference fringe patterns shift in response to changes in the refractive index of the sample; and (c) a photodetector for simultaneously receiving the scattered light and generating a plurality of intensity signals.

In one aspect, the invention relates to an interferometric detection system comprising: (a) a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) a light source for generating a light beam, wherein the light beam is elongated in the longitudinal direction of the channel, and wherein the light source is positioned to direct the light beam onto the substrate such that the light beam is simultaneously incident on at least a portion of the right side of the channel and at least a portion of the left side of the channel, such that, during operation, scattered light is generated through reflective and refractive interaction of the light beam with a substrate/channel interface and the two or more samples, the scattered light comprising interference fringe patterns elongated in at least one direction, wherein the interference fringe patterns shift in response to changes in the refractive index of the two or more samples; and (c) a photodetector for simultaneously receiving the scattered light and generating a plurality of intensity signals.

In one aspect, the invention relates to an interferometric detection system comprising: (a) a channel formed in a substrate, wherein the channel has a longitudinal direction and a transverse direction, and wherein the channel is configured for reception of a liquid sample; (b) a light source for generating a light beam, wherein the light beam is elongated in the longitudinal direction of the channel, and wherein the light source is positioned to direct the light beam onto the substrate such that the light beam is incident on at least a portion of the channel greater, such that, during operation, scattered light is generated through reflective and refractive interaction of the light beam with a substrate/ channel interface and the sample, the scattered light comprising interference fringe patterns elongated in at least one direction, wherein the interference fringe patterns shift in response to changes in the refractive index of the sample; and (c) a photodetector for simultaneously receiving the scattered light and generating a plurality of intensity signals, wherein the photodetector is positioned less than 40 cm from the channel during operation.

In one aspect, the invention relates to an interferometric detection system comprising: (a) a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) a light source for generating a light beam, wherein the light beam is elongated in the longitudinal direction of the channel, and wherein the light source is positioned to direct the light beam onto the substrate such that the light beam is incident on at least a portion of the channel greater than 4 mm in length along the longitudinal direction and is simultaneously incident on at least a portion of the right side of the channel and at least a portion of the left side of the channel, such that, during operation, scattered light is generated through reflective and refractive interaction of the light beam with a substrate/channel interface and the two or more samples, the scattered light comprising interference fringe patterns elongated in at least one direction, wherein the interference fringe patterns shift in response to changes in the refractive index of the two or more samples; (c) a closure element adapted to close the inlet, thereby reducing evaporation of liquid positioned within the channel and/or inlet; and (d) a photodetector for simultaneously receiving the scattered light and generating a plurality of intensity signals, wherein the photodetector is positioned less than 40 cm from the channel during operation.

Figure 2:
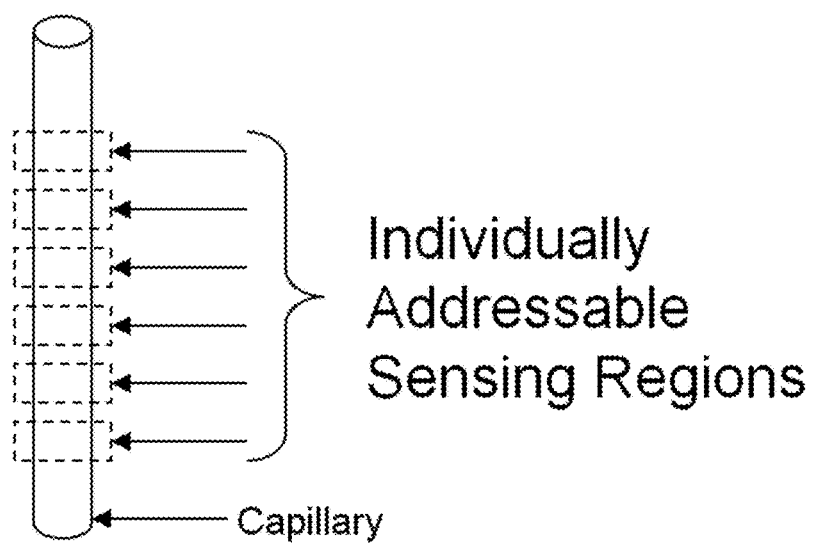
FIG. 2 shows a representative image of the serial patterning of individual zones along a channel for a BSI system.

An exemplary interferometric detection apparatus is illustrated in FIG. 1, wherein a light beam from a HeNe laser passes through beam conditioning optics (i.e., an optical element) to increase the width of the beam. Multiple regions (e.g., sample and reference) of a channel, as illustrated in FIG. 2, positioned on a temperature controlled chip can then be impinged with the spread light beam, creating backscattered light and elongated interference fringes that are directed to a s-D CCD array detector. A signal analyzer (i.e., computer) can then be used to interpret the signal intensity information from the detector and correlate the same to a change in the refractive index of the portion of the sample from the interrogated regions of the channel.

In another aspect, any element in a SCSR interferometric detection system or apparatus can comprise a single component or multiple components. In various aspects, multiple lasers can be utilized to produce separate light beams, wherein each light beam impinges a different portion of the channel. In another aspect, multiple optical elements can be utilized, either on a single light beam or multiple light beams. In another aspect, multiple detectors and/or signal analyzers can be present.

In a further aspect, the system further comprises at least one signal analyzer for receiving the intensity signals and determining therefrom one or more characteristic properties of the sample.

In a further aspect, the system further comprises a plurality of reservoirs, wherein each of the plurality of reservoirs is in fluid communication with one of the at least two inlets. In a still further aspect, the two or more samples comprise a first sample and a second sample. In yet a further aspect, the first sample is a sample to be analyzed, and the second sample is a reference. In an even further aspect, at least one of the two or more samples comprises a reference.

In a further aspect, the substrate and channel together comprise a capillary tube.

In a further aspect, the scattered light is backscattered light. In a still further aspect, the scattered light comprises backscattered light.

In a still further aspect, the invention relates to devices and methods wherein interferometric interrogation of a sample solution and interferometric interrogation a reference solution are performed simultaneously and performed within the same channel or within two channels in environmental communication (i.e., sharing the sample environment, including, for example, pressure and temperature) with the same light source. In one aspect, this can be accomplished by a single laser than has been elongated in the longitudinal direction of the channel.

1. Channel

In one aspect, the interferometric detection systems of the present invention comprise a channel formed in a substrate, wherein the channel has a longitudinal direction and a transverse direction, and wherein the channel is configured for reception of a liquid sample. In one aspect, the interferometric detection systems of the present invention comprise a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel. The channel of the present invention can, in various aspects, be formed from a substrate such as a piece of silica or other suitable optically transmissive material. In various aspects, the material of composition of the substrate has a different index of refraction than that of the sample to be analyzed. In a further aspect, as refractive index can vary significantly with temperature, the substrate can optionally be mounted and/or connected to a temperature control device. In a still further aspect, the substrate can be tilted, for example, about 7°, such that scattered light from channel can be directed to a detector.

In a further aspect, the channel has a generally semi-circular cross-sectional shape. A unique multi-pass optical configuration is inherently created by the channel characteristics, and is based on the interaction of the unfocused laser beam and the curved surface of the channel that allows interferometric measurements in small volumes at high sensitivity. Alternatively, the channel can have a substantially circular or generally rectangular cross-sectional shape. In a still further aspect, the substrate and channel together comprise a capillary tube. In yet a further aspect, the substrate and channel together comprise a microfluidic device, for example, a silica substrate, or a polymeric substrate [e.g., polydimethylsiloxane (PDMS) or polymethyl methacrylate (PMMA)], and an etched channel formed in the substrate for reception of a sample, the channel having a cross sectional shape. In an even further aspect, the cross sectional shape of a channel is semi-circular. In a still further aspect, the cross sectional shape of a channel is square, rectangular, or elliptical. In yet a further aspect, the cross sectional shape of a channel can comprise any shape suitable for use in a BSI technique. In an even further aspect, a substrate can comprise one or multiple channels of the same or varying dimensions. In various aspects, the channel can have a radius of from about 5 to about 250 micrometers, for example, about 5, 10, 20, 30, 40, 50, 75, 100, 150, 200, or 250 micrometers. In still other aspects, the channel can have a radius of up to about 1 millimeter or larger, such as, for example, 0.5 millimeters, 0.75 millimeters, 1 millimeter, 1.25 millimeters, 1.5 millimeters, 1.75 millimeters, 2 millimeters, or more.

A microfluidic channel, if present, can hold and/or transport the same or varying samples, and a mixing zone. The design of a mixing zone can allow at least initial mixing of, for example, one or more binding pair species. The at least initially mixed sample can then be subjected to a stop-flow analysis, provided that the reaction and/or interaction between the binding pair species continues or is not complete at the time of analysis. The specific design of a microfluidic channel, mixing zone, and the conditions of mixing can vary, depending on such factors as, for example, the concentration, response, and volume of a sample and/or species.

In a further aspect, a channel can be divided into multiple discrete zones along the length of the channel. In a still further aspect, a channel comprises at least two discrete zones. In yet a further aspect, a channel can comprise 2, 3, 4, 5, 6, 7, 8, 9, 10, or more zones. Any individual zone can have dimensions, such as, for example, length, the same as or different from any other zones along the same channel. In an even further aspect, at least two zones have the same length. In a still further aspect, all of the zones along a channel have the same or substantially the same length. In yet a further aspect, each zone can have a length along the channel of from about 1 to about 1,000 micrometers, for example, about 1, 2, 3, 5, 8, 10, 20, 40, 80, 100, 200, 400, 800, or 1,000 micrometers. In an even further aspect, each zone can have a length of less than about 1 micrometer or greater than about 1,000 micrometer, and the present disclosure is not intended to be limited to any particular zone dimension. Further, any individual zone can be in contact with or separated from an adjacent zone. In a still further aspect, at least one zone is in contact with an adjacent zone. In yet a further aspect, each of the zones along a channel is in contact such that there are no breaks between individual zones. In an even further aspect, at least one zone is separated from an adjacent zone by a portion of the capillary not in a zone. In a still further aspect, each of the zones along a channel is separated from each other such that no zones are in direct contact with another. In yet a further aspect, at least one zone can be used as a reference and/or experimental control. In an even further aspect, each measurement zone can be positioned adjacent to a reference zone, such that the channel comprises alternating measurement and reference zones. It should be noted that the zones along a channel do not need to be specifically marked or delineated, only that the system be capable of addressing and detecting scattered light from each zone.

In a further aspect, a first discrete zone is disposed between a first inlet and the at least one outlet, and wherein a second discrete zone is disposed between a second inlet and the at least one outlet.

In a further aspect, any one or more zones in a channel can be separated from any other zones by a junction, such as, for example, a union, coupling, tee, injection port, mixing port, or a combination thereof. For example, one or more zones in the flow path of a sample can be positioned upstream of an injection port where, for example, an analyte can be introduced. In such an aspect, one or more zones can also be positioned downstream of the injection port.

In a further aspect, a channel can be divided into two, three, or more regions, wherein each region is separated from other regions by an outlet. In a still further aspect, an outlet can prevent a fluid in one region of a channel from contacting and/or mixing with a fluid from another region of the channel. In yet a further aspect, any combination of regions or all of the regions can be positioned such that they will be impinged with at least a portion of the light beam. In such an aspect, multiple regions of a single channel can be used to conduct multiple analyses of the same or different type in a single instrumental setup. In an even further aspect, a channel has two regions, wherein an outlet is positioned in the channel between the two regions, and wherein each of the regions are at least partially in an area of the channel where the light beam is incident.

Figure 7:
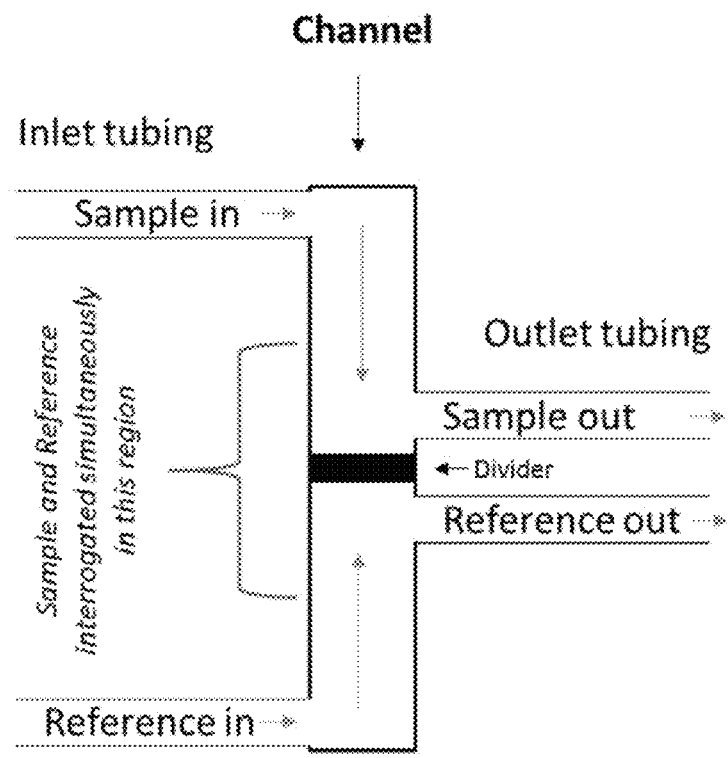
FIG. 7 shows two representative schematics of a channel with a separator and multiple inputs and outputs, as detailed in various aspects of the present invention.
Figure 7:
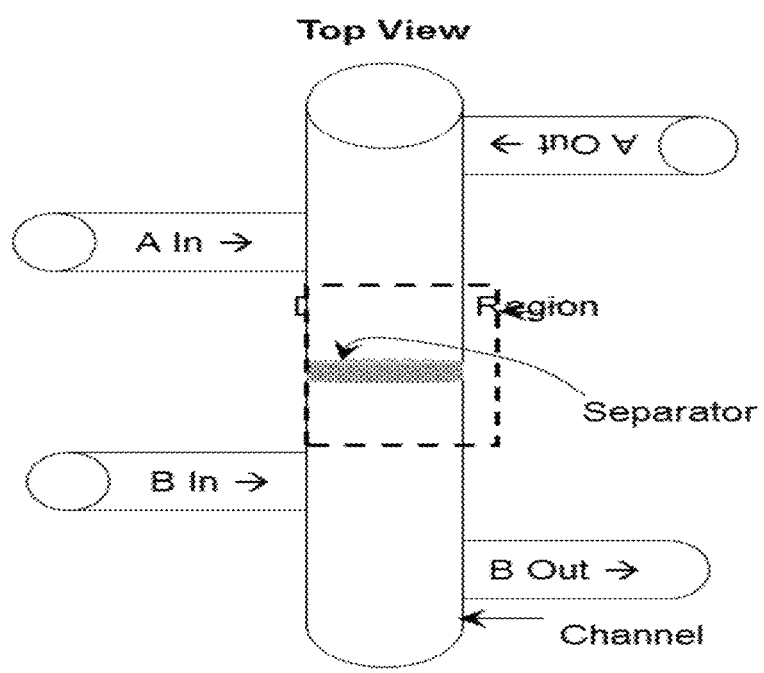

In a further aspect, if multiple regions are present, each region can have an input and an output port. An exemplary schematic of a channel comprising two regions, wherein each region has an input and an output port is illustrated in FIG. 7. In a still further aspect, the input and/or output ports can be configured so as not to interfere with the generation of scattered light, such as, for example, backscattered light, and the resulting measurements. It should be noted that other geometric designs and configurations can be utilized, and the present invention is not intended to be limited to the specific exemplary configurations disclosed herein. Thus, in one aspect, a single channel can allow for analysis of multiple samples simultaneously in the same physical environment.

Figure 13A:
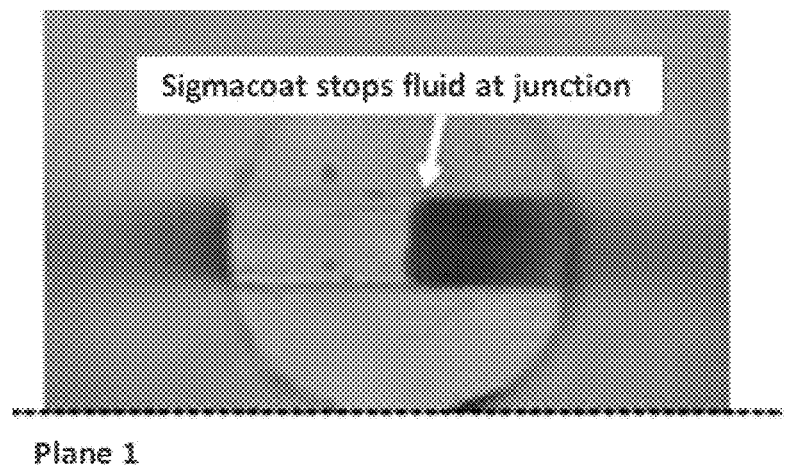
FIGS. 13A and 13B show representative images illustrating Sigmacote™ (13A) and the cross section of a chip with a gap in the channel that (13B) works to stop fluid.
Figure 13B:
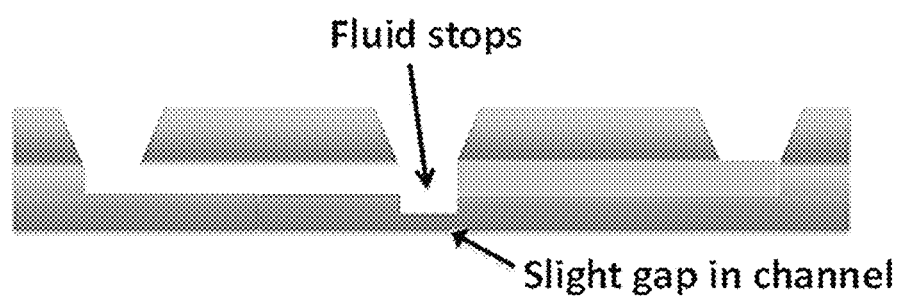

As illustrated in FIG. 13, a hydrophobic coating can be optionally used to stop capillary action of solution within the channel. FIG. 13 shows a photograph of Sigmacoat serving as a hydrophobic coating, to stop the capillary action and inhibit the sample and reference from meeting in the center of the channel where they would mix. The liquid has stopped at this coated region, as capillary action is arrested. This demonstrates that a hydrophobic coating can be used to create a gap in the center of the channel, so that the sample and reference solutions can be introduced and separated within the SCSR detection beam interrogating region.

Figure 5B:
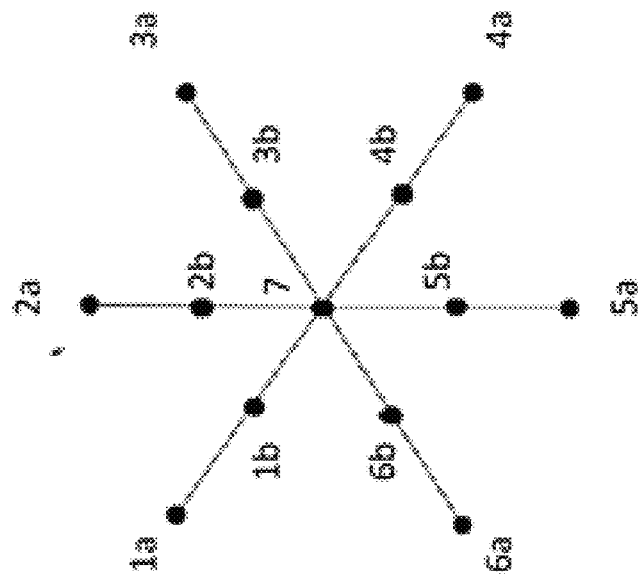
FIG. 5B shows another example SCSR BSI configuration. Samples can be inserted into 1*a*, 2*a*, 3*a*, 4*a*, 5*a*, and 6*a*. 1*b*, 2*b*, 3*b*, 4*b*, 5*b*, and 6*b* indicated sample removal holes and capillary stops. One reference for all 6 samples would be inserted into 7, and would be pulled by capillary action into each of the six spokes, allowing sample/reference simultaneous measurements.
Figure 5A:
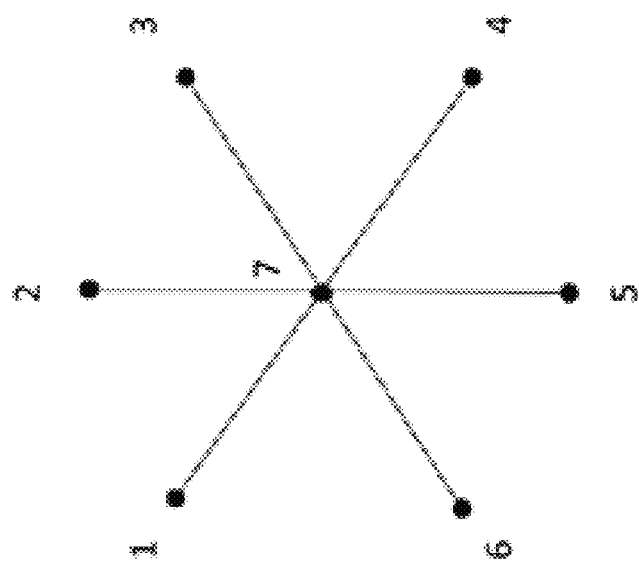
FIG. 5A shows an example SCSR BSI configuration. Points 1-6 indicate sample inlet holes, and 7 indicates sample removal hole and capillary stop. For the first sample/reference pair, the sample would be inserted into 1 and the reference would be inserted into 4, and capillary action would draw them into the channels. Sample would be inserted into 2, and its reference into 5, and sample into 3 and its reference into 6.
Figure 6A:
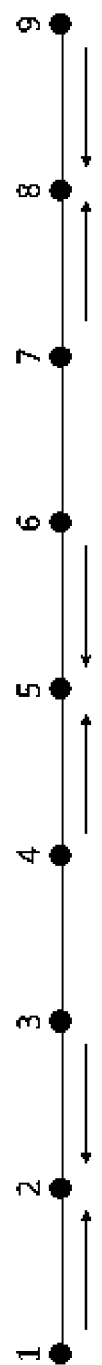
FIG. 6A shows a further example SCSR BSI configuration. Points 1, 3, 5, 7, and 9 would be sample inlet wells, and 2, 4, 6, and 8 would be sample removal hole and capillary stop. A single reference could be placed in 1 while samples were placed in 3, 5, 7, and 9. Or, a sample/reference pair could be inserted into 1 and 3, a second sample reference pair into 4 and 6, and a third pair in 7 and 9.
Figure 6B:
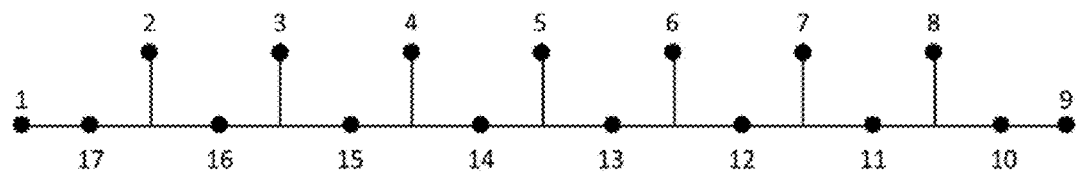
FIG. 6B shows a further example SCSR BSI configuration. Holes 1 through 9 would be sample inlet wells, and holes 10 through 17 would be sample removal holes and capillary stops. This configuration would allow 4 sample/reference pairs.
Figure 6C:
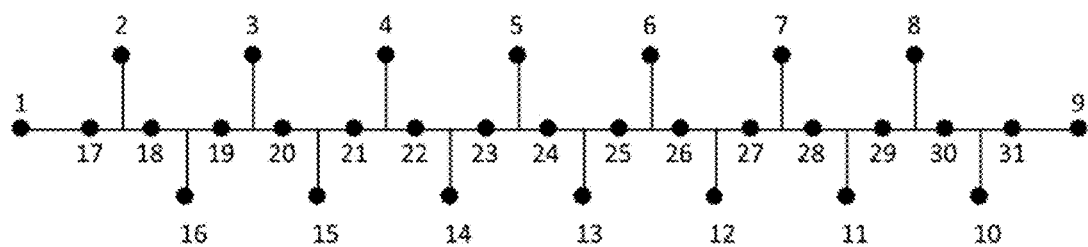
FIG. 6C shows a further example SCSR BSI configuration. Holes 1 through 16 would be sample inlet wells, and holes 17 through 31 would be sample removal holes and capillary stops. This configuration would allow 8 sample/reference pairs.

As depicted in FIG. 5 and FIG. 6, the inlets can be positioned at opposing locations (e.g., opposing ends) of the channel. Opposing locations can be, for example, located at the ends of the channel, with an outlet positioned between the inlets. It is appreciated, however, that the inlets are not required to be at the ends of the channel, as long as the configuration of inlets and outlets allows for SCSR interrogation as described herein.

2. Light Source

In one aspect, the interferometric systems of the present invention comprise a light source for generating a light beam, wherein the light beam is elongated in the longitudinal direction of the channel, and wherein the light source is positioned to direct the light beam onto the substrate such that the light beam is incident on at least a portion of the channel greater than 4 mm in length, such that, during operation, scattered light is generated through reflective and refractive interaction of the light beam with a substrate/channel interface and the sample, the scattered light comprising interference fringe patterns elongated in at least one direction, wherein the interference fringe patterns shift in response to changes in the refractive index of the sample.

In one aspect, the interferometric systems of the present invention comprise a light source for generating a light beam, wherein the light beam is elongated in the longitudinal direction of the channel, and wherein the light source is positioned to direct the light beam onto the substrate such that the light beam is simultaneously incident on at least a portion of the right side of the channel and at least a portion of the left side of the channel, such that, during operation, scattered light is generated through reflective and refractive interaction of the light beam with a substrate/channel interface and the two or more samples, the scattered light comprising interference fringe patterns elongated in at least one direction, wherein the interference fringe patterns shift in response to changes in the refractive index of the two or more samples.

In various aspects, the light source generates an easy to align optical beam that is incident on the etched channel for generating scattered light. In a further aspect, the light source generates an optical beam that is collimated, such as, for example, the light emitted from a HeNe laser. In a still further aspect, the light source generates an optical beam that is not well collimated and disperses in, for example, a Gaussian profile, such as that generated by a diode laser.

Typically, two types of lasers can be employed. In various aspects, one laser (the diode) creates a laser beam that is elongated in the longitudinal direction of the channel. In further aspects, the other (HeNe) creates a laser beam that is not elongated longitudinally along the length of the channel, but can be later elongated longitudinally along the length of the channel by beam-stretching optics. These methods can both achieve the same end of an elongated beam impinging upon the channel, but do so through different means. It can be noted that, in certain aspects, when the diameter of the laser beam is the same as the thickness of the glass chip, new interference phenomena can arise. This can be avoided by selecting the width of the beam to be smaller than the thickness of the glass chip (0.8 mm width laser and 1.7 mm thickness glass chip).

In a further aspect, a single light beam is incident upon the substrate.

In a further aspect, the light beam has a substantially uniform intensity profile across at least a portion of the plurality of discrete zones. In a yet further aspect, the light beam has a substantially Gaussian intensity profile in the axis perpendicular to the zones. In a still further aspect, the portion of the light beam impinging the channel has an elongated intensity profile.

In various aspects, the light beam is incident on at least a portion of the channel greater than 4 mm in length along the longitudinal direction. In a further aspect, the light beam is incident on at least a portion of the channel greater than 5 mm of length of the channel in the longitudinal direction. In a still further aspect, the light beam is incident on at least a portion of the channel greater than 6 mm of length of the channel in the longitudinal direction. In yet a further aspect, the light beam is incident on at least a portion of the channel greater than 7 mm of length of the channel in the longitudinal direction. In an even further aspect, the light beam is incident on at least a portion of the channel greater than 8 mm of length of the channel in the longitudinal direction. In a still further aspect, the light beam is incident on at least a portion of the channel greater than 9 mm of length of the channel in the longitudinal direction. In yet a further aspect, the light beam is incident on at least a portion of the channel greater than 10 mm, 12 mm, 14 mm, 16 mm, 18 mm, or 20 mm of length of the channel in the longitudinal direction.

In a further aspect, at least a portion of the light beam incident on the channel covers at least two discrete zones. In a still further aspect, at least a portion of the light beam is incident on the channel such that the intensity of the light on each of at least two zones is the same or substantially the same. In yet a further aspect, at least a portion of the light beam is incident on the channel such that the each of the zones along the channel receive the same or substantially the same intensity of light. For example, a light beam having a Gaussian intensity profile can be incident on a channel such that at least two zones along the channel are within the peak of the intensity profile, receiving the same or substantially the same intensity of light. In an even further aspect, the portion of the light beam incident on the channel can have a non-Gaussian profile, such as, for example, a plateau (e.g., top-hat). The portion of the light beam in the wings of the Gaussian intensity profile can be incident upon other portions of the channel or can be directed elsewhere.

In a further aspect, variations in light intensity across zones of interest can result in measurement errors. In a still further aspect, if portions of a light beam having varying intensity are incident upon multiple zones of a channel, a calibration can be performed wherein the expected intensity of light, resulting interaction, and scattering is determined for correlation of future measurements.

The light source can comprise any suitable equipment and/or means for generating light, provided that the frequency and intensity of the generated light are sufficient to interact with a sample and/or a marker compound and provide elongated fringe patterns as described herein. Light sources, such as HeNe lasers and diode lasers, are commercially available and one of skill in the art could readily select an appropriate light source for use with the systems and methods of the present invention.

In a further aspect, a light source can comprise a single laser. In a still further aspect, a light source can comprise two or more lasers, each generating a beam that can impinge one or more zones of a channel. In yet a further aspect, if two or more lasers are present, any individual laser can be the same as or different from any other laser. For example, two individual lasers can be utilized, each producing a light beam having different properties, such as, for example, wavelength, such that different interactions can be determined in each zone along a channel.

As with any interferometric technique for micro-chemical analysis, it can be advantageous, in various aspects, for the light source to have monochromaticity and a high photon flux. If warranted, the intensity of a light source, such as a laser, can be reduced using neutral density filters.

In a further aspect, the system further comprises an optical element positioned between the light source and the channel, wherein the optical element is capable of at least one of spreading, splitting, rastering, or a combination thereof the light beam in a direction parallel to the length of the channel. In various aspects, such an optical element can facilitate contact of the light beam with two or more zones along a channel. In a further aspect, a light source, such as a diode laser, generates a light beam having a Gaussian profile, and an optical element is not necessary or present. In a still further aspect, a light source, such as a HeNe laser, generates a collimated light beam and an optical element can be present to spread the light beam and facilitate contact of the light beam with at least two zones along the channel. Such a light beam configuration can allow for multiple measurements or sample and reference measurements to be made simultaneously or substantially simultaneously within the same channel.

In a further aspect, the optical element is capable of spreading the light beam in a direction parallel to the length of the channel. In a still further aspect, the optical element comprises a cylindrical lens. In yet a further aspect, the optical element comprises an anamorphic lens.

In a further aspect, an optical element can comprise a dispersing element capable of dispersing the light beam in at least one direction. Such an element can be useful to disperse a well collimated light beam in a direction parallel to the longitudinal axis of a channel, such that when incident upon the channel, the light beam contacts at least two zones. In such an aspect, the optical element, if present, can comprise a cylindrical lens, such as, for example, a 50.8 mm by 19 mm cylindrical lens with an effective focal length of 25.4 cm, to produce a beam 0.8 mm by 4.0 mm. A cylindrical lens can thus be used to disperse the light beam from a HeNe laser to a line. An amorphic lens can also be used.

In a further aspect, an optical element can comprise a beam splitting element capable of splitting a well collimated light beam into two or more individual beams, each of which can be incident upon a separate zone on the same channel.

In a further aspect, an optical element can comprise a rastering element capable of rastering a light beam across two or more zones of a channel. If such a rastering element is present, the speed at which the beam is rastered across the two or more zones should be sufficiently fast to prevent measurement errors from occurring due to temperature changes and/or changes in sample composition flowing through a capillary channel.

In a further aspect, two or more optical elements of the same or varying type can be utilized. In a still further aspect, additional beam conditioning optics can be utilized in addition to, for example, a dispersing cylindrical lens. In yet a further aspect, other types of optical elements capable of facilitating contact of the light beam with at least two zones along the channel are contemplated, and the present disclosure is not intended to be limited to the particular optical elements recited herein. In an even further aspect, an optical element, such as, for example, a lens, can be positioned in the optical path between the light source and the channel. In a still further aspect, an optical element, such as, for example, a rastering element, can be attached to or integral with the light source.

In a further aspect, one or more additional optical components can be present, such as, for example, a mirror, a neutral density filter, or a combination thereof, so as to direct the light beam and/or the scattered light in a desired direction or to adjust one or more properties of a light beam.

3. Closure Element

In one aspect, the interferometric systems of the present invention comprise a closure element adapted to close the inlet, thereby reducing evaporation of liquid positioned within the channel and/or inlet. In a further aspect, the interferometric systems of the present invention may comprise multiple closure elements. Examples of closure elements include, but are not limited to, caps, corks, ferrules, stoppers, collets, and tops.

While it is not strictly necessary that the one or more inlets be completely sealed by the closure element, it can be preferred that the closure element, when in use, reduces, minimizes, or eliminates exposure of the sample to the environment.

The distance from the chip surface to the closure element may be optimized for volume minimization, ease of production, and injection consistency. A smaller volume, dimension, and surface area exposed to the environment minimize the evaporation of solvents and solutions. This is because 1) the sample it always contained within the dispensing object (pipette), 2) only a small area of the sample/reference solution surface is exposed to the environment (i.e., the exposed surface area is defined by the inner diameter of the receptacle which is very small), and 3) the sample detection zone cannot communicate with the atmosphere due to the fact that it is spatially separated from the top of the receptacle (where evaporation can occur) and after the injection is performed, a valve to the waste tube connected to the exit hole is closed, thereby reducing, minimizing, or eliminating environmental communication. With the detection zone residing several centimeters from the introduction site, the time for evaporative communication is much longer (e.g., minutes) than needed to perform the data collection. Thus, without wishing to be bound by theory, the SCSR method may allow for a user to place a drop from a standard pipette, have the low-microliter volume sample be automatically and passively (no pump) introduced into the detection region, and be at the same pressure as the reference fluid.

It is appreciated that reduction or elimination of evaporation can also be accomplished by locating the interrogation region a sufficient distance from an inlet. For example, the outer edge of the interrogation region can be positioned at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, at least 25 mm, at least 30 mm, at least 40 mm, at least 50 mm from an inlet. In one aspect, the distance can be measured along the horizontal length of the channel between the inlet and an edge of the interrogation region. In a further aspect, the distance can be measured along the horizontal length of the channel between the inlet and an edge of the interrogation region as well as the vertical distance of the inlet itself. It is understood that this aspect can be used in combination with one or more closure elements.

4. Photodetector

In one aspect, the interferometric systems of the present invention comprise a photodetector for simultaneously receiving the scattered light and generating a plurality of intensity signals.

In one aspect, the interferometric systems of the present invention comprise a photodetector for simultaneously receiving the scattered light and generating a plurality of intensity signals, wherein the photodetector is positioned less than 40 cm from the channel during operation.

A photodetector detects the scattered light and converts it into intensity signals that vary as the positions of the light bands in the elongated fringe patterns shift, and can thus be employed to determine the refractive index (RI), or an RI related characteristic property, of the sample. Exemplary properties that can be detected and/or quantified using the inventive techniques can comprise, without limitation, changes in mass, concentration, conformation, structure, charge level, level of hydration, or a combination thereof. In other aspects, the progress of one or more chemical reactions can be monitored, such as, for example, that can occur in an aqueous or a non-aqueous solvent.

The photodetector can, in various aspects, comprise any suitable image sensing device, such as, for example, a bi-cell sensor, a linear or area array CCD or CMOS camera and laser beam analyzer assembly, a photodetector assembly, an avalanche photodiode, or other suitable photodetection device. In a further aspect, the photodetector is an array photodetector capable of detecting multiple elongated interference fringe patterns. In a still further aspect, a photodetector can comprise multiple individual photodetectors to detect the elongated interference fringe patterns produced by the interaction of the light beam with the sample, channel wall, and optional marker compounds. The scattered light incident upon the photodetector comprises elongated interference fringe patterns that correspond to the discrete zones along the length of the channel. These elongated interference fringe patterns include a plurality of light bands whose positions shift as the refractive index of that portion of the sample is varied, either through compositional changes, temperature changes, or a combination thereof. The specific position of the photodetector can vary depending upon the arrangement of other elements. In yet a further aspect, the photodetector can be positioned at an approximately 45° angle to the channel.

The intensity signals from the photodetector can then be directed to a signal analyzer for fringe pattern analysis and determination of the RI or RI related characteristic property of the sample and/or reference in each zone of the channel. The signal analyzer can be a computer or a dedicated electrical circuit. In various aspects, the signal analyzer includes the programming or circuitry necessary to determine from the intensity signals, the RI or other characteristic property of the sample in each discrete zone of interest. In a further aspect, the signal analyzer is capable of detecting positional shifts in interference fringe patterns and correlating those positional shifts with a change in the refractive index of at least a portion of the sample. In a still further aspect, the signal analyzer is capable of detecting positional shifts in interference fringe patterns and correlating those positional shifts with a change in the refractive index occurring in the zones of the channel. In yet a further aspect, the signal analyzer is capable of comparing data received from a photodetector and determining the refractive index and/or a characteristic property of the sample in any two or more zones of the channel.

In a further aspect, the signal analyzer is capable of interpreting an intensity signal received from a photodetector and determining one or more characteristic properties of the sample in each of the zones of the channel. In a still further aspect, the signal analyzer can utilize a mathematical algorithm to interpret positional shifts in the interference fringe patterns incident on a photodetector. In yet a further aspect, known mathematical algorithms and/or signal analysis software, such as, for example, deconvolution algorithms, can be utilized to interpret positional shifts occurring from a multiplexed scattering interferometric analysis.

The photodetector can be employed for any application that requires interferometric measurements; however, the photodetector can be particularly useful for making universal solute quantification, temperature, and flow rate measurements. In these applications, the photodetector provides ultra-high sensitivity due to the multi-pass optical configuration of the channel. In the temperature measuring aspect, a signal analyzer receives the signals generated by the photodetector and analyzes them using the principle that the refractive index of the sample varies proportionally to its temperature. In this manner, the signal analyzer can calculate temperature changes in the sample from positional shifts in the detected interference fringe patterns. In a further aspect, the ability to detect elongated interference fringe patterns from interactions occurring in two or more zones along a channel can provide real-time reference and/or comparative measurements without the problem of changing conditions between measurements. In a still further aspect, a signal analyzer, such as a computer or an electrical circuit, can thus be employed to analyze the photodetector signals, and determine the characteristic property of the sample.

In the flow measuring aspect, the same principle is also employed by the signal analyzer to identify a point in time at which perturbation is detected in a flow stream in the channel. In the case of a thermal perturbation, a flow stream whose flow rate is to be determined, is locally heated at a point that is a known distance along the channel from the detection zone. The signal analyzer for this aspect includes a timing means or circuit that notes the time at which the flow stream heating occurs. Then, the signal analyzer determines from the positional shifts of the light bands in the interference fringe patterns, the time at which thermal perturbation in the flow stream arrives at the detection zone. The signal analyzer can then determine the flow rate from the time interval and distance values. Other perturbations to the flow stream, include, but are not limited to, introduction into the stream of small physical objects, such as glass microbeads or nanoparticles. Heating of gold particles in response to a chemical reaction or by the change in absorption of light due to surface-bound solutes or the capture of targets contained within the solution can be used to enhance the temperature induced RI perturbation and thus to interrogate the composition of the sample. In a further aspect, measurements at multiple zones along the channel can be used to determine temperature gradients or rate of temperature change of a sample within the channel.

In a further aspect, the systems and methods of the present invention can be used to obtain multiple measurements simultaneously or substantially simultaneously from discrete zones along the length of a channel. In such an aspect, each zone can provide a unique measurement and/or reference. In a further aspect, temporal detection can be used to measure changes in a sample over time as the sample flows through the channel, for example, with a flow injection analysis system.

In a further aspect, the sample is a fluid, for example a gas, a liquid, or a supercritical fluid. In a still further aspect, the sample is a liquid, which can be a substantially pure liquid, a solution, or a mixture (e.g., biological fluids, cellular fluids). In a still further aspect, the sample can further comprise one or more analytes. In yet a further aspect, a sample can be introduced into the channel via an injection port at, for example, one end of the channel.

As the light beam impinges one or more discrete regions of a channel, the resulting elongated interference fringe patterns can move with a change in refractive index. The ability to analyze multiple discrete zones simultaneously can provide high spatial resolution and can provide measurement techniques with an integrated reference.

In a further aspect, the photodetector is capable of spatially resolving scattered light incident on a surface thereof. In a still further aspect, the photodetector comprises a three dimensional array.

In various aspects, the photodetector resolution, including pixel size, spacing, and photon flux sensitivity, can be selected based upon certain specifications. Thus, in various aspects, between about 50 camera pixels and 400 camera pixels can be interrogated. In a further aspect, between about 50 camera pixels and 350 camera pixels can be interrogated. In a still further aspect, between about 50 camera pixels and 300 camera pixels can be interrogated. In yet a further aspect, between about 50 camera pixels and 250 camera pixels can be interrogated. In an even further aspect, between about 50 camera pixels and 200 camera pixels can be interrogated. In a still further aspect, between about 50 camera pixels and 150 camera pixels can be interrogated.

C. Microfluidic Devices

In one aspect, the invention relates to a microfluidic device comprising: (a) a substrate having a channel formed therein, wherein the channel has at least one inlet; (b) a closure element adapted to close the inlet, thereby reducing evaporation of liquid positioned within the channel and/or inlet.

In a further aspect, closing is via friction fit. In a still further aspect, closing is via screw fit.

In a further aspect, the device further comprises a reservoir positioned between the inlet and the channel. In a still further aspect, the device further comprises an interferometric detection system.

In a further aspect, the substrate and channel together comprise a capillary tube.

D. Analytical Methods

Conventional backscattering interferometry, as illustrated in FIG. 1, utilizes interference fringes generated by backscattered light to detect refractive index changes in a sample. The backscatter detection technique is generally disclosed in U.S. Pat. No. 5,325,170 to Bornhop, and U.S. Patent Publication No. US2009/0103091 to Bornhop, both of which are hereby incorporated by reference. With reference to FIG. 1, a conventional backscattering interferometric detection system 10 comprises a laser 12 that produces a light beam 14. The light beam can be directed through one or more neutral density filters 16 to reduce the intensity of the light beam, before being reflected on a mirror 18 and directed to impinge an etched channel 22 on a chip 20. The chip can also be positioned on a temperature controlled support block 23 and/or an X-Y translation stage 24. After various reflective and refractive interactions with the channel and sample, the scattered light can be directed to a detector 25, and the intensity signals generated by the detector interpreted by a computer based signal analyzer 28.

Figure 3:
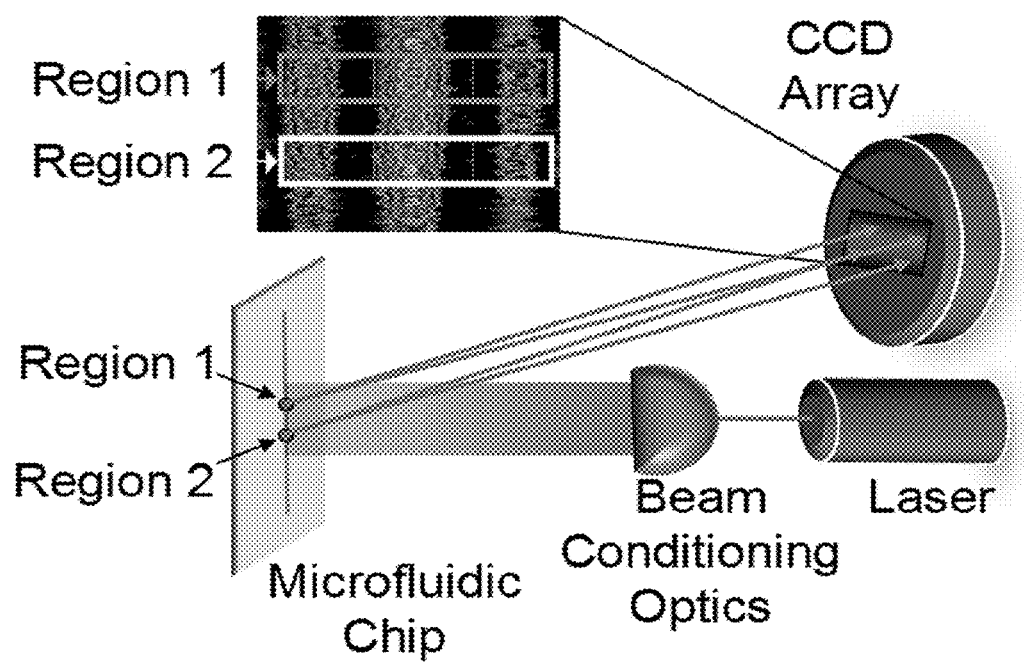
FIG. 3 shows a representative block diagram of the SCSR configuration.
Figure 4A:
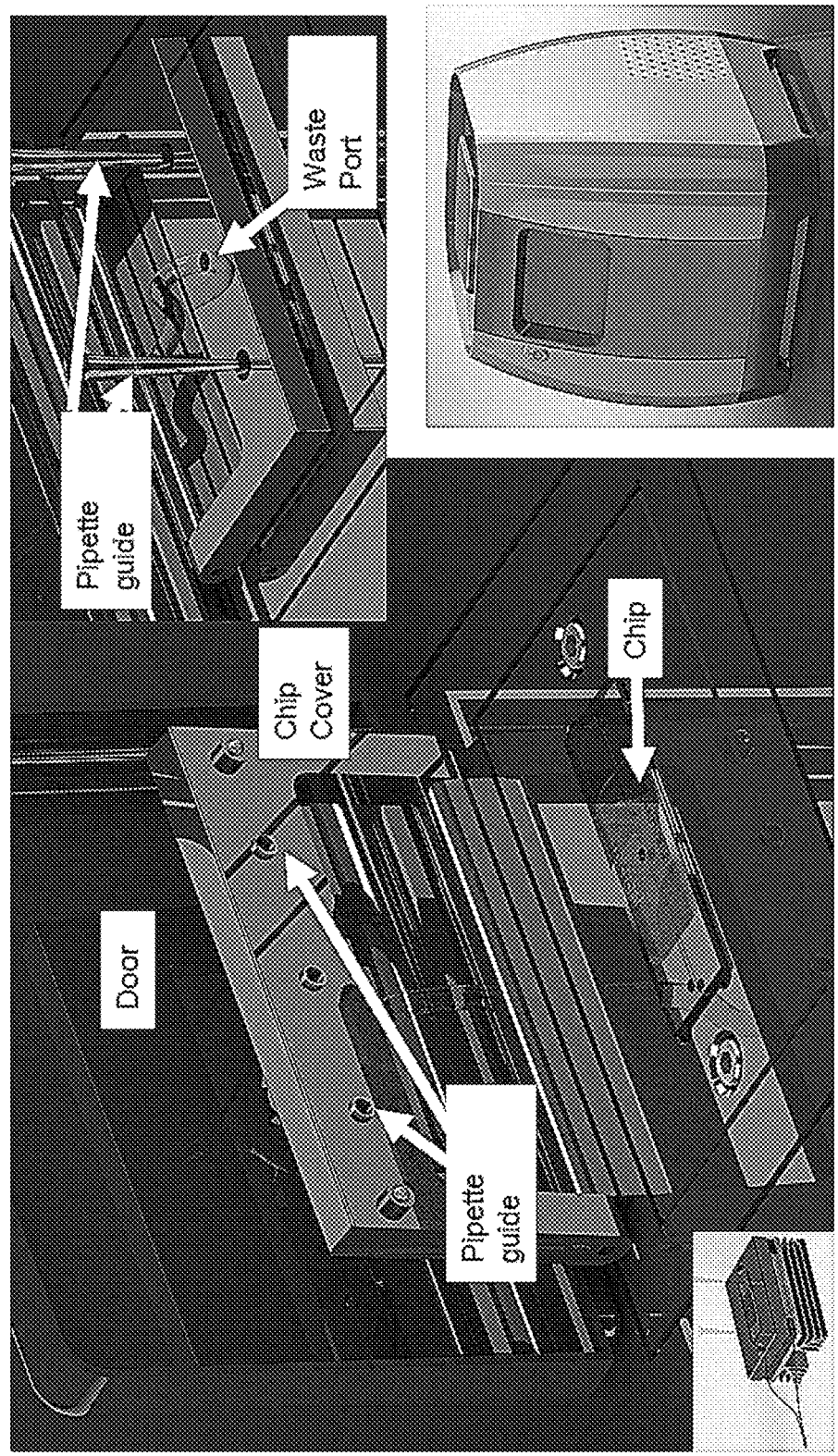
FIG. 4A shows a representative drawing of the single channel sample reference (SCSR) configuration. Representative images of specific components including the hole in the chip (4B), the exit fitting (4C), and the exit tube (4D) are also shown.
Figure 4B:
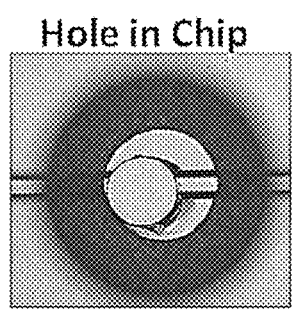
Figure 4C:
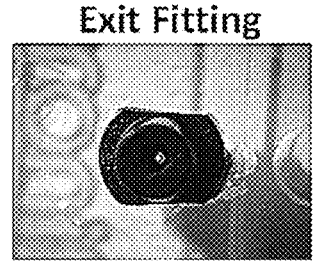
Figure 4D:
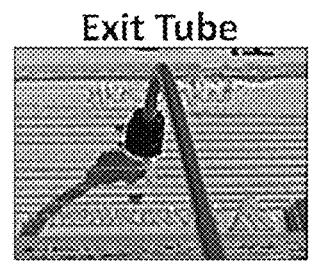

In the single channel sample reference (SCSR) configuration (FIG. 3), a collimated laser beam is expanded, for example, to approximately 8-10 mm, in the axis along the channel, while maintaining the Gaussian shape in the axis perpendicular to the channel. When this beam is impinged onto the microfluidic channel, at least two samples can be interrogated in the channel simultaneously. By separating the samples with either an air gap, a droplet of immiscible material, or other gap or hole in the channel, the samples may be probed in the same channel simultaneously, with the same laser. Thus, the sample and the reference may be interrogated in the same interferometer.

Rapid monitoring and detection of ultra small volume samples is in great demand. One analytical approach, Back-Scattering Interferometry (BSI), derives from the observation that coherent light impinging on a cylindrically shaped capillary produces a highly modulated interference pattern. Typically, BSI analyzes reflections from a capillary tube filled with a liquid of which one wants to measure the refractive index. The technique has been shown capable of measuring changes in refractive index of liquids on the order of $10^{-9}$. The BSI technique is a simple and universal method of detecting refractive index changes in small volumes of liquid and can be applied to monitor changes in concentrations of solutes, flow rates, and temperature, all conducted in nanoliter volumes.

The BSI technique is based on interference of laser light after it is reflected from different regions in a capillary or like sample container. Suitable methods and apparatus are described in U.S. Pat. No. 5,325,170 and WO-A-01/14858, which are hereby incorporated by reference. The reflected or back scattered light is viewed across a range of angles with respect to the laser light path. The reflections generate an interference pattern that moves in relation to such angles upon changing refractive index of the sample. The small angle interference pattern traditionally considered has a repetition frequency in the refractive index space that limits the ability to measure refractive index to refractive index changes causing one such repetition. In one aspect, such refractive index changes are typically on the order of three decades. In another aspect, such changes are on the order of many decades. In another aspect, the fringes can move over many decades up to, for example, the point where the refractive index of the fluid and the channel are matched.

BSI methods direct a coherent light beam along a light path to impinge on a first light transmissive material and pass there through, to pass through a sample which is to be the subject of the measurement, and to impinge on a further light transmissive material, the sample being located between the first and further materials, detecting reflected light over a range of angles with respect to the light path, the reflected light including reflections from interfaces between different substances including interfaces between the first material and the sample and between the sample and the further material which interfere to produce an interference pattern comprising alternating lighter and darker fringes spatially separated according to their angular position with respect to the light path, and conducting an analysis of the interference pattern to determine there from the refractive index, wherein the analysis comprises observation of a parameter of the interference pattern which is quantitatively related to sample refractive index dependent variations in the intensity of reflections of light which has passed through the sample.

The analysis comprises one or both of: (a) the observation of the angle with respect to the light path at which there is an abrupt change in the intensity of the lighter fringes, or (b) the observation of the position of these fringes of a low frequency component of the variation of intensity between the lighter and darker fringes. The first of these (a), relies upon the dependency of the angle at which total internal reflection occurs at an interface between the sample and the further material on the refractive index of the sample. The second (b), relies upon the dependency of the intensity of reflections from that interface on the refractive index as given by the Fresnel coefficients. The rectangular chips, due to corners of the cross section, can also have an additional single component in the diffraction pattern.

The first material and the further material are usually composed of the same substance and may be opposite side walls of a container within which the sample is held or conducted. For instance, the sample may be contained in, e.g. flowed through, a capillary dimensioned flow channel such as a capillary tube. The side wall of the capillary tube nearer the light source is then the "first material" and the opposite side wall is the "further material."

The cross-sectional depth of the channel is limited only by the coherence length of the light and its breadth is limited only by the width of the light beam. Preferably, the depth of the channel is from 1 to 10 μm, but it may be from 1 to 20 μm or up to 50 μm or more, e.g. up to 1 mm or more. However, sizes of up to 5 mm or 10 mm or more are possible. Suitably, the breadth of the channel is from 0.5 to 2 times its depth, e.g., equal to its depth.

Typically, at least one the interfaces involving the sample at which light is reflected is curved in a plane containing the light path, the curved interface being convex in the direction facing the incoming light if it is the interface between the first material and the sample and being concave in the direction facing the incoming light if it is the interface between the sample and the further material. The sample is typically a liquid, and can be flowing or stationary. However, the sample can also be a solid or a gas in various aspects of the present invention. The first and/or further materials will normally be solid but in principle can be liquid, e.g., can be formed by a sheathing flow of guidance liquid(s) in a microfluidic device, with the sample being sheathed flow of liquid between such guidance flows. The sample may also be contained in a flow channel of appropriate dimensions in substrate such as a microfluidic chip. The method may therefore be employed to obtain a read out of the result of a reaction conducted on a "lab on a chip" type of device.

In contrast to conventional BSI techniques, in one aspect the present invention provides systems, apparatuses, and methods to simultaneously or substantially simultaneously measure the refractive index or refractive index related characteristic properties of a sample at multiple points along a single channel, reducing, minimizing, or eliminating variations that can occur when using a separate reference channel. Additionally, the systems, apparatuses, and methods of the present invention are environmentally insensitive. Finally, using a dispersed light beam, measurements can be obtained at multiple discrete zones positioned along the length of the channel, each optionally representing a separate property, chemical interaction, or reference value.

BSI detects changes in the RI between the sample and the reference; therefore, the signal-to-noise (S/N), reproducibility, and overall performance may be impacted by anything that can change the RI. As with temperature, pressure can degrade BSI performance. Indeed a significant degradation of the system performance due to dn/dP sensitivity is a common problem. Changing the pressure results in changes in density, and therefore the RI. The SCSR method attempts to overcome this limitation. The removal of the sample involves evacuation by pressure by opening a valve during the injection/sample introduction process, thereby allowing the system to reach equilibrium with the atmosphere. After each analysis the system is evacuated (both the sample and reference regions), leaving an empty channel that can wick the next set of samples with high efficiency by capillary action. Without wishing to be bound by theory, this technique may allow for both the sample and the reference materials to be introduced without imparting a pressure perturbation.

In various aspects, the inventive interferometric detection system and methods are capable of measuring multiple signals, for example, along a length of a capillary channel, simultaneously or substantially simultaneously. In a further aspect, a plug could be incorporated in the center of the capillary, allowing the sample and the reference to be drawn into the capillary without them coming in contact with each other or mixing. In a still further aspect, two or more capillaries could be used. In yet a further aspect, a tray of capillaries may be used. In an even further aspect, each capillary may be analyzed one at a time. In a still further aspect, more than one capillary may be analyzed at one time.

In a further aspect, and while not wishing to be bound by theory, the refractive index changes that can be measured by the multiplexed interferometric detection systems and methods of the present disclosure can arise from molecular dipole alterations associated with conformational changes of sample-ligand interaction as well as density fluctuations due to changes in waters of hydration. These RI changes also arise from redistribution of the electron density of an ion, atom, or molecule resulting from changes in, for example, sample pH, solvent composition, or molecular interactions.

The detection system has numerous applications, including the observation and quantification of molecular interactions, molecular concentrations, bioassays, universal/RI detection for CE (capillary electrophoresis), CEC (capillary electrochromatography) and FIA (flow injection analysis), physiometry, cell sorting/detection by scatter, ultra micro calorimetry, flow rate sensing, PCR quantification, and temperature sensing. One of the advantages of the systems and methods of the present invention is that a sample measurement and reference measurement can be acquired simultaneously or substantially simultaneously from the same channel. As both measurements occur in the same capillary and, in one aspect, in immediately adjacent portions of the capillary, the thermal properties attributable to each measurement will be uniform, resulting in higher signal to noise levels.

BSI can be operated in either the free-solution or the tethered mode (See, e.g., "Measurement of Monovalent and Polyvalent Carbohydrate-lectin Binding by Back-Scattering Interferometry." A. Kussrow, E. Kaltgrad, M. L. Wolfenden, M. J. Cloninger, M. G. Finn. D. J. Bornhop, *Analytical Chemistry*, 15:81(12): 4889-4897 (2009). PMID: 19462965; and "Comparison of Free-solution and Surface-immobilized Molecular Interactions using a Single Platform, Backscattering Interferometry." I. R. Olmsted, A. Kussrow, and D. J. Bornhop, *Analytical Chemistry*, 84 (24):10817-10822 (2012). PMID:23173653). In the tethered mode, one of the interacting species is immobilized onto the surface of the inner wall of the channel or capillary. Then the sample containing the binding partner can be introduced for binding to the surface bound probe. By simply immobilizing a control adjacent to the detection probe, the difference signal can be obtained using the SCSR.

In various aspects, the detection systems and methods described herein can be useful as a bench-top molecular interaction photometer. In a further aspect, the detection systems and methods described herein can be useful for performing near patient diagnostics. In a still further aspect, the detection system can be useful for performing assays in the field, in the home, in space, or in remote locations.

In various aspects, the detection systems and methods described here can be useful as a hand-held version of BSI.

Thus, in one aspect, the invention fulfills a need for a sensing methodology applicable to micro Total Analysis Systems (µ-TAS) through provision of an interferometric detection system and method that circumvent the drawbacks of conventional interferometric methods and the limitations of the forward scatter technique. The system includes a source of light, an optional optical element capable of at least one of spreading, splitting, rastering, or a combination thereof the light from the light source, a channel of capillary dimensions that is preferably etched or molded in a substrate for reception of a sample to be analyzed, and a photodetector for detecting scattered light from the sample at a detection zone. In various aspects, the light source and the photodetector may be integrated.

1. Using SCSR-BSI

In one aspect, the invention relates to a method for determining a characteristic property of a sample comprising the steps of: (a) providing a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) introducing a first sample into the left side of the channel; (c) introducing a second sample into the right side of the channel; (d) simultaneously interrogating the samples with a light beam, wherein the light beam is elongated in the longitudinal direction of the channel, such that the light beam is incident on at least a portion of the left side of the channel and the right side of the channel; and (e) generating scattered light through reflective and refractive interaction of the light beam with a substrate/channel interface and the samples, the scattered light comprising interference fringe patterns elongated in at least one direction, wherein the interference fringe patterns shift in response to changes in the refractive index of the sample.

It is well known in the art that one of the most challenging aspects of implementing any microfluidic technology, such as BSI, is to overcome the inherent difficulty of injecting or introducing samples (See, e.g., "Microfluidics Toward a Lab-on-a-Chip," Annu. Rev. Fluid Mech. 2004. 36:381-411, doi: 10.1146/annurev.fluid.36.050802.122124; and "Macro-to-micro interfaces for microfluidic devices," Carl K. Fredrickson and Z. Hugh Fan*LabChip, 2004, 4, 526-533). There are many contributing factors here, including the unique properties of the channel such as the small cross section, the unique flow profile of microfluidics, and the physical properties of the sample.

The single channel sample reference (SCSR) configuration utilizes a new sample introduction methodology (FIG. 4A-D), whereby a droplet of the sample is placed in a well at one end of the microfluidic chip, and capillary action serves to pull the material into the interrogating region. An inlet well at each end of the channel and a hole drilled through the center allows for three goals to be accomplished. First, the hole allows air to escape as the sample is pulled in by capillary action, keeping the pressure within the microfluidic channel stable. This is particularly important, because dn/dP (refractive index response to pressure) can be a major source of noise in RI measurements, particularly in systems where the sample volume is constrained or held in a channel which is in poor communication with the local atmosphere (e.g., cannot come to equilibrium after introduction). Second, the hole allows the sample to be removed post measurement by simple vacuum. Third, the hole acts as a barrier for the samples so they do not mix during measurements. Fourth, the hole allows a sample and a reference to be placed at each end of the channel, with both able to be pulled into the chip independently by capillary action, but reaching the same temperature and pressure rapidly. Proper design of the hole or gap to keeps the samples from jumping across the gap, from mixing and to come rapidly to equilibrium. After measurement, it can be important that sample removal be swift and complete. Any sample left over in the channel can contaminate the next sample and hinder smooth capillary action. The use of a switch connected to the tube at the outlet allows the channels to be free in contact with the outside air, but also solidly attached to the vacuum to remove sample.

In various aspects, an inlet may be located at each end of the channel and a single outlet in between. It is also envisioned, however, that the channel may comprise more than two inlets, each with a hole in between them (see, for example, FIG. 5).

Samples also cover a wide range of composition and properties. Some are hydrophobic and some are hydrophilic. They can be aqueous, organic, mixed aqueous-organic and mixed with additives such as salts, surfactants, and acids or bases. Aqueous solutions with surfactant constitute samples that are less hydrophilic than water alone, so dispensing them can be challenging. Samples can contain high concentrations of salt as with buffers, or both buffer salts and surfactant (as required for some protein interaction studies) making them prone to evaporation and changing their capillary action power in glass channels. In this case, the capillary action problem may be overcome by specially coating the injection guide (miscellaneous vendors) to insure wicking into the chip channel. Samples can be sticky, with the matrix and/or samples adhering non-specifically to the introduction guide. Samples such as serum, urine, cells, cell-derived vesicles, tissue-derived vesicles, membrane preps, etc., are particularly challenging. Without wishing to be bound by theory, the approach described herein may enable a minimally trained user to introduce all of these samples with the reproducibility (<2.0 milliradians) required to perform assays and with considerably improved reproducibility.

In a further aspect, the method further comprises the steps of receiving the intensity signals with a signal analyzer and determining therefrom one or more characteristic properties of at least one of the sample.

In a further aspect, the method is performed within a disclosed interferometric detection system. In a still further aspect, the substrate and channel together comprise a capillary tube. In yet a further aspect, the scattered light is backscattered light.

In a further aspect, the light beam is incident on greater than 4 mm of length of the channel in the longitudinal direction. In a still further aspect, the light beam is incident on greater than 4 mm of length of the left side of the channel in the longitudinal direction. In yet a further aspect, the light beam is incident on greater than 4 mm of length of the right side of the channel in the longitudinal direction.

In a further aspect, the first and second samples are introduced substantially simultaneously.

In an alternative aspect, an interferometric detection system can comprise a channel formed in a substrate, wherein the channel has a longitudinal direction and a transverse direction, and wherein the channel is configured for reception of two or more liquid samples by having a separator positioned within the channel, thereby defining a right side of the channel and a left side of the channel, and wherein the right side has a right inlet and a right outlet, and wherein the left side has a left inlet and a left outlet; a light source for generating a light beam, wherein the light beam is elongated in the longitudinal direction of the channel, and wherein the light source is positioned to direct the light beam onto the substrate such that the light beam is simultaneously incident on at least a portion of the right side of the channel and at least a portion of the left side of the channel, such that, during operation, scattered light is generated through reflective and refractive interaction of the light beam with a substrate/channel interface and the two or more samples, the scattered light comprising interference fringe patterns elongated in at least one direction, wherein the interference fringe patterns shift in response to changes in the refractive index of the two or more samples; and a photodetector for simultaneously receiving the scattered light and generating a plurality of intensity signals. Such a system is represented schematically in FIG. 7.

Figures 25A, 25B, 25C:
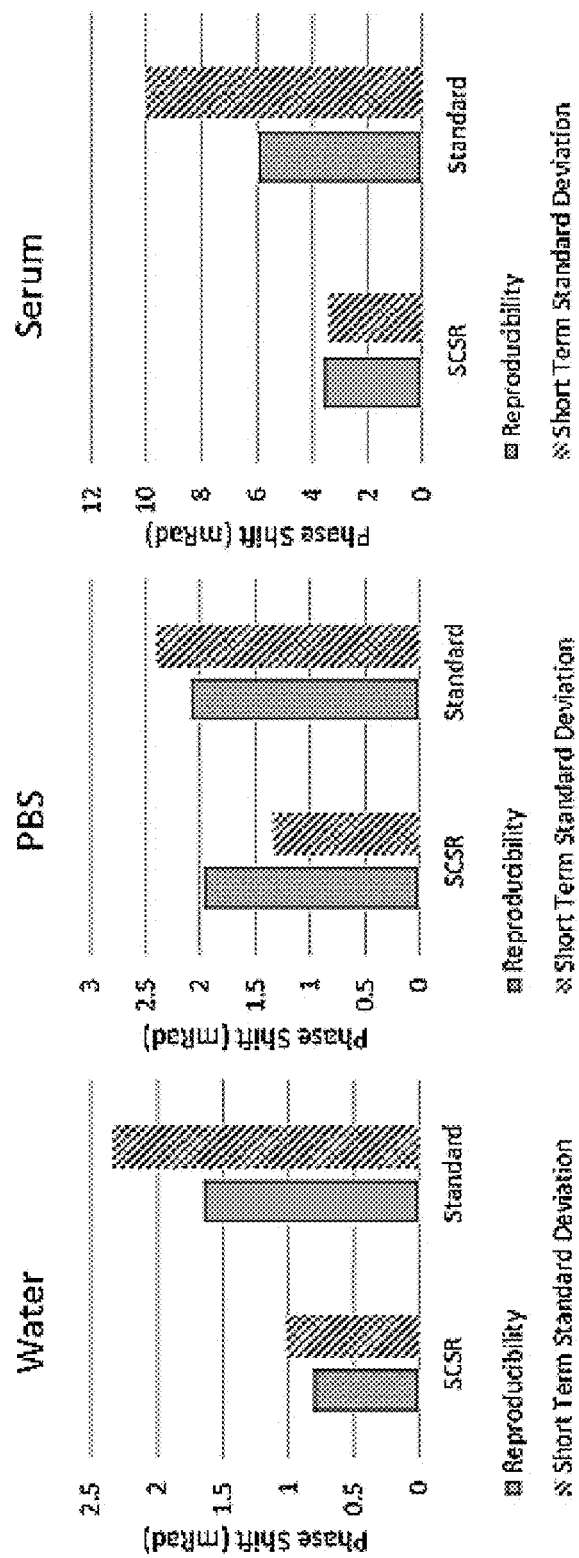
FIG. 25A-C show a representative image illustrating that the injection approach can be used for several matrices, including water (25A), PBS (25B), and serum (25C), and does not require a trained user.

As illustrated in FIG. 25, SCSR BSI provides results superior to those provided by conventional BSI. Both the short Term Standard Deviation and run-to-run (trial-to-trail) reproducibility are plotted for Water, PBS, and 20% Serum. Short term SD corresponds to the baseline noise in radians (milliradians) for a 10 second period collected after injecting the sample of interest. The reproducibility is the standard deviation of average measured phase value for triplicate determinations. In all cased the SCSR performs quantifiably better: 50% for water, PBS about 50% for short term noise, and 40-60% improvement for serum.

2. Interrogation Region Length

In one aspect, the invention relates to a method for determining a characteristic property of a sample comprising the steps of: (a) providing a sample positioned inside a channel formed in a substrate, wherein the channel has a longitudinal direction and a transverse direction; (b) interrogating the sample with a light beam, wherein the light beam is elongated in the longitudinal direction of the channel, such that the light beam is incident on at least a portion of the channel greater than 4 mm in length along the longitudinal direction; and (c) generating scattered light through reflective and refractive interaction of the light beam with a substrate/channel interface and the sample, the scattered light comprising interference fringe patterns elongated in at least one direction, wherein the interference fringe patterns shift in response to changes in the refractive index of the sample.

Averaging over a length of the channel provides fringes that line up better between two regions, are closer in shape, provide better compensation, and are more Gaussian. Increasing the length of the channel allows for more fringes to be averaged. Thus, averaging over a greater length of the channel decreases the variation of the fringes acquired.

In various aspects, the light beam may be elongated to take more measurements, e.g., by spreading the light in the direction of the sample and/or reference, and then averaging the data. This technique serves to increase the S/N ratio. In this way, a single measurement may provide data comparable to taking multiple measurements.

In various aspects, the light beam is incident on greater than 4 mm of length of the channel in the longitudinal direction. In a further aspect, the light beam is incident on greater than 5 mm of length of the channel in the longitudinal direction. In a still further aspect, the light beam is incident on greater than 6 mm of length of the channel in the longitudinal direction. In yet a further aspect, the light beam is incident on greater than 7 mm of length of the channel in the longitudinal direction. In an even further aspect, the light beam is incident on greater than 8 mm of length of the channel in the longitudinal direction. In a still further aspect, the light beam is incident on greater than 9 mm of length of the channel in the longitudinal direction. In yet a further aspect, the light beam is incident on greater than 10 mm, 12 mm, 14 mm, 16 mm, 18 mm, or 20 mm of length of the channel in the longitudinal direction.

In a further aspect, the method further comprises the steps of receiving the intensity signals with a signal analyzer and determining therefrom one or more characteristic properties of at least one of the sample.

In a further aspect, the method is performed within a disclosed interferometric detection system. In a still further aspect, the substrate and channel together comprise a capillary tube. In yet a further aspect, the scattered light is backscattered light.

3. Averaging Over Length of the Channel, High Frequency Noise and Nyquist Sampling Theory Without wishing to be bound by theory, Nyquist sampling theory states that in measuring any continuous signal whose Fourier transform is zero outside of a finite region of frequencies (meaning the function is band limited), the signal can be sampled with perfect fidelity by sampling at twice the highest frequency present in the signal. When this criterion cannot be met, aliasing happens, and the high frequencies interfere with the interpretation of the lower frequency components present in the signal. In the real world, signals are rarely band limited, so sampling a continuous analog signal can result in the introduction of noise due to the failure to satisfy this criterion. Increasing the sampling rate can decrease this noise, but the less high frequency signal present, the less this will affect the signal. It can thus be desirable to decrease any unnecessary high frequencies present in an analog signal before sampling, in order to decrease noise introduced during the discretization and Fourier processes.

Figure 26B:
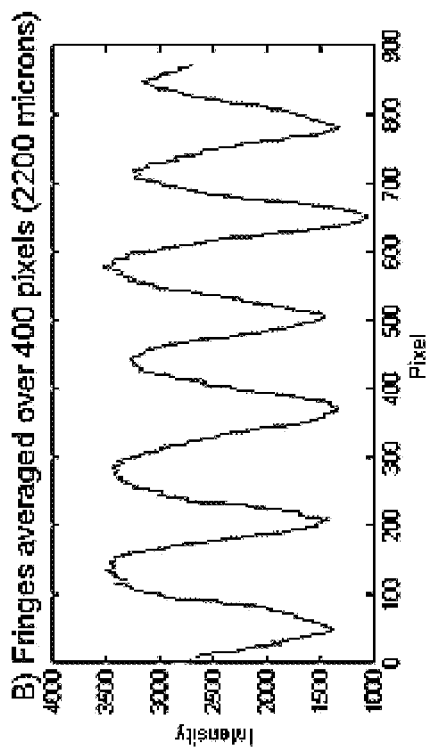
FIG. 26A-D show graphs explaining that averaging over the length of the channel can make the fringes more uniform and more Gaussian and can decrease the amount of high frequency information present in the analog fringe signal. Specifically.
Figure 26D:
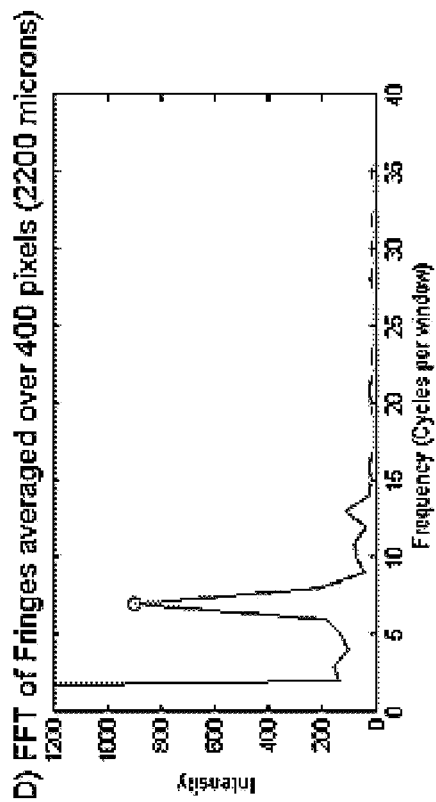
Figure 26A:
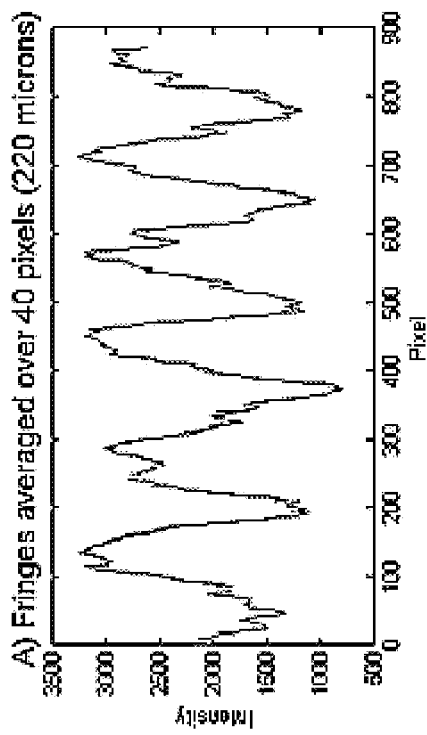
Figure 26C:
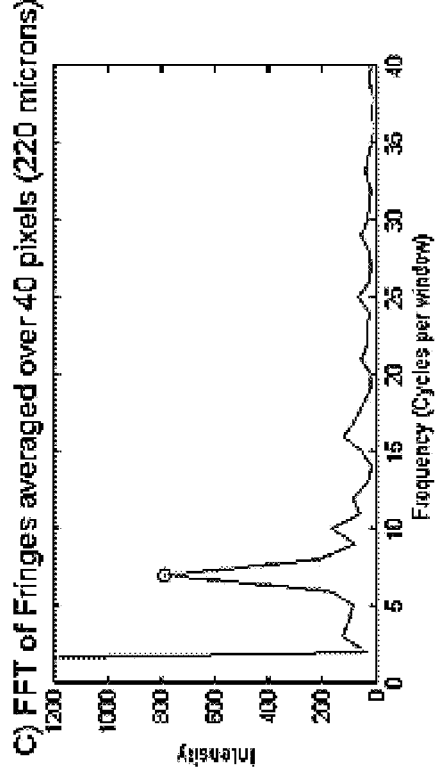
Figure 27:
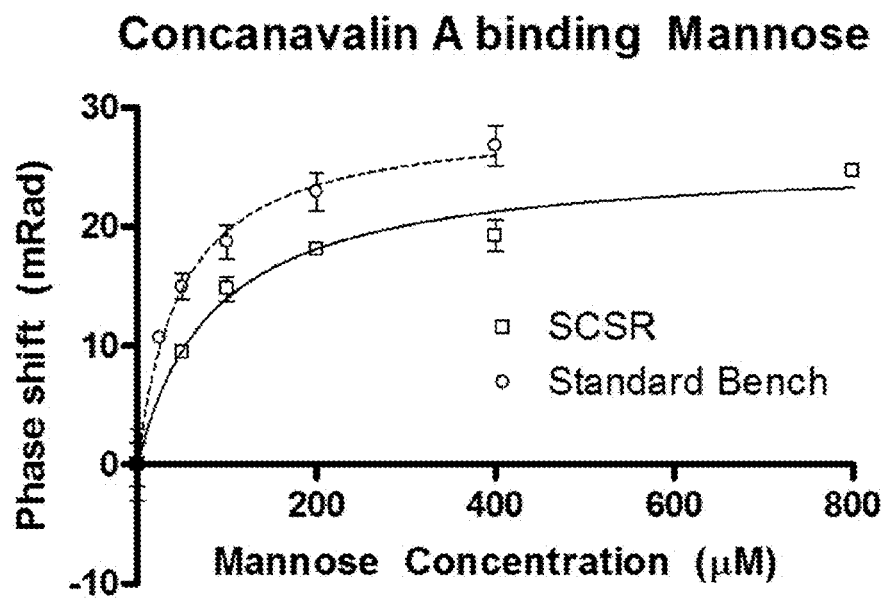
FIG. 27 shows BSI can measure free solution interactions on systems that have a large mass differences (e.g., conA and sugar) and that SCSR can works better than the conventional BSI instruments (see error bars) even when used without temperature control.

Averaging over the length of the channel (i.e., a longer interrogation region length) can make the fringes more uniform and more Gaussian and can decrease the amount of high frequency information present in the analog fringe signal. FIG. 26A shows the fringes when averaged over 220 microns, and FIG. 26B shows those same fringes averaged over 2200 microns. The Fourier transforms of these fringes are shown in FIG. 26C and FIG. 26D, respectively. In this particular alignment, one would be examining frequency 7 (indicated in the FFT with a circle). When using BSI to conduct an assay, best results can be found when a single spatial frequency is present in the fringe pattern impinging upon the photodetector (e.g., camera). The degree of unity of the single spatial frequency can be assessed by calculating the ratio of the desired frequency (in this example, 7) to the nearest two frequencies (6 and 8). A high ratio indicates that the majority of the signal present in the fringe pattern is a single spatial frequency. In this example, the ratio of Frequency 7 to Frequencies 6 and 8 is 8.2 in FIG. 26C (220 microns) and 9.1 in FIG. 26D (2200 microns). This indicates that, in this case, there is a gain a 10% increase in fringe uniformity by averaging over the channel.

The high frequency noise present in the signal can be quantified as the intensity of the FFT for all frequencies greater than the desired frequency. To obtain a relative comparison of the high frequency noise between the two lengths of channels averaged, the FFT intensity was integrated from just above the desired frequency (10) to the highest calculated Frequency (871). The integrated intensity value for the 220 micron fringes is 3449.7, and for the 2200 micron fringes is 2220.5. This correlates to a large reduction (roughly 40%) in high frequency noise present in the fringe pattern, obtained by averaging over a longer length of the channel.

This indicates that one can sample fringe pattern by placing the fringes upon a camera with pixels of a certain size. The spatial sampling rate can be determined by the size of the pixels on the camera and the distance the camera sits from the microfluidic chip. Because the fringes are projected radially, the physical size of the fringes increases as the camera moves farther from the chip. A standard camera (Ames Garry/Larry) can have, for example, 3000 pixels, and typically 7 fringes are interrogated. This yields a spatial sampling rate of about 430 pixels per fringe. When a camera is moved closer to the channel, in certain aspects, up to 60 fringes can be captured, which means that the spatial sampling rate becomes about 50 pixels per fringe. Thus, moving the camera closer to the microfluidic chip, can sacrifice spatial sampling rate. This indicates that when there is a lot of high frequency information present in the fringes, one will get higher levels of noise. By averaging over a longer length of the channel and decreasing the amount of high frequency noise present in the analog signal, the necessary spatial sampling rate is decreased, allowing one to move the camera much closer to the microfluidic chip without sacrificing signal fidelity.

4. Photodetector Integration Dimensions

In one aspect, the invention relates to methods for determining a characteristic property of a sample comprising the steps of: (a) providing a sample positioned inside a channel formed in a substrate, wherein the channel has a longitudinal direction and a transverse direction; (b) interrogating the sample with a light beam, wherein the light beam is elongated in the longitudinal direction of the channel, wherein the photodetector is positioned less than 40 cm from the channel during interrogation; and (c) generating scattered light through reflective and refractive interaction of the light beam with a substrate/channel interface and the sample, the scattered light comprising interference fringe patterns elongated in at least one direction, wherein the interference fringe patterns shift in response to changes in the refractive index of the sample.

Optimum photodetector integration dimensions is dependent on chip configurations (e.g., chip material, substrate and top plate thickness, channel dimensions, shape, etc.) and the distances from the channel (e.g., chip top) surface to the camera sensor. Thus, in various aspects, the photodetector is positioned less than about 40 cm (e.g., less than about 36 cm, less than about 32 cm, less than about 30 cm, less than about 28 cm, less than about 26 cm, less than about 24 cm, less than about 22 cm, less than about 20 cm, less than about 18 cm, less than about 16 cm, less than about 14 cm, less than about 12 cm, less than about 10 cm, less than about 9 cm, less than about 8 cm, less than 7 cm, less than about 6 cm, less than about 5 cm, less than about 4 cm, less than about 3 cm, less than about 2 cm, less than about 1 cm) from the channel during interrogation. For example, the photodetector can be positioned from about 2 cm to about 40 cm, from about 2 cm to about 20 cm, from about 2 cm to about 10 cm, from about 5 cm to about 20 cm, from about 5 cm to about 10 cm, from about 5 cm to about 40 cm, from about 10 cm to about 40 cm, from about 10 cm to about 30 cm, or from about 5 cm to about 30 cm from the channel during interrogation.

The camera resolution, including pixel size, spacing, and photon flux sensitivity, must also conform to a minimum specification. Thus, in various aspects, between about 30 camera pixels and 500 camera pixels may be interrogated. In a further aspect, between about 30 camera pixels and 350 camera pixels may be interrogated. In a still further aspect, between about 30 camera pixels and 300 camera pixels may be interrogated. In yet a further aspect, between about 30 camera pixels and 250 camera pixels may be interrogated. In an even further aspect, between about 30 camera pixels and 200 camera pixels may be interrogated. In a still further aspect, between about 30 camera pixels and 150 camera pixels may be interrogated. In yet a further aspect, between about 50 camera pixels and 100 camera pixels may be interrogated. In an even further aspect, between about 100 camera pixels and 500 camera pixels may be interrogated. In a still further aspect, between about 150 camera pixels and 500 camera pixels may be interrogated. In yet a further aspect, between about 200 camera pixels and 500 camera pixels may be interrogated. In an even further aspect, between about 250 camera pixels and 500 camera pixels may be interrogated. In a still further aspect, between about 300 camera pixels and 500 camera pixels may be interrogated.

This optical configuration may allow for several advantages. For example, the effect of air currents and temperature perturbations may be reduced thereby decreasing environmental noise. Additionally, averaging over a greater number of pixels may allow for improved compensation and more Gaussian shaped fringes.

In various aspects, the light beam is incident on at least a portion of the channel greater than 4 mm in length along the longitudinal direction. In a further aspect, the light beam is incident on at least a portion of the channel greater than 5 mm of length of the channel in the longitudinal direction. In a still further aspect, the light beam is incident on at least a portion of the channel greater than 6 mm of length of the channel in the longitudinal direction. In yet a further aspect, the light beam is incident on at least a portion of the channel greater than 7 mm of length of the channel in the longitudinal direction. In an even further aspect, the light beam is incident on at least a portion of the channel greater than 8 mm of length of the channel in the longitudinal direction. In a still further aspect, the light beam is incident on at least a portion of the channel greater than 9 mm of length of the channel in the longitudinal direction. In yet a further aspect, the light beam is incident on at least a portion of the channel greater than 10 mm of length of the channel in the longitudinal direction.

In a further aspect, the method further comprises the steps of receiving the intensity signals with a signal analyzer and determining therefrom one or more characteristic properties of at least one of the sample.

In a further aspect, the method is performed within a disclosed interferometric detection system. In a still further aspect, the substrate and channel together comprise a capillary tube. In yet a further aspect, the scattered light is backscattered light.

5. Using Multiple Elements

In one aspect, the invention relates to a method for determining a characteristic property of a sample comprising the steps of: (a) providing a channel formed in a substrate, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel and a left side of the channel; (b) introducing a first sample into the left side of the channel and then closing the inlet of the left side of the channel with a first closure element, thereby reducing evaporation of the first sample; (c) introducing a second sample into the right side of the channel and then closing the inlet of the right side of the channel with a second closure element, thereby reducing evaporation of the second sample; (d) simultaneously interrogating the samples with a light beam, wherein the light beam is elongated in the longitudinal direction of the channel, such that the light beam is incident on greater than 4 mm of length of the channel in the longitudinal direction and simultaneously incident on at least a portion of the left side of the channel and at least a portion of the right side of the channel, wherein the photodetector is positioned less than 40 cm from the channel during interrogation; and (e) generating scattered light through reflective and refractive interaction of the light beam with a substrate/channel interface and the samples, the scattered light comprising interference fringe patterns elongated in at least one direction, wherein the interference fringe patterns shift in response to changes in the refractive index of the sample.

In a further aspect, the method further comprises the steps of receiving the intensity signals with a signal analyzer and determining therefrom one or more characteristic properties of at least one of the sample.

In a further aspect, the method is performed within a disclosed interferometric detection system. In a still further aspect, the substrate and channel together comprise a capillary tube. In yet a further aspect, the scattered light is backscattered light.

In a further aspect, the light beam is incident on greater than 4 mm of length of the channel in the longitudinal direction. In a still further aspect, the light beam is incident on greater than 4 mm of length of the left side of the channel in the longitudinal direction. In yet a further aspect, the light beam is incident on greater than 4 mm of length of the right side of the channel in the longitudinal direction.

E. Methods of Improving Precision

In one aspect, the invention relates to a method of improving precision when determining a characteristic property of a sample, the method comprising the step of: (a) introducing a sample into an inlet of a channel formed in a substrate; and (b) closing the inlet with a closure element, thereby reducing evaporation of liquid positioned within the channel and/or inlet.

In a further aspect, closing is via friction fit. In a still further aspect, closing is via screw fit.

In a further aspect, the method further comprises the step of performing interferometric analysis.

In a further aspect, the substrate and channel together comprise a capillary tube.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Binding Measurements with Small Molecular Weight Ligands

Figure 8:
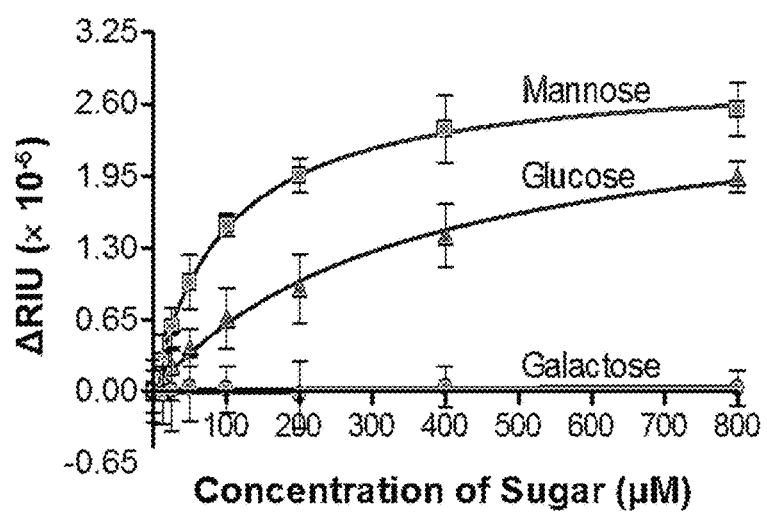
FIG. 8 shows representative data pertaining to the ability of BSI to quantify the affinity for a >100 kDa protein binding to small molecules (<200 Da) in free-solution.
Figure 9:
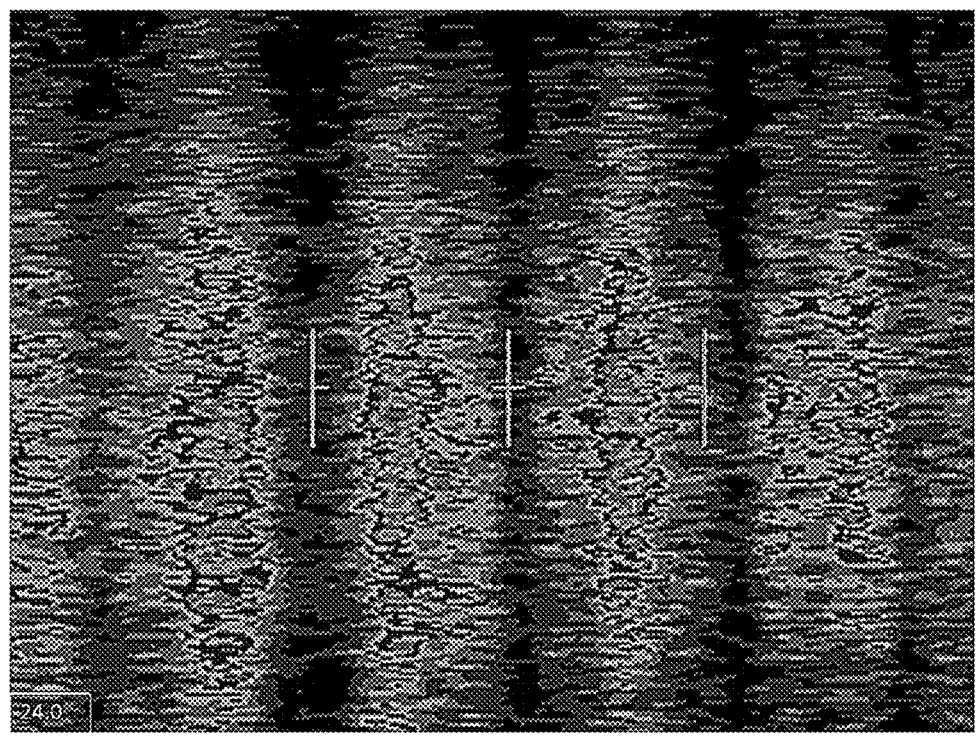
FIG. 9 shows a representative image illustrating that stretched fringes interrogate a 10 mm length of the chip in the SCSR optical train.
Figure 10A:
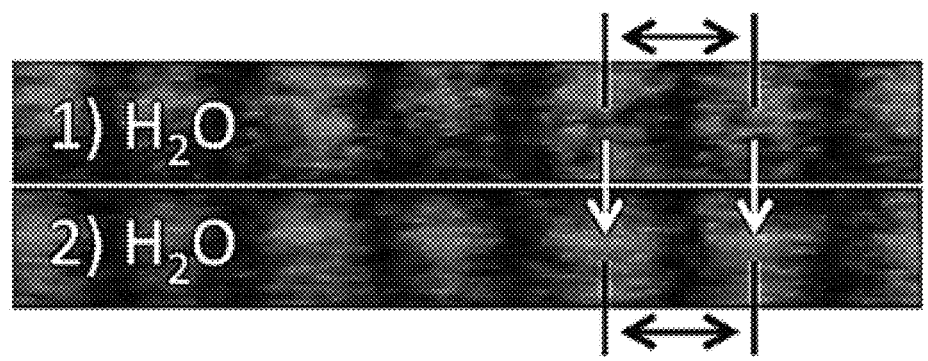
FIGS. 10A and 10B show representative images illustrating the SCSR fringe shift observed due to change in refractive index. Referring to 10A, A1 and A2 show the fringes resulting from water in both sides of the channel. Referring to 10B, B1 shows fringes from water in the reference channel and B2 shows fringes from 10% methanol.
Figure 10B:
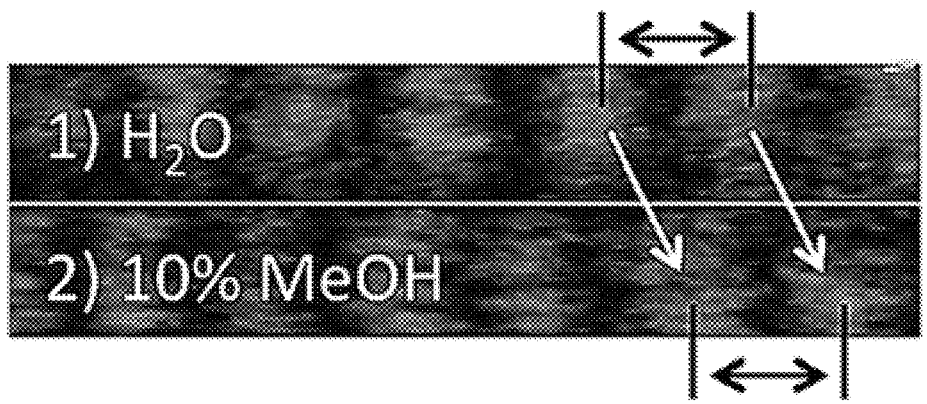

A major advantage of BSI over other label-free biosensors is its ability to detect small molecule binding to large proteins in a simple, homogenous, end-point interaction assay in a mass-independent manner. This independence is illustrated in FIG. 8, showing a binding assay lectin Concanavalin A (ConA), a >100 kDa molecular weight protein, and two different monosaccharides (MW<200 Da) measured in free-solution. The equilibrium $K_D$ was measured to be 96 µM for mannose and 344 µM for glucose ("Comparison of Free-solution and Surface-immobilized Molecular Interactions using a Single Platform, Backscattering Interferometry." I. R. Olmsted, A. Kussrow, and D. J. Bornhop, Analytical Chemistry, 84 (24):10817-10822 (2012). PMID: 23173653). A non-binding sugar, galactose, was used as the control and showed no binding signal, illustrating the specificity of the BSI binding measurements. It is appreciated that the foregoing technique can be performed in combination with the techniques disclosed herein—including single-channel-sample-reference (SCSR), use of a closure element, and/or longer interrogation region length—which is expected to provide superior results, including improved sensitivity and/or decreased noise.

2. Small Molecule Ligands Binding to Native Cell Membrane Receptors in Free-Solution Membrane-associated proteins and their interactions are of paramount interest in the design of clinical therapeutics, accounting for almost 70% of existing drug candidate targets (Krummel and Davis (2002) *Current Opinion in Immunology* 14: 66-74; Overington et al. (2006) *Nature Reviews Drug Discovery* 5: 993-996). To date, it has been difficult to perform direct binding assays on cellular membranes except by down-stream signal transduction or the use of isotope labeling methods. BSI facilitated label-free, free solution binding assays on proteoliposomes (Bracey et al. (2002) *Science* 298: 1793-1796; Jass et al. (2000) *Biophysical Journal* 79: 3153-3163) from full-length, functional membrane proteins, from both natural and recombinant sources (Kussrow et al. (2010) *Chembiochem* DOI: 10.1002/cbic.201000671).

Three events were investigated: A) the transmembrane protein fatty acid amide hydrolase (FAAH) (Bracey et al. (2002) *Science* 298: 1793-1796; Cravat et al. (1995) *Science* 268: 1506-1509; Devane et al. (1992) *Science* 268: 1506-1509) incorporated into small unilamellar vesicles (SYV's) and binding to several small molecule inhibitors (OL-135, JGII-145, and FAR-1-216); B) the CXCR4 receptor binding the stromal cell-derived factor 1α; and C) a difficult to isolate and purify target, the heterodimeric (Pin et al. (2004) *Pharmacology* 68: 1565-1572) γ-amino-butyric acid (GABA) receptor (Urwyler et al. (2001) *Molecular Pharmacology* 60: 963-971) binding to several small molecule ligand (R-baclofen, GABA, SKF-97541, and CGP-54626). GABA was studied directly as intact membranes from Chinese Hamster Ovary (CHO) cells genetically modified to overexpress the B(1b) and B2 components of the $GABA_B$ receptor. In all cases, plots of signal vs. concentration of ligand gave sigmoidal curves that fit well to a simple single-site binding model resulting in equilibrium binding constants which are quite comparable to reported values (Boger et al. (2005) *J. Med. Chem.* 48: 1849-1856; Froestl et al. (1995) *J. Med. Chem.* 38: 3297-3312; Garfunkle et al. (2008) *J. Med. Chem.* 51: 4392-4403; Kaupmann et al. (1997) *Nature* 386: 239-246; Romero et al. (2007) *J. Med. Chem.* 50: 1058-1068). Little or no BSI signal was observed for even the highest concentrations of a negative control compound (L-alanine and cholesterol); again showing that the BSI signal reflects specific interactions. It is appreciated that the foregoing technique can be performed in combination with the techniques disclosed herein—including single-channel-sample-reference (SCSR), use of a closure element, and/or longer interrogation region length—which is expected to provide superior results, including improved sensitivity and/or decreased noise.

3. Small Molecule—Protein Interactions in Aqueous-DMSO Solvent

BSI is proving to be particularly attractive in the drug discovery sector, where small molecule-protein interactions are the most common drug candidate. Drug discovery determinations are typically done using cell-based assays (Minor (2008) *Combinatorial Chemistry & High-Throughput Screening* 11: 573-580), typically followed by biophysical measurements like SPR to further characterize "hits." However, SPR is relatively expensive, requires immobilization protocols, and does not work with some systems.

End-point binding assays were performed on a well-characterized enzyme-inhibitor system, carbonic anhydrase II (CAII), and five small inhibitor molecules in solutions containing at least 1% DMSO (Morcos et al. (2010) *Electrophoresis* 31: 3691-3695) (data not shown). Inhibitors of CAII are used to treat glaucoma and epilepsy and drugs targeting CAII may lead to treatments of cancer and obesity (Cecchi et al. (2005) *Bioorganic & Medicinal Chemistry Letters* 15: 5192-5196). These results mirror those performed by SPR (Papalia et al. (2006) *Analytical Biochemistry* 359: 94-105; Day et al. (2002) *Protein Science* 11: 1017-1025), benchmarking BSI. It is appreciated that the foregoing technique can be performed in combination with the techniques disclosed herein—including single-channel-sample-reference (SCSR), use of a closure element, and/or longer interrogation region length—which is expected to provide superior results, including improved sensitivity and/or decreased noise.

4. Temperature Insensitivity of Single Channel Sample Reference

Figure 11:
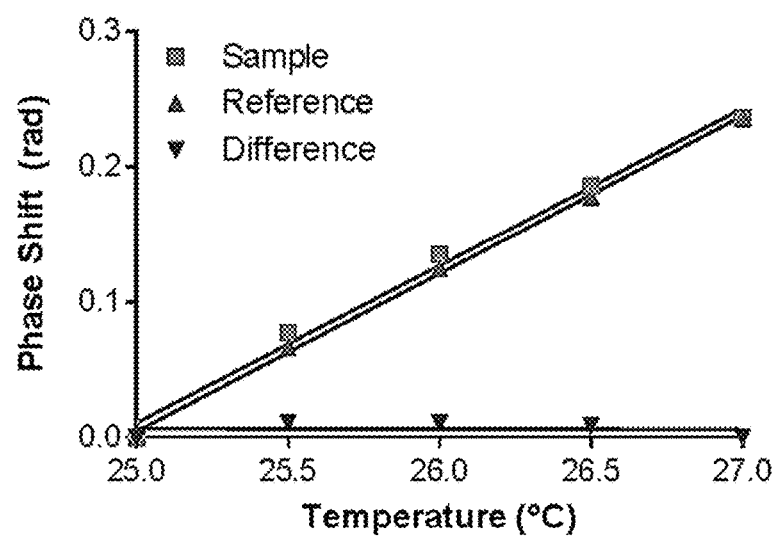
FIG. 11 shows representative data illustrating the temperature compensation possible using the SCSR-BSI approach. This experiment was performed using a capillary tube as the channel.
Figure 12B:
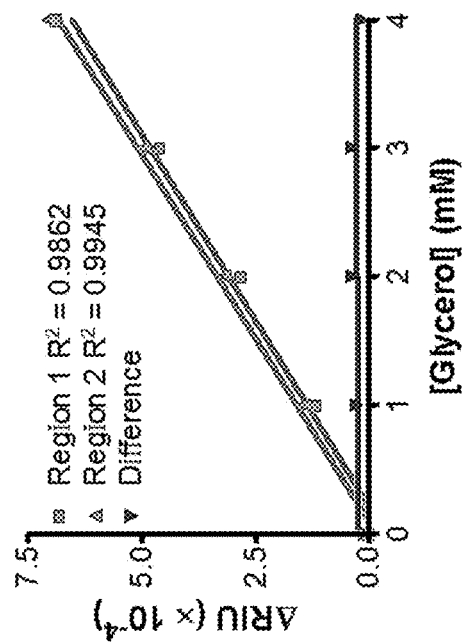
FIG. 12A-C show representative data demonstrating that SCSR-BSI compensates for very large temperature changes (12A), for environmental perturbations (12B), and gives a 0.7 µRIU response (12C). These experiments were performed using a microfluidic channel.
Figure 12A:
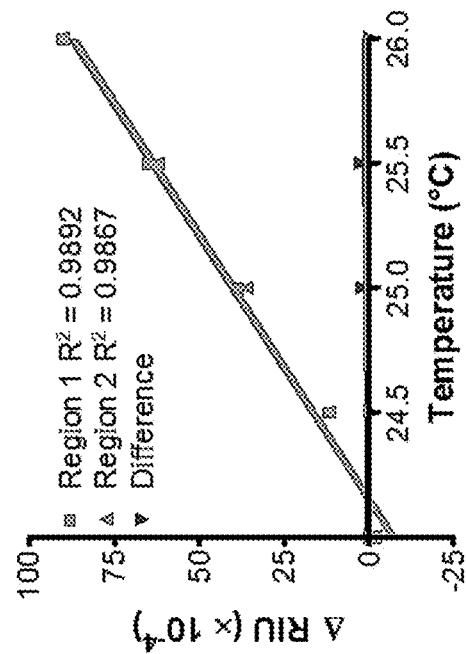

Temperature sensitivity has historically limited RI detection methods from being deployed in diverse settings. In the SCSR configuration a 2D CCD array is used to capture the fringes from the (both) regions with one camera, so measurements occur simultaneously. The initial embodiment of this approach (capillary tube) facilitated very good compensation (FIG. 11). The SCSR approach was initially tested by changing the chip temperature by 0.5° C. increments, a total of $5 \times 10^{-4}$ µRIU, and measuring the signal in the two regions of an elongated fringe (FIG. 3), with the difference signal plotted using the upside down triangles (FIG. 12A). Both regions responded similarly, allowing temperature-induced RI changes to be effectively compensated (~7 µRIU).

In the second test, the same analyte concentrations were introduced adjacent to each other, sequentially, and the difference was measured to evaluate relative response and absolute compensation. This experiment, done in triplicate, reports the minimum resolvable signal change or limit of detection (LOD) of $1.1 \times 10^{-8}$ RIU (ca. 10-fold improvement) (FIG. 12B) and shows that adjacent regions have similar RI response.

Figure 12C:
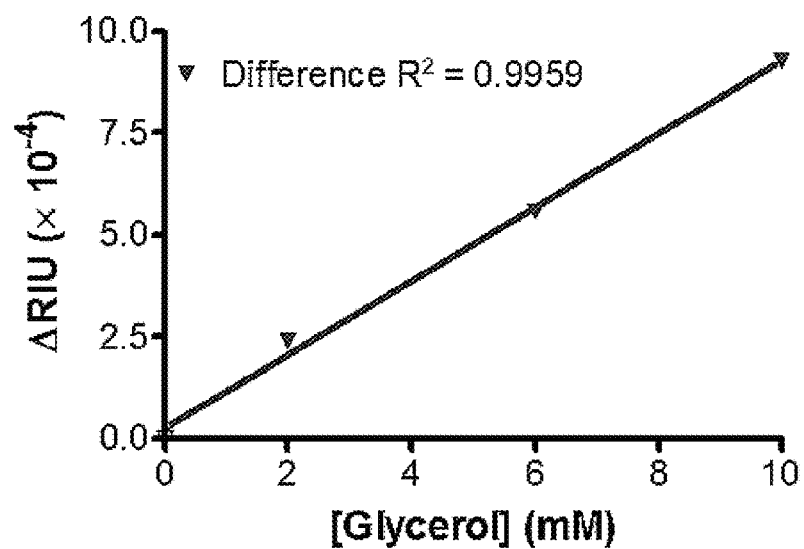

Finally, glycerol calibration measurements were performed (FIG. 12C). The sample (glycerol solution) and the PBS buffer used to prepare the sample (blank) were introduced into the channel, separated by a small air gap. Response was linear and the detection limits for a true sample-reference determination, without temperature control, was $7 \times 10^{-7}$ RIU. Without wishing to be bound by theory, it is anticipated that the SCSR approach may provide excellent data not only when the limit of quantitation (LOQ) is 2 µRIU or 0.7 µRIU, but also 0.5 µRIU or better.

5. Implementation of a Single-Channel, Sample-Reference (SCSR) BSI

Figure 14:
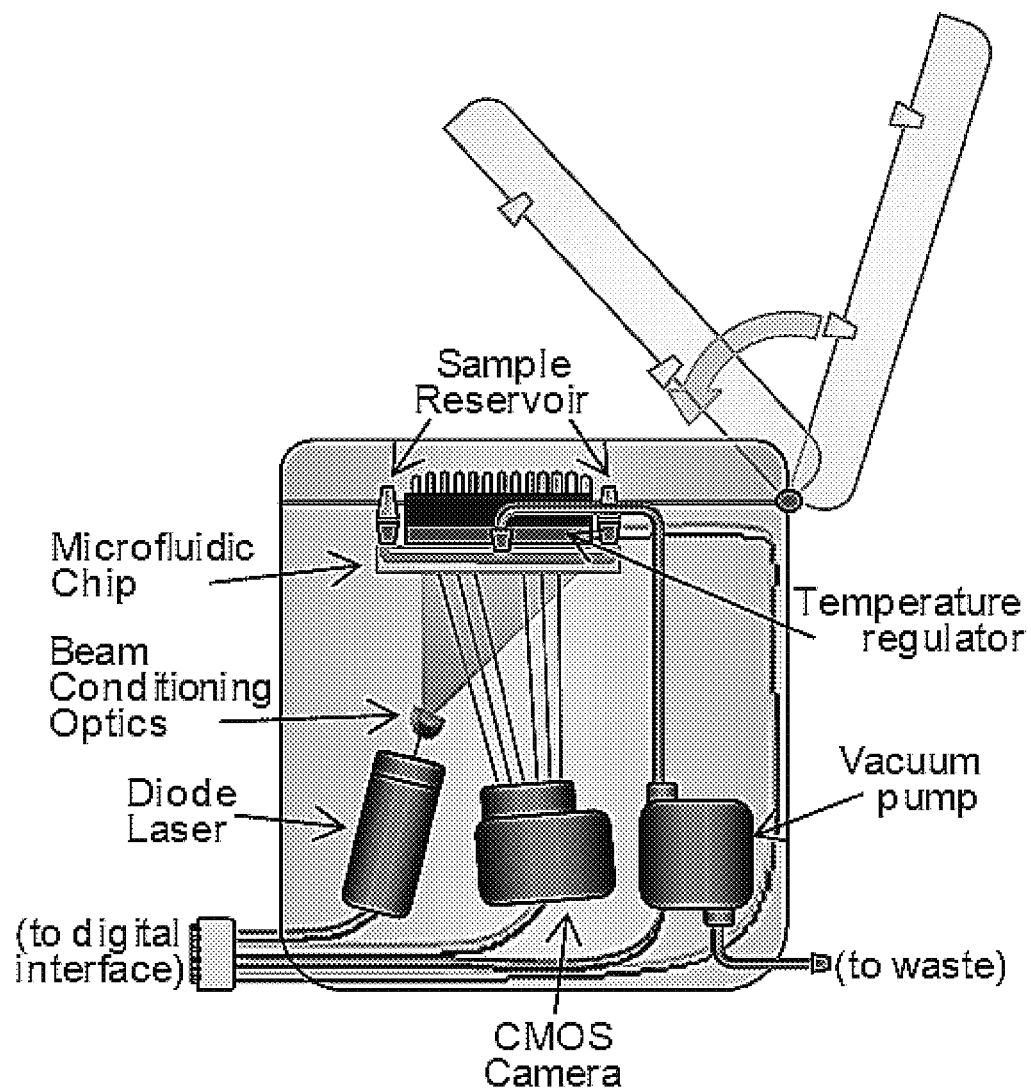
FIG. 14 shows a representative schematic of the NanoBIND illustrating the inverted optical train.

In this case, the sample-reference advantage was realized by expanding the laser beam along with the channel axis (~6-10 mm), allowing the interrogation of neighboring regions of fluid to be examined simultaneously within the same channel (FIG. 14). Interrogating a single-channel with an elongated beam provides extraordinary temperature compensation, excellent detection limits, and is considerably easier to align than a two-channel, two beam configuration. Because a channel has relatively uniform optical properties, the samples to be compared are contained in nearly identical interferometers, as opposed to the two beam approach where they are interrogated by different beams in different channels spaced 1 mm apart. Maximum specificity is also insured since direct comparison of the sample and blank (or control) is done in essentially the same interferometer because both are in the same channel within the chip.

6. Effect of Temperature on Single Channel Sample Reference

Figure 15:
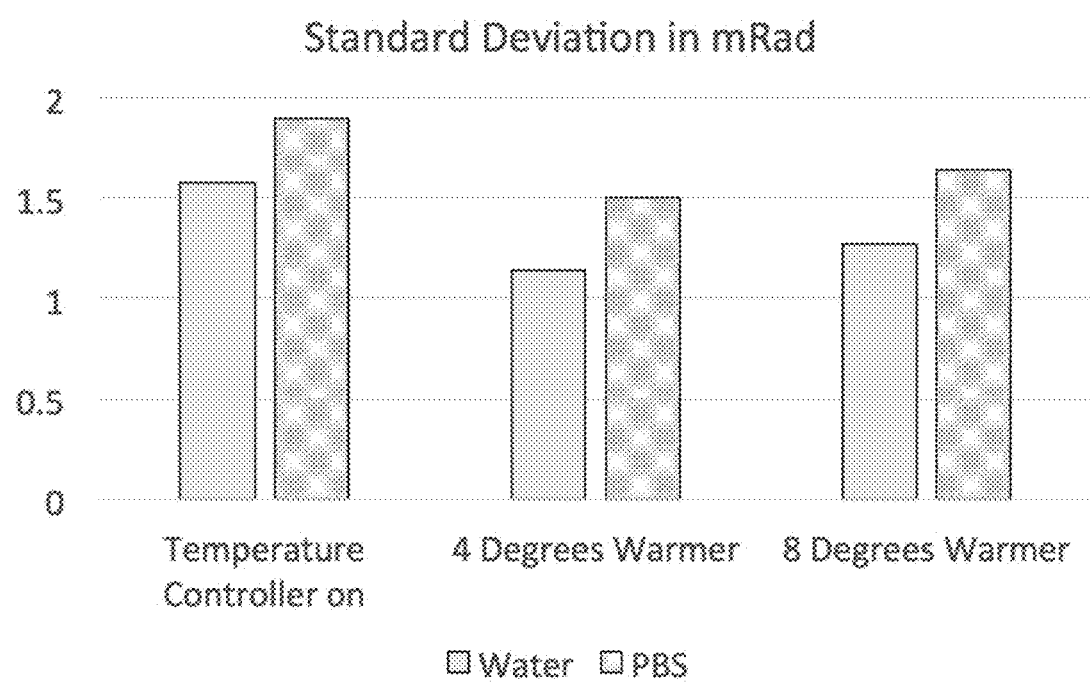
FIG. 15 shows representative data pertaining to the effect of changes in ambient temperature on the baseline standard deviation for the SCSR and the standard interferometer configuration.

Water was injected into each side of the single channel sample reference, and the phase was read over 5 minutes for each of the following conditions. To change the ambient temperature, hot plate was placed next to the interferometer, and a cardboard box was placed over both the instrument and the hot plate. The ambient temperature in the room was 21° C. The instrument had a lower baseline noise with the temperature controller off, and there was very little increase to the baseline noise with the increase in ambient temperature. The standard deviation of the baseline signal over 5 minutes for both water and phosphate buffered saline (PBS) at three different ambient temperatures is illustrated in FIG. 15 and Table 2. Evaporation caused the PBS to have a higher baseline noise over the course of measurement.

TABLE 2

|  | Water | PBS |
| --- | --- | --- |
| Temperature Controller On | 1.574 | 1.900 |
| 4 degrees warmer | 1.143 | 1.502 |
| 8 degrees warmer | 1.270 | 1.641 |

Figure 16A:
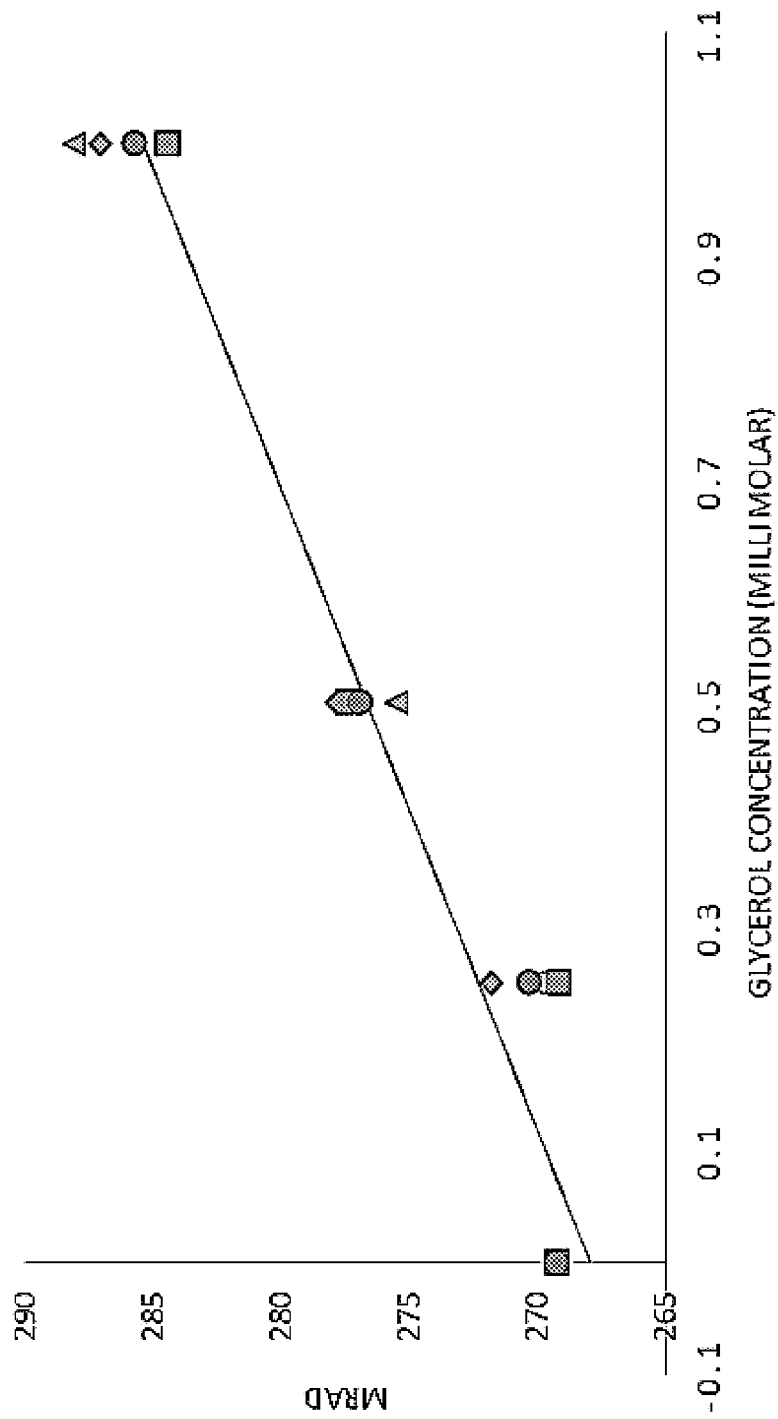
FIGS. 16A and 16B show representative data pertaining to the effect of temperature on triplicate glycerol calibration runs using the SCSR configuration (16A) and the standard interferometer configuration (16B).
Figure 16B:
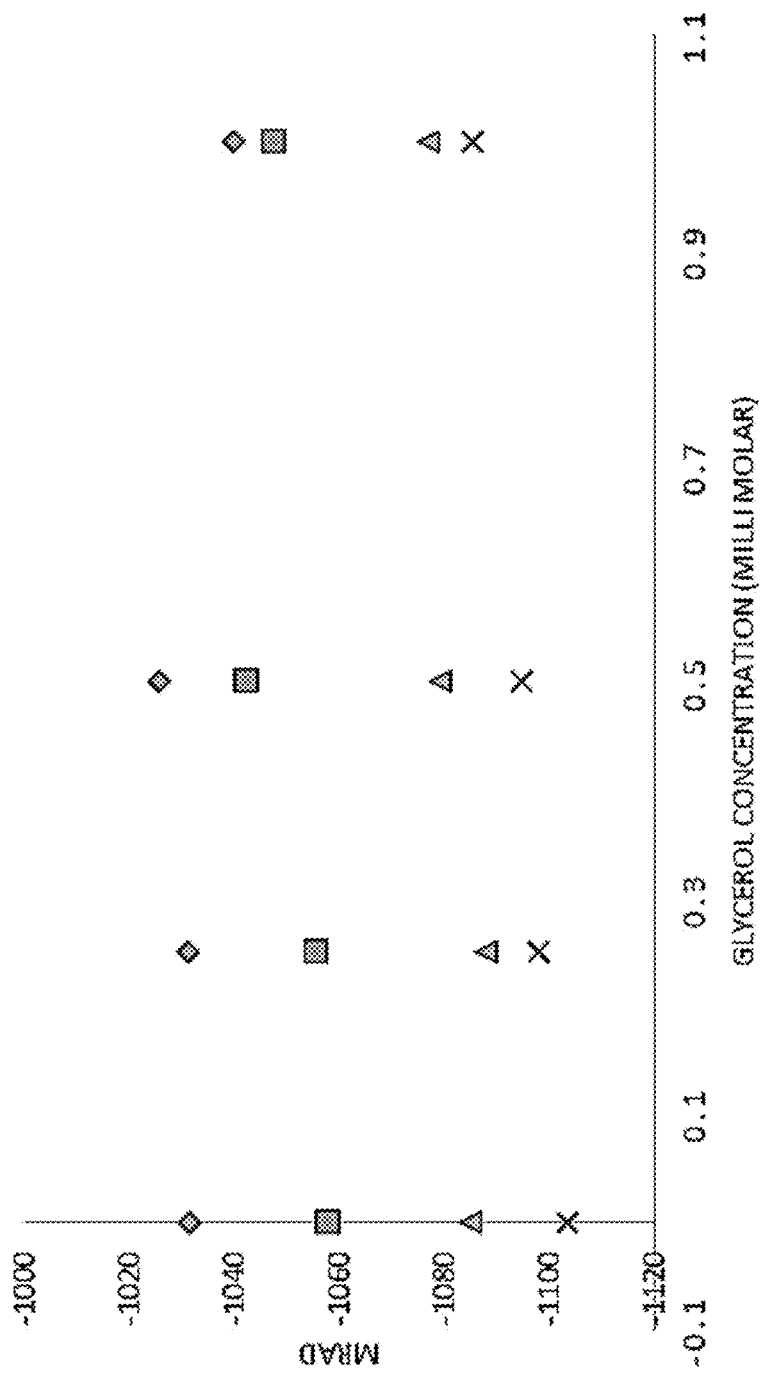

Glycerol curves in sodium acetate buffer with no temperature controller are shown in FIGS. 16A (SCSR configuration) and 16B (standard configuration). The experimental data is illustrated in Table 3.

TABLE 3

|  | SCSR | Standard |
| --- | --- | --- |
| Ambient ΔT during experiment | ° C. | 19.33-19.57° C. |

TABLE 3-continued

|  | SCSR | Standard |
| --- | --- | --- |
| Slope | 17.46 mrad/mmol | 11.21 mrad/mmol |
| $R^2$ | 0.9679 | 0.9601 |
| Standard Deviation | 1.36 mrad | 1.28 mrad |
| Injection Reproducibility | 1.10 mrad | 28.00 mrad |
| LOQ | 0.189 mmol | 7.496 mmol |
| LOD | 0.235 mmol | 0.342 mmol |

Figure 17A:
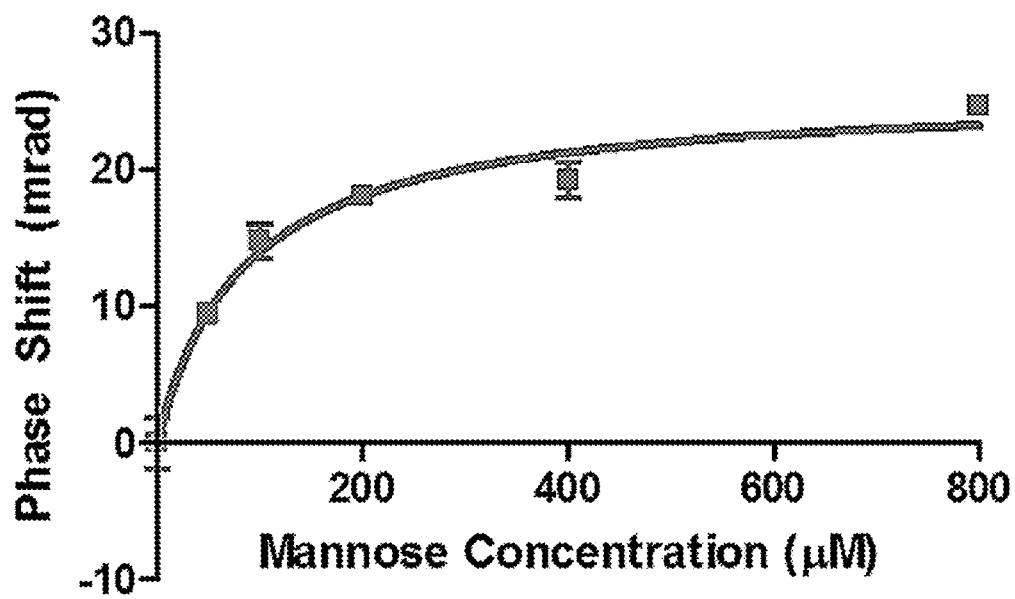
FIGS. 17A and 17B show representative data pertaining to binding assays performed using the SCSR configuration without temperature control.

A ConA-Mannose binding assay performed in PBS buffer using the SCSR configuration with no temperature control is shown in FIG. 17A. The experimental data is illustrated in Table 4. The phase shift values are illustrated in Table 5.

TABLE 4

|  | SCSR |
| --- | --- |
| $K_d$ | 84 ± 17 (published $K_d = 96 \pm 4$) |
| $R^2$ | 0.9822 |
| Standard Deviation over Phase Measurement | 1.958 mRad |
| Standard Deviation between Trials | 1.441 mRad |
| Limit of Detection | 39.76 µM |
| Limit of Quantification | 29.28 µM |

TABLE 5

| Mannose Concentration | Phase Shift (mRad) | Standard Deviation |
| --- | --- | --- |
| 0 | 0.00 | 3.200 |
| 50 | 9.45 | 0.566 |
| 100 | 14.77 | 1.773 |
| 200 | 18.11 | 0.175 |
| 400 | 19.26 | 2.293 |
| 800 | 24.70 | 0.644 |

Figure 17B:
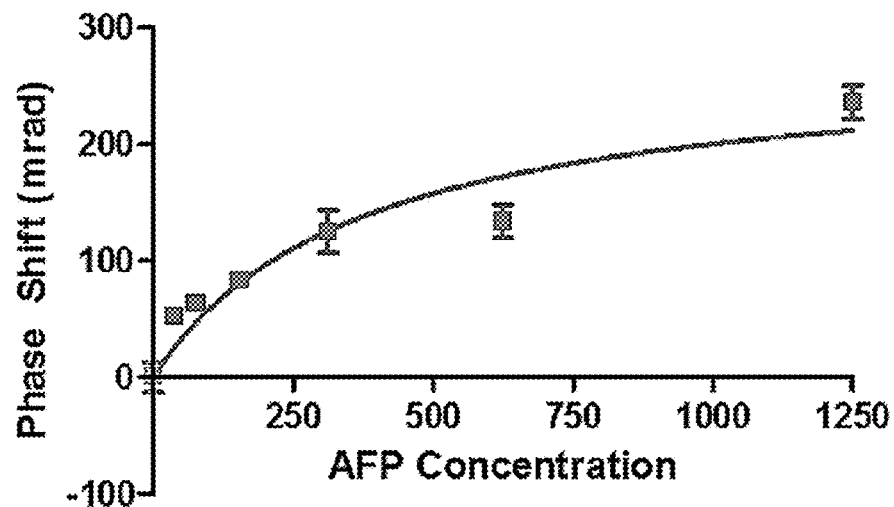

A AFP-anti-AFP binding assay performed in human urine using the SCSR configuration with no temperature control is shown in FIG. 17B.

7. Averaging Camera Pixels Improves Compensation

Figure 18:
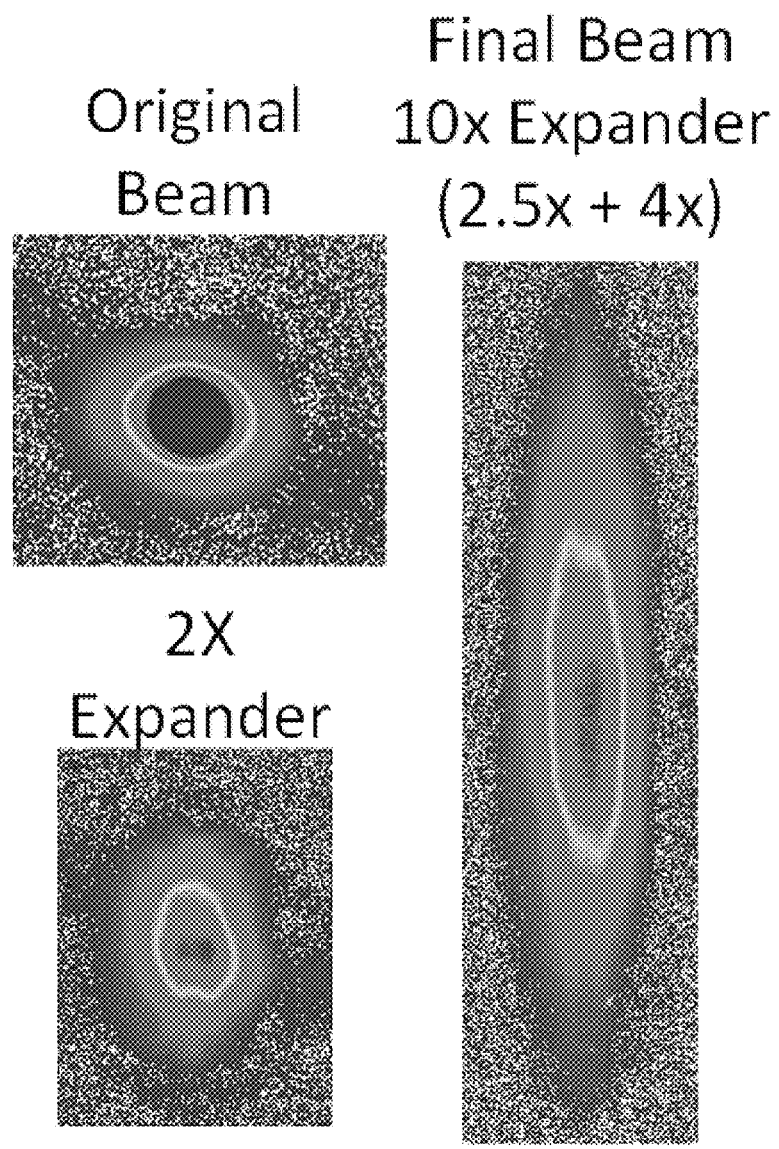
FIG. 18 shows representative images demonstrating various beam profiles achieved using SCSR-BSI including the original beam (top left), the original beam expanded 2× (bottom left), and the final beam expanded 10× (right).

Using the expanded beam illustrated in FIG. 18, the potential to improve the S/N by increasing fringe sampling was evaluated. A temperature calibration curve was run over two degrees, and the same fringes were averaged over 100 pixels (550 microns) and 200 pixels (1100 microns).

Figures 19A, 19B:
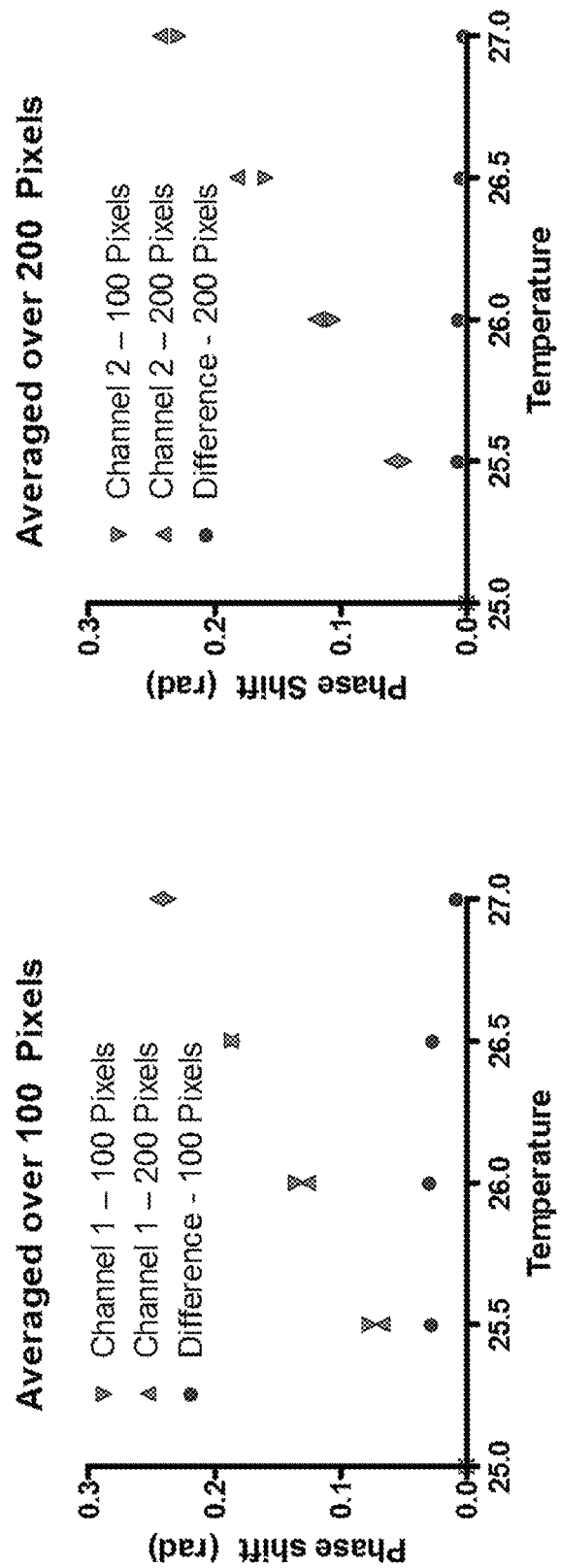
FIGS. 19A and 19B show representative data demonstrating that averaging over 100 (19A) and over 200 (19B) camera pixels improves compensation in SCSR-BSI.

FIGS. 19A and 19B shows that in this configuration, nearly 100% common mode rejection (CMR) was accomplished. Averaging over more pixels afforded improved compensation, and yielded "nicer" fringes (i.e., more rounded, fewer high frequencies present, more Gaussian shaped). Thus, the differences between the fringes from the sample and reference side are minimized Without wishing to be bound by theory, this can reduce the noise floor for BSI by >20-fold, relaxing or eliminating the requirement for high resolution temperature control, extreme mechanical stability, and control of laser pointing and wavelength stability. Environmental noise is well compensated for with the SCSR. Indeed, analysis time may be reduced by at least two-fold because the sample and the reference are interrogated simultaneously, allowing for a true difference measurement. Without wishing to be bound by theory, the SCSR may provide a >2500-fold reduction in noise due to temperature fluctuations.

8. Averaging Camera Pixels Improves Signal and Noise

Figure 20A:
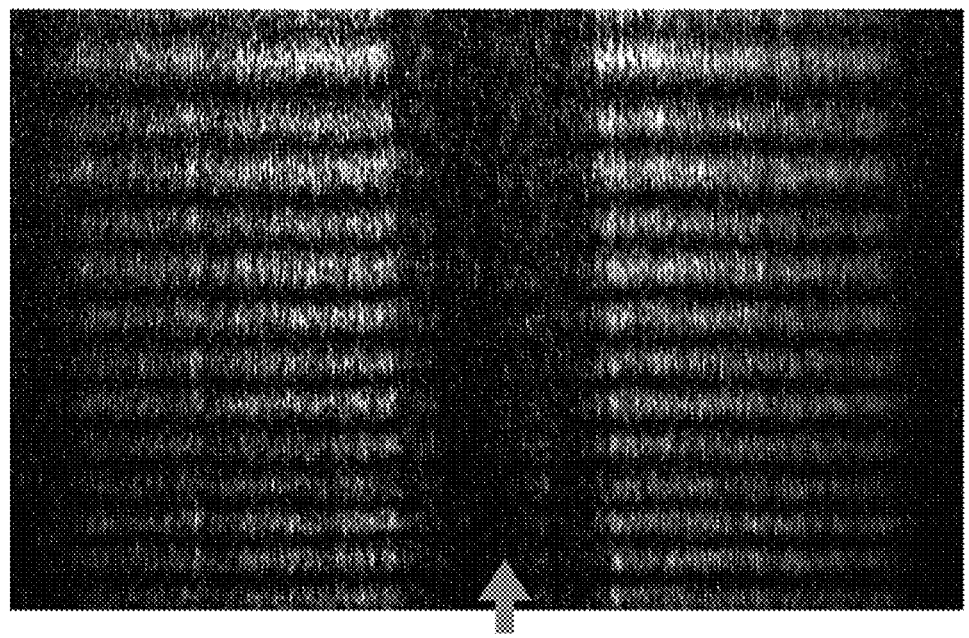
FIGS. 20A and 20B show representative data demonstrating that averaging camera pixels contributes to the improvement or the likeness of S and R fringes and thus the level of compensation.
Figure 20B:
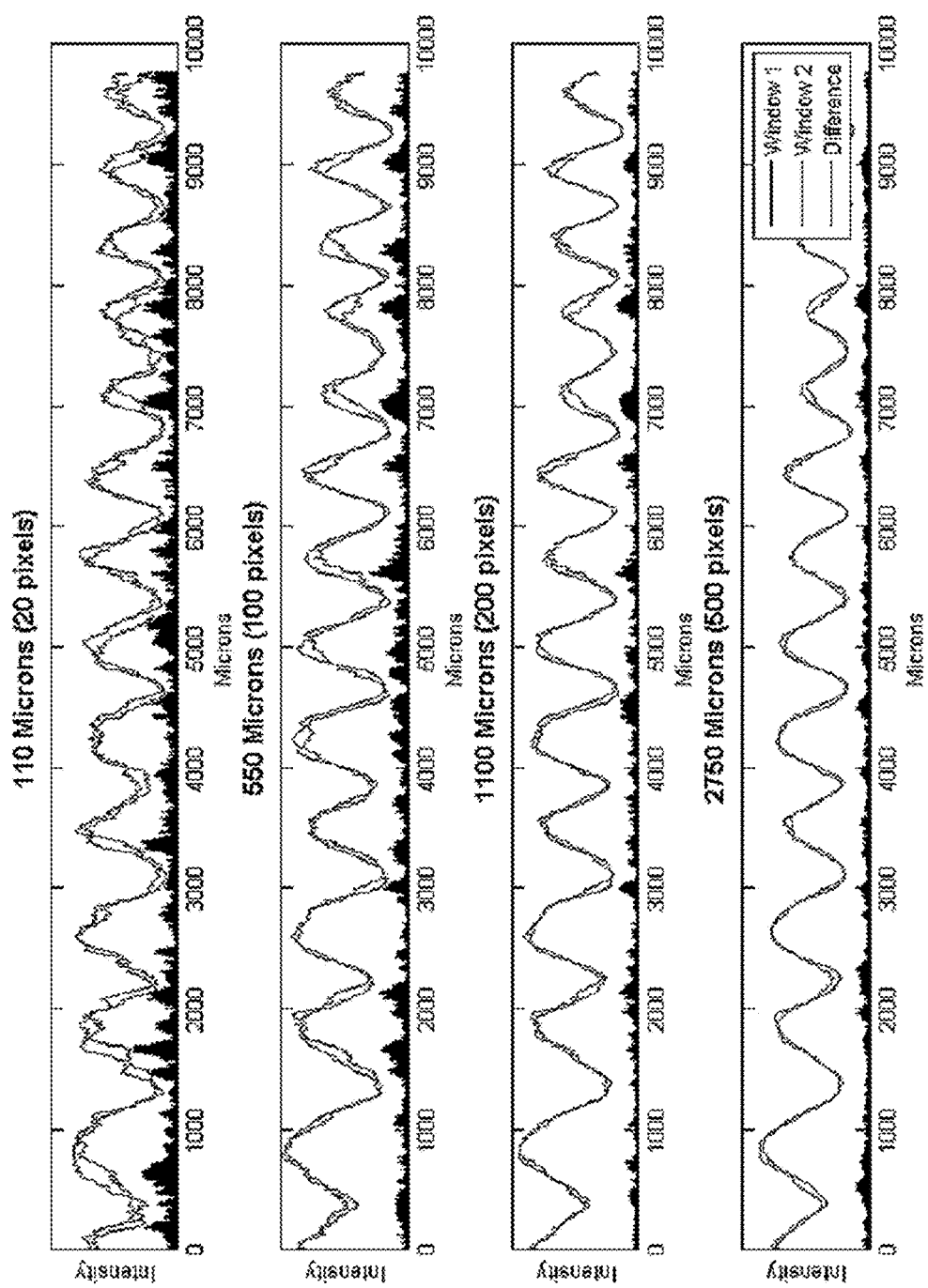

Both the signal and the noise are improved as a result of averaging over a several mm length (from about 4 mm to about 20 mm) of the channel. Without wishing to be bound by theory, this may be due to the fact that it produces fringes that mimic each (i.e., closer in shape, amplitude, and contrast ratio). As the fringes become more Gaussian, with an enhanced contrast ratio, the interferometer finesse increases resulting in a measurement sensitivity improvement. Since the two detection regions are nearly identical (FIGS. 20A and 20B) and since they are formed via a single beam, produced by a common source, there is compensation for mechanical vibrations, laser pointing instability, laser wavelength wander, and environmental temperature perturbations. Table 6 below summarizes results on how performance may be impacted by the number of camera rows (pixels) that are interrogated. Notice that by increasing the pixel interrogation zone, a nearly 10-fold improvement in compensation is obtained, resulting in noise reduction.

TABLE 6

|  | 100 Pixels | 200 Pixels |
| --- | --- | --- |
| Slope (rad/C) | 0.00302 | 0.0003942 |
| Compensation/C | $3 \times 10^{-7}$ | $4.1 \times 10^{-8}$ |

9. Fringe Position Quantification

As detailed above, optimum camera integration dimensions are dependent on chip configurations and the distances from the chip top surface to the camera sensor. Here, the optimum channel interrogation length over which to average the signal was determined to be approximately 2 mm per window.

Fringe position quantification can be performed with the necessary precision to produce fM molecular interaction sensitivity by using: 1) a cross correlation; 2) fast Fourier transform (FFT); and 3) an alternative approached based on the difference algorithm described herein. Each method has advantages and limitations due either to speed, computational demands, and simplicity of implementation.

Figure 21:
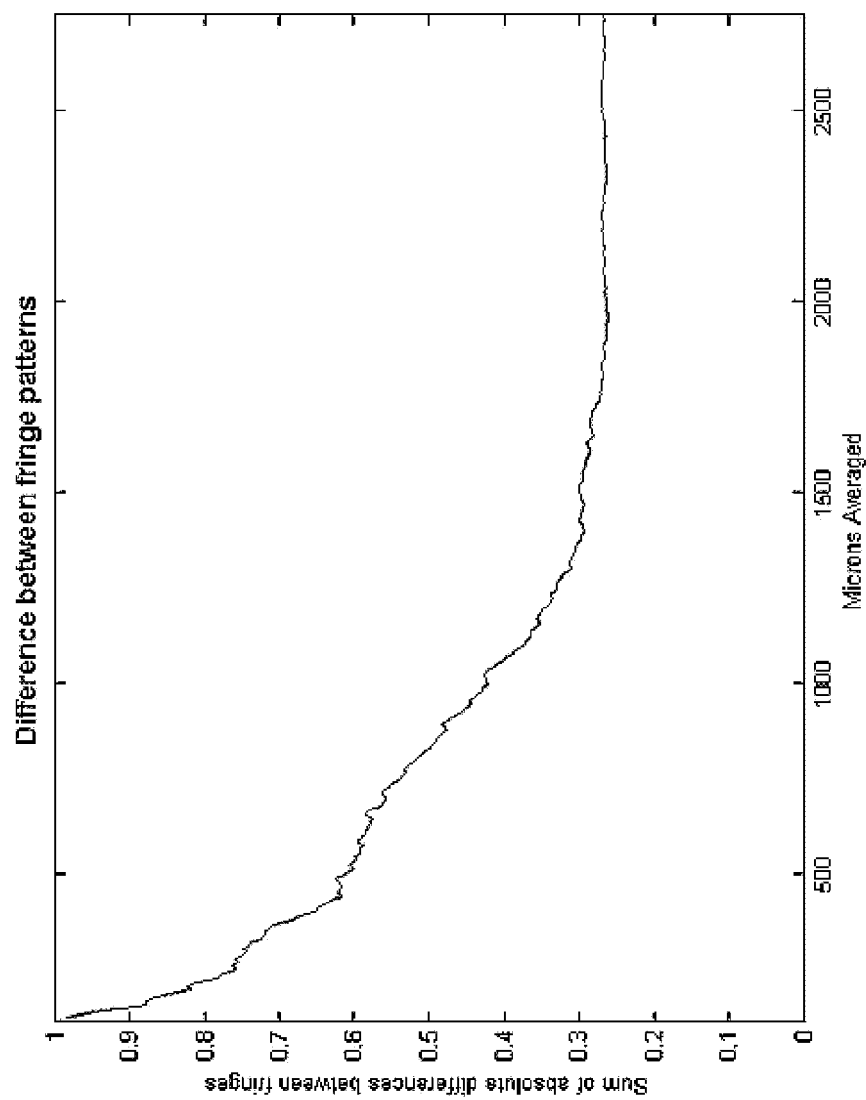
FIG. 21 shows representative data demonstrating the normalized sum of the differences of the sample and reference channels as a function of how much of the channel is averaged.

FIG. 21 shows the (normalized) sum of the differences of the S&R channels as a function of how much of the channel is averaged. Under these conditions, a point of diminishing returns when integrating the image for about 2000 microns (2 mm) of channel and approximately 250 camera pixels.

It is noteworthy that, given the nature of the chip manufacturing process and the non-uniformity of the channel in the long axis, it would not have been predicted that this approach could produce interferometers with essentially identical optical properties. Even though they are physically not identical (e.g., shape, smoothness, etc.), when the channels are interrogated over some distance they are effectively the same shape, width, and reflectivity. For this chip and channel, the interrogated distance is just over 2 mm of the channel, with the 2 or more discrete regions separated by approximately several mm, for example, between 1-4 mm.

10. Quantitative Assessment of Fringe Uniformity

Figure 22:
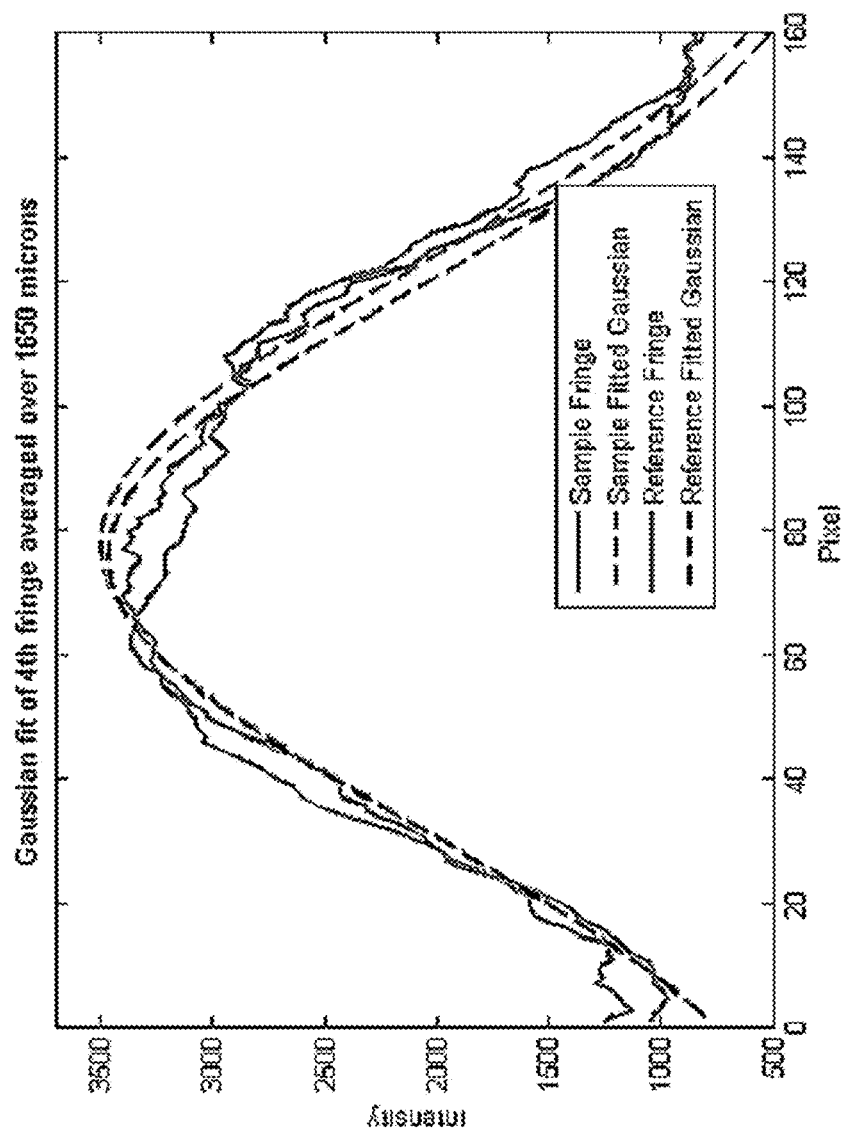
FIG. 22 shows representative data demonstrating the Gaussian fitting results for a single fringe illustrating that increasing the interrogation region, the length of the channel, and/or the camera results in at least two identical interferometers.

To quantitatively assess fringe uniformity as a result of averaging over a longer section of channel, each fringe was fitted to a Gaussian. The graph in FIG. 22 shows an example of this result for a single fringe. This fitting algorithm was applied to each of the 24 interrogated fringes (12 fringes in the two windows) and over a range of channel lengths (averaged), with the difference between an ideal Gaussian fit and the actual fringe shape allowing a quantitative method to predict performance. Without wishing to be bound by theory, this methodology may enable the system to electronically perform configuration optimization, resulting in an extremely accurate BSI alignment. Additionally, this calculation may allow for the determination of the minimal interrogation region to be used (i.e., the least computationally intensive and most rapid). A better fit signifies that a fringe is less "misshapen."

Figure 23:
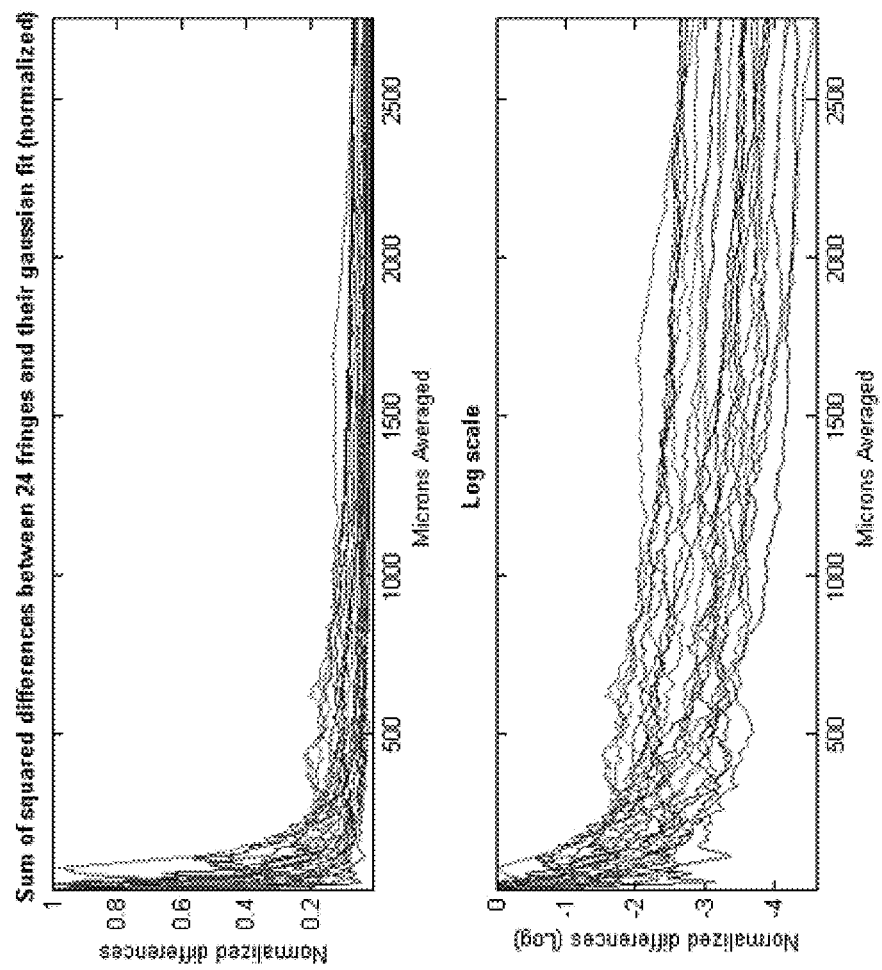
FIG. 23 shows representative data demonstrating the Gaussian fitting results for 24 fringes illustrating that increasing the interrogation region, the length of the channel, and/or the camera results in at least two identical interferometers.

In FIG. 23 the difference between the Gaussian fit and the real fringe is displayed for each of the 24 fringes (12 fringes in 2 windows). Each line shows one fringe, and in this instance, little improvement in fringe quality is realized for more than 1800 microns of interrogation, as measured by the Gaussian being the ideal or desirable outcome. Although this graph doesn't flatten out completely, it does offer considerable information that is critical to performing BSI assays, particularly when it is desirable to follow fewer fringes as might be desirable when doing ultra-fast assays, when using less expensive cameras with lower resolution, and distinguishing the surface signal from the bulk. Additionally, the Gaussian fitting to each fringe may determine how it shifts in position with respect to the adjacent and distant fringes to enable further compensation for common mode noise. The distribution of these fits also contains information that may be used to increase S/N by averaging. Thus, without wishing to be bound by theory, this may provide a method to expand the dynamic operation range for BSI.

11. Evaluation of Vertical Droplet Height for IDEX Fittings

Numerous tests were performed in order to define the parameters needed to enable the instrument to work consistently and with high reproducibility. These parameters include the guide inner diameter, aspect ratio of the channel, total length of guide, distance of the bottom of the guide to the top of the chip, the appropriate surface, port channel height vs. diameter, and port material.

The final injection approach was as follows: 1) a drop of sample is dispensed into the opening of a receptacle; 2) the drop falls or wicks to the bottom of the inlet receptacle; and 3) the drop makes contact with the chip/channel.

Figure 24:
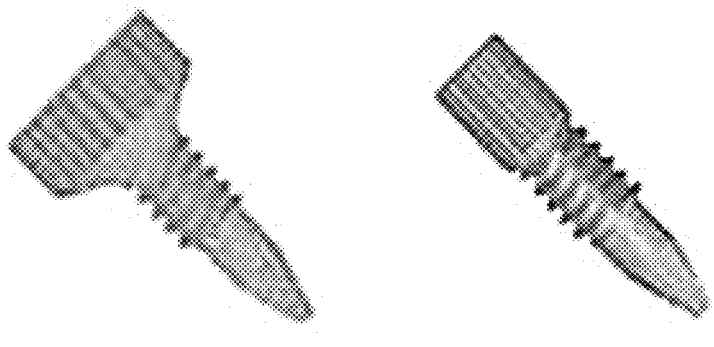
FIG. 24 shows a representative image illustrating a F-126Sx and F-126Hx IDEX fittings that can be used as an inlet guide, sample reservoir and injection port with SCSR-BSI.

To evaluate the efficacy of using an off-the-shelf tubing connector as the sample guide (receptacle), the distance that a droplet hangs from the inlet or size of the droplet was measured. Determining this parameter is necessary to ensure that the drop hangs below the introduction guide allowing it to touch the chip so that it can be wicked into the channel. Measurements were averaged over three trials. Using IDEX fitting F-126Sx (FIG. 24) the results shown in Table 5 were obtained, with no measurable drop extended below the bottom of the fitting opening for a sample volume <6 μL. Droplet heights were the same for the F-126Hx fitting, which has a smaller opening.

TABLE 5

| $H_2O$ | | PBS | |
| --- | --- | --- | --- |
| Volume (μL) | Droplet Height (mm) | Volume (μL) | Droplet Height (mm) |
| 6 | 1.360297 | 6 | 1.100116 |
| 7 | 1.492365 | 7 | 1.302595 |
| 8 | 1.836663 | 8 | 1.445519 |
| 9 | 1.967304 | 9 | 1.652337 |
| 10 | 2.190494 | 10 | 1.943471 |

Furthermore, adding 0.1% tween to water produced no measurable droplet with 10 μL, yet modification of the receptacle surface to make it more hydrophobic enabled 6

μL to be injected. Without wishing to be bound by theory, larger inner diameter connectors may allow for a smaller volume to be injected with the result of a drop distending below the connector and allowing for capillary action to take over.

12. General Procedural Considerations for SCSR BSI

Samples can be prepared as in a conventional BSI assay. In one aspect, once samples are prepared and have been incubated for the appropriate amount of time, the samples can be injected into the instrument. Further samples can be injected sequentially, repeating for the desired number of trials, until all desired data is collected.

Generally, to inject a sample into the SCSR Instrument, one can (1) ensure the channel is completely empty/dry by applying a vacuum (e.g., a few torr) on the center hole (outlet) to empty both sides of the channel; (2) ensure the vacuum is off; (3) beginning with the reference solution, use a pipetter to dispense a 5 μL drop of the solution into the reference-side injection fitting; (4) wait for a sufficient period of time (e.g., several seconds and up to 5 seconds for vicious fluids) for the sample to be wicked into the channel by capillary action; (5) ensure that the channel has been filled as indicated by observing stable, high contrast interference fringes; (6) on the opposite side of the chip, repeat the injection procedure for the sample solution; (7) record data by analyzing the fringes impinging upon the camera; (8) remove solutions by applying vacuum/pressure to the center hole; (9) rinse both sides of the channel with the appropriate rinse solutions (water, buffer, chloroform, methanol, etc.); and (10) ensure the channel is clean and empty before beginning the next injection. One of skill would appreciate that fringe pattern can be used to determine the channel is empty.

13. Phase Shift Due to Evaporation

Figure 28A:
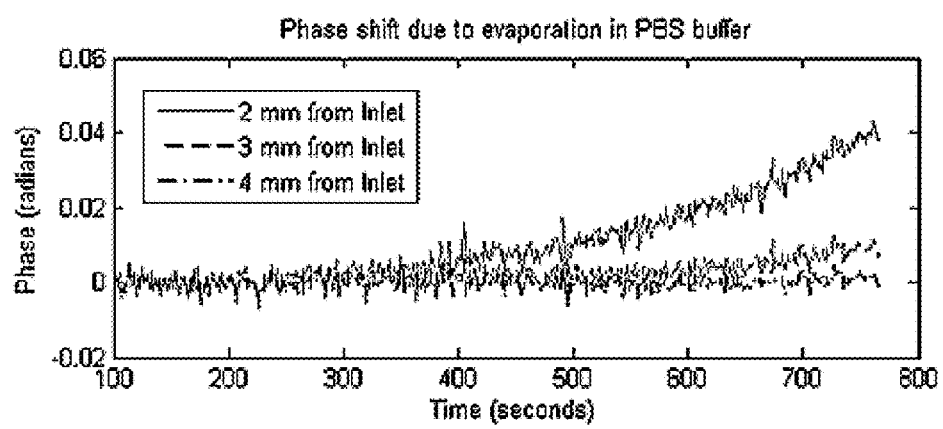
FIG. 28A and FIG. 28B show results from two experiments performed to measure phase shift due to evaporation at different locations along the channel in PBS Buffer (28A) and in PBS buffer with 1% DMSO (28B).
Figure 28B:
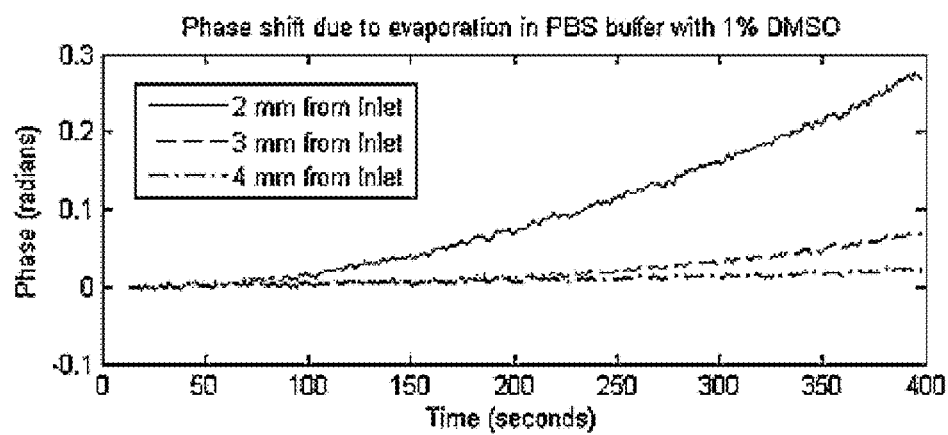

Two experiments were performed to measure phase shift due to evaporation at three locations along the channel, using PBS (FIG. 28, top) and PBS with 1% DMSO (FIG. 28, bottom). In this example, the 1.7 mm of the channel closest to the inlet well is covered by the chip-holder, and is inaccessible for interrogation, so distances of 2 mm, 3 mm, and 4 mm were chosen. The interrogated fringes at each distance were a summation of 100 pixels (0.55 mm) that were centered at the recorded distance. For example, the "2 mm" data was collected from 1.725 to 2.275 mm from the inlet well. These measurements were made with no closure element (i.e., the inlet well was exposed to the atmosphere) and a sample size of 1.5 μL.

Figures 29A, 29B:
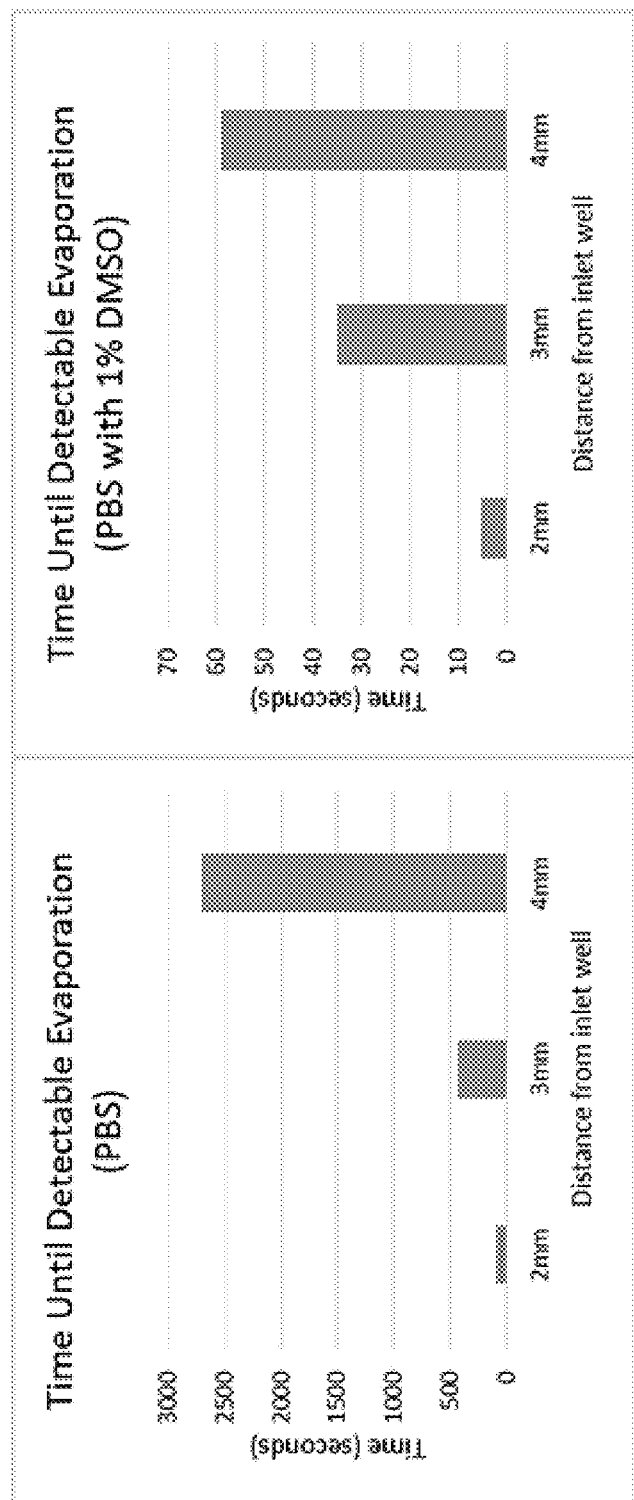
FIG. 29A and FIG. 29B show calculated time until "detectable evaporation" in PBS buffer (29A) and in PBS buffer with 1% DMSO (29B).

To calculate how much time can pass before evaporation would affect the reading at a point along the channel, the time until "detectable evaporation" was calculated. "Detectable evaporation" was determined as when this fitted curve deviated 0.001 radians from its starting position. See FIG. 29. The time until detectable evaporation was much quicker closer to the inlet well, and also much quicker for the solution containing 1% DMSO. Even with 1% DMSO, it takes about a full minute for the evaporation to influence the phase reading at a distance of 4 mm from the inlet well. Since measurements typically take no longer than thirty seconds once sample is injected, it can be desirable to select a distance that achieves a time until "detectable evaporation" of at least thirty seconds.

In one aspect, for PBS solutions, a distance of 2 mm can be an acceptable distance. In a further aspect, for PBS solutions containing 1% DMSO, a distance of 4 mm can be an acceptable distance.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for determining a characteristic property of a sample comprising the steps of:
    (a) providing a sample positioned inside a channel of a capillary tube, wherein the channel has a longitudinal direction and a transverse direction;
    (b) interrogating the sample with a light beam, wherein the light beam is elongated in the longitudinal direction of the channel, such that the light beam is incident on at least a portion of the channel, wherein a length of the incidence is greater than 8 mm in length along the longitudinal direction; and
    (c) generating scattered light through reflective and refractive interaction of the light beam with a substrate/channel interface and the sample, the scattered light comprising interference fringe patterns elongated in at least one direction, wherein the interference fringe patterns shift in response to changes in the refractive index of the sample.

2. The method of claim 1, further comprising the steps of receiving a plurality of intensity signals with a signal analyzer and determining therefrom one or more characteristic properties of the sample.

3. The method of claim 1, wherein the light beam is incident on at least a portion of the channel, wherein a length of the incidence is greater than 10 mm in length along the longitudinal direction.

4. The method of claim 1, wherein the scattered light is backscattered light.

5. A method for determining a characteristic property of a sample comprising the steps of:
    (a) providing a capillary tube having a channel formed therein, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel on one side of the at least one outlet and a left side of the channel on another side of the at least one outlet;
    (b) introducing a first sample into the left side of the channel;
    (c) introducing a second sample into the right side of the channel;
    (d) simultaneously interrogating the samples with a light beam, wherein the light beam is elongated in the longitudinal direction of the channel, such that the light beam is incident on at least a portion of the left side of the channel and the right side of the channel; and
    (e) generating scattered light through reflective and refractive interaction of the light beam with a substrate/channel interface and the samples, the scattered light comprising interference fringe patterns elongated in at least one direction, wherein the interference fringe patterns shift in response to changes in the refractive index of the sample.

6. The method of claim 5, further comprising the steps of receiving a plurality of intensity signals with a signal analyzer and determining therefrom one or more characteristic properties of at least one of the sample.

7. The method of claim 5, wherein the light beam is incident on at least a portion of the channel, wherein a length of the incidence is greater than 4 mm in length along the longitudinal direction.

8. The method of claim 5, wherein the scattered light is backscattered light.

9. The method of claim 5, wherein the light beam is incident on at least a portion of the channel, wherein a length of the incidence is greater than 8 mm in length along the longitudinal direction.

10. The method of claim 5, wherein the first and second samples are introduced substantially simultaneously.

11. An interferometric detection system comprising:
(a) a capillary tube having a channel formed therein, wherein the channel has a longitudinal direction and a transverse direction, and wherein the channel is configured for reception of two or more liquid samples by having at least two inlets positioned at opposing locations of the channel, and at least one outlet positioned at a point between the at least two inlets, thereby defining a right side of the channel on one side of the at least one outlet and a left side of the channel on another side of the at least one outlet;
(b) a light source for generating a light beam, wherein the light beam is elongated in the longitudinal direction of the channel, and wherein the light source is positioned to direct the light beam onto the channel such that the light beam is simultaneously incident on at least a portion of the right side of the channel and at least a portion of the left side of the channel, such that, during operation, scattered light is generated through reflective and refractive interaction of the light beam with a channel interface and the two or more samples, the scattered light comprising interference fringe patterns elongated in at least one direction, wherein the interference fringe patterns shift in response to changes in the refractive index of the two or more samples; and
(c) a photodetector for simultaneously receiving the scattered light and generating a plurality of intensity signals.

12. The interferometric detection system of claim 11, further comprising at least one signal analyzer for receiving a plurality of intensity signals and determining therefrom one or more characteristic properties of the two or more samples.

13. The interferometric detection system of claim 11, further comprising a plurality of reservoirs, wherein each of the plurality of reservoirs is in fluid communication with one of the at least two inlets.

14. The interferometric detection system of claim 11, further comprising two or more samples, wherein at least one of the two or more samples comprises a reference.

15. The interferometric detection system of claim 11, further comprising scattered light received by the photodetector, wherein the scattered light comprises backscattered light.

16. The interferometric detection system of claim 11, wherein a single light beam is incident upon the channel.

17. The interferometric detection system of claim 11, further comprising an optical element positioned between the light source and the channel, wherein the optical element is capable of at least one of spreading, splitting, rastering, or a combination thereof the light beam in a direction parallel to the length of the channel.

18. The interferometric detection system of claim 17, wherein the optical element is capable of spreading the light beam in a direction parallel to the length of the channel.

19. The interferometric detection system of claim 11, wherein the photodetector is capable of spatially resolving scattered light incident on a surface thereof.

20. The interferometric detection system of claim 11, wherein a first discrete zone is disposed between a first inlet and the at least one outlet, and wherein a second discrete zone is disposed between a second inlet and the at least one outlet.

* * * * *